US012747432B2

(12) United States Patent
Ewaisha et al.

(10) Patent No.: US 12,747,432 B2
(45) Date of Patent: Sep. 29, 2026

(54) MODULATING HUMAN Cas9-SPECIFIC HOST IMMUNE RESPONSE

(71) Applicant: Arizona Board of Regents on behalf of Arizona State University, Scottsdale, AZ (US)

(72) Inventors: Radwa Ewaisha, Tempe, AZ (US); Samira Kiani, Scottsdale, AZ (US); Shayesteh Roshdi Ferdosi, Tempe, AZ (US); Karen Anderson, Scottsdale, AZ (US); Farzaneh Moghadam, Tempe, AZ (US); Sri Krishna, Tempe, AZ (US); Mo Reza Ebrahimkhani, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 235 days.

(21) Appl. No.: 18/778,083

(22) Filed: Jul. 19, 2024

(65) Prior Publication Data

US 2024/0368572 A1 Nov. 7, 2024

Related U.S. Application Data

(62) Division of application No. 17/546,810, filed on Dec. 9, 2021, now Pat. No. 12,084,691, which is a division of application No. 16/632,782, filed as application No. PCT/US2018/029937 on Apr. 27, 2018, now Pat. No. 11,208,640.

(60) Provisional application No. 62/556,061, filed on Sep. 8, 2017, provisional application No. 62/535,516, filed on Jul. 21, 2017.

(51) Int. Cl.

| | |
|---|---|
| ***C12N 9/22*** | (2006.01) |
| ***A61K 48/00*** | (2006.01) |
| ***G01N 33/573*** | (2006.01) |

(52) U.S. Cl.

CPC ............. *C12N 9/22* (2013.01); *G01N 33/573* (2013.01); *A61K 48/00* (2013.01); *C12N 2310/20* (2017.05); *C12N 2800/80* (2013.01); *G01N 2333/922* (2013.01)

(58) Field of Classification Search

CPC .. C12N 9/22; C12N 2310/20; C12N 2800/80; G01N 33/573; G01N 2333/922; A61K 48/00

See application file for complete search history.

(56) References Cited

U.S. PATENT DOCUMENTS

| | | | |
|---|---|---|---|
| 9,857,374 | B2 | 1/2018 | LaBaer |
| 2014/0273226 | A1 | 9/2014 | Wu |
| 2015/0362497 | A1 | 12/2015 | Anderson |
| 2017/0045515 | A1 | 2/2017 | Anderson |
| 2017/0059563 | A1 | 3/2017 | Smith |
| 2017/0176423 | A1 | 6/2017 | Anderson |
| 2017/0177788 | A1 | 6/2017 | Anderson |
| 2017/0205409 | A1 | 7/2017 | Anderson |
| 2017/0363631 | A1 | 12/2017 | LaBaer |
| 2018/0067117 | A1 | 3/2018 | LaBaer |
| 2018/0172681 | A1 | 6/2018 | Katchman |
| 2018/0320230 | A1 | 11/2018 | LaBaer |
| 2019/0290248 | A1 | 9/2019 | Katchman |
| 2019/0302122 | A1 | 10/2019 | Katchman |
| 2020/0182874 | A1 | 6/2020 | LaBaer et al. |
| 2020/0191782 | A1 | 6/2020 | Katchman et al. |

FOREIGN PATENT DOCUMENTS

| | | | |
|---|---|---|---|
| WO | 2012021887 | A2 | 2/2012 |
| WO | 2014120902 | A1 | 8/2014 |
| WO | 2015148202 | A1 | 10/2015 |
| WO | 2015148216 | A1 | 10/2015 |
| WO | 2015148273 | A2 | 10/2015 |
| WO | 2015167678 | A1 | 11/2015 |
| WO | 2015167678 | A8 | 11/2015 |
| WO | 2015168515 | A1 | 11/2015 |
| WO | 2016089866 | A1 | 6/2016 |
| WO | 2016094558 | A1 | 6/2016 |
| WO | 2016112242 | A1 | 7/2016 |
| WO | 2016195918 | A1 | 12/2016 |
| WO | 2017075141 | A1 | 5/2017 |
| WO | 2017075141 | A8 | 5/2017 |
| WO | 2017081288 | A1 | 5/2017 |
| WO | 2017197238 | A1 | 11/2017 |
| WO | 2018013531 | A1 | 1/2018 |
| WO | 2018013531 | A8 | 1/2018 |
| WO | 2018013579 | A1 | 1/2018 |
| WO | 2019099723 | A2 | 5/2019 |

OTHER PUBLICATIONS

Ahi, Y.S., et al. Adenoviral Vector Immunity: Its Implications and circumvention strategies. Current gene therapy 11, 307-320 (2011).
Aldhamen, Y.A. et al., 16—Methods to Mitigate Immune Responses to Adenoviral Vectors A2—Curiel, David T, in Adenoviral Vectors for Gene Therapy (Second Edition). 2016, Academic Press: San Diego. p. 391-422.

(Continued)

*Primary Examiner* — Paul J Holland

(74) *Attorney, Agent, or Firm* — Quarles & Brady LLP

(57) ABSTRACT

Provided herein are methods and compositions for reducing an undesirable T cell immune response in human patients prior to and/or during gene therapy using CRISPR/Cas9-based genetic modulation.

3 Claims, 19 Drawing Sheets

Specification includes a Sequence Listing.

(56) References Cited

OTHER PUBLICATIONS

Anderson, K.S. et al. HPV16 antibodies as risk factors for oropharyngeal cancer and their association with tumor HPV and smoking status. Oral oncology 51, 662-667 (2015).
Bartel, M., et al. Enhancing the Clinical Potential of AAV Vectors by Capsid Engineering to Evade Pre-Existing Immunity. Front Microbiol 2, 204 (2011).
Belz, G. T., et al. "A previously unrecognized H-2Db-restricted peptide prominent in the primary influenza A virus-specific CD8+ T-cell response is much less apparent following secondary challenge." Journal of virology 74.8 (2000): 3486-3493.
Boutin, S., et al., Prevalence of serum IgG and neutralizing factors against adeno-associated virus (AAV) types 1, 2, 5, 6, 8, and 9 in the healthy population: implications for gene therapy using AAV vectors. Hum Gene Ther, 2010. 21(6): p. 704-12.
Brunetti-Pierri, N. et al., Progress towards liver and lung-directed gene therapy with helper-dependent adenoviral vectors. Curr Gene Ther, 2009. 9(5): p. 329-40.
Cantor, J.R. et al. Therapeutic enzyme deimmunization by combinatorial T-cell epitope removal using neutral drift. Proc Natl Acad Sci U S A 108, 1272-1277 (2011).
Carapetis, J.R., et al., The global burden of group A streptococcal diseases. Lancet Infect Dis, 2005. 5(11): p. 685-94.
Carter, P., et al. "Improved oligonudeotide site-directed rautagenesis using M13 vectors." Nucleic Acids Research 13.12 (1985): 4431-4443.
Cavazzana-Calvo, M. et al. Gene therapy of human severe combined immunodeficiency (SCID)-X1 disease. Science 288, 669-672 (2000).
Chen, W., et al. "Determinant selection of major histocompatibility complex class I-restricted antigenic peptides is explained by class I-peptide affinity and is strongly influenced by nondominant anchor residues." Journal of Experimental Medicine 180.4 (1994): 1471-1483.
Chen, W., et al. "Dissecting the multifactorial causes of immunodominance in class I-restricted T cell responses to viruses." Immunity 12.1 (2000): 83-93.
Chew, W.L. et al. A multifunctional AAV-CRISPR-Cas9 and its host response. Nat Methods 13, 868-874 (2016).
Chowell, D., et al., TCR contact residue hydrophobicity is a hallmark of immunogenic CD8+ T cell epitopes. Proc Natl Acad Sci U S A, 2015. 112(14): p. E1754-62.
Cyranoski, D. Chinese scientists to pioneer first human CRISPR trial. Nature News 535, 476 (2016).
Dobin, A. et al. STAR: ultrafast universal RNA-seq aligner. Bioinformatics 29, 15-21 (2013).
Esvelt, K.M., et al., Orthogonal Cas9 proteins for RNA-guided gene regulation and editing. Nat Methods, 2013. 10 (11): p. 1116-21.
Ferdosi, S. R., et al. "Multifunctional CRISPR/Cas9 with engineered immunosilenced human T cell epitopes." bioRxiv (2018): 360198.
Festa, F., et al. "High-throughput cloning and expression library creation for functional proteomics." Proteomics 13.9 (2013): 1381-1399.
Gao, G. et al. Adeno-associated virus-mediated gene transfer to nonhuman primate liver can elicit destructive transgene-specific T cell responses. Hum Gene Ther 20, 930-942 (2009).
Gaspar, H.B., et al., Gene therapy of X-linked severe combined immunodeficiency by use of a pseudotyped gammaretroviral vector. Lancet, 2004. 364(9452): p. 2181-7.
Hacein-Bey-Abina, S., et al., Sustained correction of X-linked severe combined immunodeficiency by ex vivo gene therapy. N Engl J Med, 2002. 346(16): p. 1185-93.
Halbert, C.L., et al., Successful readministration of adeno-associated virus vectors to the mouse lung requires transient immunosuppression during the initial exposure. J Virol, 1998. 72(12): p. 9795-805.
Hirano, H. et al. Structure and Engineering of Francisella novicida Cas9. Cell 164, 950-961 (2016).
Hoof, I. et al. NetMHCpan, a method for MHC class I binding prediction beyond humans. Immunogenetics 61, 1 (2009).
Howe, S.J., et al., Insertional mutagenesis combined with acquired somatic mutations causes leukemogenesis following gene therapy of SCID-X1 patients. J Clin Invest, 2008. 118(9): p. 3143-50.
International Searching Authority, International Search Report and Written Opinion for application PCT/US2018/029937, mailed on Aug. 31, 2018.
Jiang, H., et al., Effects of transient immunosuppression on adenoassociated, virus-mediated, liver-directed gene transfer in rhesus macaques and implications for human gene therapy. Blood, 2006. 108(10): p. 3321-8.
Jinek, M. et al. Structures of Cas9 endonucleases reveal RNA-mediated conformational activation. Science 343, 1247997 (2014).
Jinek, M., et al. "RNA-programmed genome editing in human cells." elife 2 (2013): e00471.
Kay, M.A. State-of-the-art gene-based therapies: the road ahead. Nat Rev Genet 12, 316-328 (2011).
King, C. et al. Removing T-cell epitopes with computational protein design. Proc Natl Acad Sci U S A 111, 8577-8582 (2014).
Krishna et al, Vaccine Design: Methods and Protocols: vol. 1: Vaccines for Human Diseases, 779-796 (2016).
Maggi, E., et al., Technological advances in precision medicine and drug development. Expert Rev Precis Med Drug Dev, 2016. 1(3): p. 331-343.
Manno, C.S., et al., Successful transduction of liver in hemophilia by AAV-Factor IX and limitations imposed by the host immune response. Nat Med, 2006. 12(3): p. 342-7.
Marshall, E. Gene Therapy Death Prompts Review of Adenovirus Vector. Science 286, 2244-2245 (1999).
Martino, A.T. et al. Engineered AAV vector minimizes in vivo targeting of transduced hepatocytes by capsid-specific CD8+ T cells. Blood 121, 2224-2233 (2013).
Mays, L.E. et al. The complex and evolving story of T cell activation to AAV vector-encoded transgene products. Mol Ther 19, 16-27 (2011).
Mazor, R. et al. Rational design of low immunogenic anti CD25 recombinant immunotoxin for T cell malignancies by elimination of T cell epitopes in PE38. Cell Immunol 313, 59-66 (2017).
Mingozzi, F. et al. CD8(+) T-cell responses to adeno-associated virus capsid in humans. Nat Med 13, 419-422 (2007).
Mingozzi, F. et al. Immune responses to AAV vectors: overcoming barriers to successful gene therapy. Blood 122, 23-36 (2013).
Mingozzi, F. et al. Overcoming preexisting humoral immunity to AAV using capsid decoys. Sci Transl Med 5, 194ra192 (2013).
Mok, H., et al. Enhancement of the CD8+ T cell response to a subdominant epitope of respiratory syncytial virus by deletion of an immunodominant epitope. Vaccine 26, 4775-4782 (2008).
Moutaftsi, M. et al. A consensus epitope prediction approach identifies the breadth of murine TCD8+-cell responses to vaccinia virus. Nature biotechnology 24, 817 (2006).
Nathwani, A.C. et al. Adenovirus-associated virus vector-mediated gene transfer in hemophilia B. N Engl J Med 365, 2357-2365 (2011).
Nayak, S. et al. Progress and prospects: immune responses to viral vectors. Gene Ther 17, 295-304 (2010).
Rammensee, H.-G., et al. SYFPEITHI: database for MHC ligands and peptide motifs. Immunogenetics 50, 213-219 (1999).
Ran, F.A. et al. In vivo genome editing using *Staphylococcus aureus* Cas9. Nature 520, 186-191 (2015).
Reardon, S. First CRISPR clinical trial gets green light from US panel. Nature (2016).
Robinson, M.D., et al. edgeR: a Bioconductor package for differential expression analysis of digital gene expression data. Bioinformatics 26, 139-140 (2010).
Salvat, R.S. et al. Computationally optimized deimmunization libraries yield highly mutated enzymes with low immunogenicity and enhanced activity. Proc Natl Acad Sci U S A 114, E5085-E5093 (2017).
Scallan, C.D. et al. Human immunoglobulin inhibits liver transduction by AAV vectors at low AAV2 neutralizing titers in SCID mice. Blood 107, 1810-1817 (2006).

(56) References Cited

OTHER PUBLICATIONS

Tangri, S. et al. Rationally engineered therapeutic proteins with reduced immunogenicity. J Immunol 174, 3187-3196 (2005).
Tenzer, S. et al. Modeling the MHC class I pathway by combining predictions of proteasomal cleavage, TAP transport and MHC class I binding. Cellular and Molecular Life Sciences 62, 1025-1037 (2005).
Thwaite, R., et al. AAVrh. 10 immunogenicity in mice and humans. Relevance of antibody cross-reactivity in human gene therapy. Gene Ther 22, 196-201 (2015).
Trapnell, C. et al. Differential gene and transcript expression analysis of RNA-seq experiments with TopHat and Cufflinks. Nature Protocols 7, 562-578 (2012).
Tscharke, DC et al. “From mice to humans-murine intelligence for human CD8+ T cell vaccine design.” Expert opinion on biological therapy 5.2 (2005): 263-271.
Vita, R. et al. The immune epitope database (IEDB) 3.0. Nucleic Acids Res 43, D405-412 (2015).
Wang, D. et al. Adenovirus-Mediated Somatic Genome Editing of Pten by CRISPR/Cas9 in Mouse Liver in Spite of Cas9-Specific Immune Responses. Hum Gene Ther 26, 432-442 (2015).
Wang, J. et al. A versatile protein microarray platform enabling antibody profiling against denatured proteins. Proteomics Clin Appl 7, 378-383 (2013).
Wolfl, M. et al. Activation-induced expression of CD137 permits detection, isolation, and expansion of the full repertoire of CD8+ T cells responding to antigen without requiring knowledge of epitope specificities. Blood 110, 201-210 (2007).
Yeung, V.P. et al. Elimination of an Immunodominant CD4+ T Cell Epitope in Human IFN-β Does Not Result in an In Vivo Response Directed at the Subdominant Epitope. The Journal of Immunology 172, 6658-6665 (2004).
Yin, H. et al. Non-viral vectors for gene-based therapy. Nat Rev Genet 15, 541-555 (2014).
Zetsche, B. et al. Cpf1 is a single RNA-guided endonuclease of a class 2 CRISPR-Cas system. Cell 163, 759-771 (2015).
Zoller, M. J., et al. “Oligonucleotide-directed mutagenesis using M13-derived vectors: an efficient and general procedure for the production of point mutations in any fragment of DNA.” Nucleic Acids Research 10.20 (1982): 6487-6500.
Chew WL et al. A multi-functional AAV-CRISPR Cas9 and its host response. 2016. Nature Methods. 13(10): 868-87 4. (Year: 2016).
Chew WL et al. A multi-functional AAV-CRISPR Cas9 and its host response. 2016. Nature Methods. Supplemental Materials. p. 1-33 (Year: 2016).
Tangri S et al. Rationally Engineered Therapeutic Proteins with Reduced Immunogenecity. 2005. Journal of Immunology. 17 4:3187-3196. (Year: 2005).

| | Rank | Position | Sequence | Code | HLA Binding | $S_b$ | $S_i$ | $S_b.S_i$ |
|---|---|---|---|---|---|---|---|---|
| SEQ ID NO:24 | 1 | 988-997 | YLNAVVGTAL | γ | 1.25 | 0.068 | 0.975 | 0.002 |
| SEQ ID NO:25 | 2 | 1281-1290 | ILADANLDKV | | 1.25 | 0.003 | 0.447 | 0.002 |
| SEQ ID NO:26 | 3 | 236-244 | GLFGNLIAL | δ | 0.6 | 0.020 | 0.900 | 0.002 |
| SEQ ID NO:27 | 4 | 240-248 | NLIALSLGL | α | 1.7 | 0.061 | 0.903 | 0.006 |
| SEQ ID NO:28 | 5 | 615-623 | ILEDIVLTL | β | 1.5 | 0.023 | 0.710 | 0.007 |

FIG. 7C

| Peptide Code (Position) | Peptide Sequence | Peptide Code (Position) | Peptide Sequence |
|---|---|---|---|
| α (240-248) | NLIALSLGL SEQ ID NO:27 | β (615-623) | ILEDIVLTL SEQ ID NO:28 |
| α2 | NGIALSLGL SEQ ID NO:77 | β2 | IGEDIVLTL SEQ ID NO:80 |
| α9 | NLIALSLGG SEQ ID NO:78 | β9 | ILEDIVLTG SEQ ID NO:81 |
| α29 | NGIALSLGG SEQ ID NO:79 | β29 | IGEDIVLTG SEQ ID NO:82 |

FIG. 12

| Amino Acid Position | Epitope Sequence | Code | IEDB bind | NetMHC bind | Syfpeithi bind | IEDB prot | ANN prot | Binding score | Sum proc | ANN Hydro | $S_b.S_i$ | Rank |
|---|---|---|---|---|---|---|---|---|---|---|---|---|
| 1041-1050 | YLNAVVGTAL | 98 | 1.25 | 21.5 | 24 | 0.27 | 0.02 | 0.068 | 0.027 | 0.975 | 0.002 | 1 |
| 1334-1343 | ILADANLDKV | 81 | 1.25 | 11.37 | 31 | -0.08 | -0.49 | 0.003 | 0.054 | 0.447 | 0.002 | 2 |
| 289-297 | GLFGNIJAL | 84 | 0.6 | 10.12 | 29 | 1.15 | 1.04 | 0.020 | 0.214 | 0.900 | 0.002 | 3 |
| 293-301 | NLNALRGL | 86 | 1.7 | 41.18 | 25 | 0.15 | 0.22 | 0.061 | 0.036 | 0.903 | 0.006 | 4 |
| 668-676 | ILEDIVTL | 85 | 1.5 | 13.29 | 28 | 0.26 | 0.58 | 0.021 | 0.062 | 0.710 | 0.007 | 5 |
| 667-676 | DILEDIVLTL | 96 | 4.6 | 3105.79 | 28 | -1.53 | -1.02 | 0.063 | 0.248 | 0.888 | 0.007 | 6 |
| 468-476 | MLSELHAIL | 99 | 4.4 | 276.73 | 29 | -0.79 | -0.81 | 0.071 | 0.152 | 0.876 | 0.009 | 7 |
| 353-361 | ILLSDILRV | 83 | 0.3 | 6.51 | 29 | 0.67 | 0.7 | 0.019 | 0.134 | 0.404 | 0.011 | 8 |
| 1139-1148 | VLSMPQVNIV | 93 | 3.65 | 178.87 | 26 | -1.05 | -1.43 | 0.059 | 0.243 | 0.758 | 0.014 | 9 |
| 1399-1408 | TLIHQSITGL | 88 | 1.95 | 57.8 | 27 | 0.12 | -0.06 | 0.043 | 0.017 | 0.632 | 0.016 | 10 |
| 1250-1259 | KLPKYSLFEL | 87 | 1.2 | 10.93 | 27 | 0.9 | 0.5 | 0.040 | 0.136 | 0.579 | 0.017 | 11 |
| 565-573 | SLLYEYFTV | 92 | 0.4 | 4.58 | 25 | 0.67 | 0.55 | 0.056 | 0.119 | 0.678 | 0.018 | 12 |
| 1280-1289 | ALPSKYVNFL | 91 | 4.3 | 111.34 | 27 | 0.05 | -0.26 | 0.051 | 0.030 | 0.594 | 0.021 | 13 |
| 1049-1057 | ALIKKYPEL | 86 | 2.6 | 134.09 | 28 | -0.27 | 0 | 0.037 | 0.025 | 0.407 | 0.022 | 14 |
| 274-282 | RLENLIAQL | 95 | 4.2 | 242.87 | 26 | -0.46 | -0.46 | 0.061 | 0.089 | 0.581 | 0.026 | 15 |
| 1290-1298 | YLASHYEKL | 90 | 1.1 | 10.3 | 26 | 0.8 | 0.84 | 0.050 | 0.170 | 0.446 | 0.027 | 16 |
| 795-803 | KVVDELVKV | 40 | 2.8 | 44.75 | 24 | -0.08 | -0.26 | 0.074 | 0.031 | 0.505 | 0.036 | 17 |
| 772-780 | SLHEHIANL | 82 | 1.4 | 9.14 | 30 | 0.83 | 0.62 | 0.013 | 0.171 | 0.380 | 0.008 | 18 |
| 1318-1326 | YLDEIKEQI | 89 | 0.3 | 4.8 | 26 | 0.82 | 0.6 | 0.046 | 0.119 | 0.399 | 0.028 | 19 |
| 604-613 | LLFKTNRKV | 97 | 3 | 381.3 | 25 | -1.52 | -1.25 | 0.067 | 0.270 | 0.368 | 0.043 | 20 |
| 772-781 | SLHEHIANLA | 13 | 4.7 | 80.17 | 19 | -0.98 | -1.74 | 0.126 | 0.268 | 0.890 | 0.014 | 21 |
| 1247-1256 | LIKKLPKYSL | 3 | 8.5 | 966.31 | 25 | -0.97 | -1.04 | 0.090 | 0.197 | 0.841 | 0.014 | 22 |
| 1094-1103 | NIMNFPKTEI | 12 | 2.65 | 314.8 | 19 | -1.03 | -0.8 | 0.121 | 0.188 | 0.857 | 0.017 | 23 |
| 1362-1371 | IIHLFTLTNL | | 4.25 | 1083.6 | 24 | -1.04 | -0.78 | 0.085 | 0.177 | 0.787 | 0.018 | 24 |
| 714-723 | RLSKKLLNGI | | 3.5 | 278.03 | 24 | -0.82 | -1.05 | 0.078 | 0.183 | 0.746 | 0.020 | 25 |
| 1095-1103 | IMNFPKTEI | | 3.2 | 131.4 | 21 | -0.69 | -0.87 | 0.105 | 0.153 | 0.724 | 0.028 | 26 |
| 868-877 | YLQNGRDMY V | | 0.25 | 13.01 | 22 | -0.18 | -0.87 | 0.083 | 0.025 | 0.617 | 0.031 | 27 |
| 1265-1273 | RMLASAGEL | | 3.2 | 333.2 | 22 | -0.64 | -0.51 | 0.095 | 0.112 | 0.850 | 0.033 | 28 |
| 1073-1082 | KMIAKSEQEI | | 3.1 | 84.03 | 21 | -0.36 | -0.9 | 0.103 | 0.124 | 0.671 | 0.034 | 29 |
| 846-854 | SQLLKEHPV | | 2.8 | 191.23 | 18 | -1.4 | -1.36 | 0.148 | 0.270 | 0.766 | 0.035 | 30 |
| 1234-1243 | FLEAKGYKEV | | 3.25 | 105.27 | 21 | -1.08 | -1.42 | 0.105 | 0.245 | 0.851 | 0.038 | 31 |
| 213-222 | HMIKFRGHFL | | 4.75 | 324.13 | 21 | -0.58 | -0.73 | 0.110 | 0.129 | 0.628 | 0.041 | 32 |
| 194-203 | KLVDSTDKA | | 3.4 | 274.05 | 20 | -1.48 | -1.17 | 0.114 | 0.258 | 0.520 | 0.055 | 33 |
| 525-534 | TITPWNFEEV | | 4.45 | 124.55 | 21 | -0.84 | -1.21 | 0.107 | 0.201 | 0.429 | 0.061 | 34 |
| 247-256 | QLFEENPINA | | 1.85 | 87.94 | 17 | -0.71 | -0.79 | 0.135 | 0.148 | 0.489 | 0.072 | 35 |
| 571-580 | FTVYNELTKV | | 2.55 | 188.93 | 20 | -1.12 | -1.15 | 0.111 | 0.222 | 0.216 | 0.087 | 36 |
| 526-534 | ITPWNFEEV | | 8.4 | 331.14 | 18 | -1.25 | -1.65 | 0.145 | 0.285 | 0.229 | 0.110 | 37 |
| 1023-1031 | FQFYKVREI | | 2.7 | 135.61 | 16 | -0.66 | -0.39 | 0.148 | 0.102 | 0.229 | 0.114 | 38 |

FIG. 13

MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVA
YHEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSASM
IKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTVKQLKEDYFKKIECF
DSVEISGVEDRFNASLGTYHDLLKIIKDKDFLDNEENEDILEDIVLTLTLFEDREMIEERLKTYAH
LFDDKVMKQLKRRRYTGWGRLSRKLINGIRDKQSGKTILDFLKSDGFANRNFMQLIHDDSLT
FKEDIQKAQVSGQGDSLHEHIANLAGSPAIKKGILQTVKVVDELVKVMGRHKPENIVIEMARE
NQTTQKGQKNSRERMKRIEEGIKELGSQILKEHPVENTQLQNEKLYLYYLQNGRDMYVDQEL
DINRLSDYDVDHIVPQSFLKDDSIDNKVLTRSDKNRGKSDNVPSEEVVKKMKNYWRQLLNAK
LITQRKFDNLTKAERGGLSELDKAGFIKRQLVETRQITKHVAQILDSRMNTKYDENDKLIREVK
VITLKSKLVSDFRKDFQFYKVREINNYHHAHDAYLNAVVGTALIKKYPKLESEFVYGDYKVYDV
RKMIAKSEQEIGKATAKYFFYSNIMNFFKTEITLANGEIRKRPLIETNGETGEIVWDKGRDFATV
RKVLSMPQVNIVKKTEVQTGGFSKESILPKRNSDKLIARKKDWDPKKYGGFDSPTVAYSVLV
VAKVEKGKSKKLKSVKELLGITIMERSSFEKNPIDFLEAKGYKEVKKDLIIKLPKYSLFELENGR
KRMLASAGELQKGNELALPSKYVNFLYLASHYEKLKGSPEDNEQKQLFVEQHKHYLDEIIEQI
SEFSKRVILADANLDKVLSAYNKHRDKPIREQAENIIHLFTLTNLGAPAAFKYFDTTIDRKRYTS
TKEVLDATLIHQSITGLYETRIDLSQLGGD (SEQ ID NO:1)

FIG. 14

ATGGATAAGAAATACTCAATAGGCTTAGATATCGGCACAAATAGCGTCGGATGGGCGGTGATCACTGATGAATATAAG
GTTCCGTCTAAAAAGTTCAAGGTTCTGGGAAATACAGACCGCCACAGTATCAAAAAAAATCTTATAGGGGCTCTTTTAT
TTGACAGTGGAGAGACAGCGGAAGCGACTCGTCTCAAACGGACAGCTCGTAGAAGGTATACACGTCGGAAGAATCGTA
TTTGTTATCTACAGGAGATTTTTTCAAATGAGATGGCGAAAGTAGATGATAGTTTCTTTCATCGACTTGAAGAGTCTTTT
TTGGTGGAAGAAGACAAGAAGCATGAACGTCATCCTATTTTTGGAAATATAGTAGATGAAGTTGCTTATCATGAGAAA
TATCCAACTATCTATCATCTGCGAAAAAAATTGGTAGATTCTACTGATAAAGCGGATTTGCGCTTAATCTATTTGGCCTT
AGCGCATATGATTAAGTTTCGTGGTCATTTTTTGATTGAGGGAGATTTAAATCCTGATAATAGTGATGTGGACAAACTA
TTTATCCAGTTGGTACAAACCTACAATCAATTATTTGAAGAAAACCCTATTAACGCAAGTGGAGTAGATGCTAAAGCGA
TTCTTTCTGCACGATTGAGTAAATCAAGACGATTAGAAAATCTCATTGCTCAGCTCCCCGGTGAGAAGAAAAATGGCTT
ATTTGGGAATCTCATTGCTTTGTCATTGGGTTTGACCCCTAATTTTAAATCAAATTTTGATTTGGCAGAAGATGCTAAAT
TACAGCTTTCAAAAGATACTTACGATGATGATTTAGATAATTTATTGGCGCAAATTGGAGATCAATATGCTGATTTGTTT
TTGGCAGCTAAGAATTTATCAGATGCTATTTTACTTTCAGATATCCTAAGAGTAAATACTGAAATAACTAAGGCTCCCC
TATCAGCTTCAATGATTAAACGCTACGATGAACATCATCAAGACTTGACTCTTTTAAAAGCTTTAGTTCGACAACAACT
TCCAGAAAAGTATAAAGAAATCTTTTTTGATCAATCAAAAAACGGATATGCAGGTTATATTGATGGGGGAGCTAGCCA
AGAAGAATTTTATAAATTTATCAAACCAATTTTAGAAAAAATGGATGGTACTGAGGAATTATTGGTGAAACTAAATCGT
GAAGATTTGCTGCGCAAGCAACGGACCTTTGACAACGGCTCTATTCCCCATCAAATTCACTTGGGTGAGCTGCATGCTA
TTTTGAGAAGACAAGAAGACTTTTATCCATTTTTAAAAGACAATCGTGAGAAGATTGAAAAAATCTTGACTTTTCGAAT
TCCTTATTATGTTGGTCCATTGGCGCGTGGCAATAGTCGTTTTGCATGGATGACTCGGAAGTCTGAAGAAACAATTACC
CCATGGAATTTTGAAGAAGTTGTCGATAAAGGTGCTTCAGCTCAATCATTTATTGAACGCATGACAAACTTTGATAAAA
ATCTTCCAAATGAAAAAGTACTACCAAAACATAGTTTGCTTTATGAGTATTTTACGGTTTATAACGAATTGACAAAGGT
CAAATATGTTACTGAAGGAATGCGAAAACCAGCATTTCTTTCAGGTGAACAGAAGAAAGCCATTGTTGATTTACTCTTC
AAAACAAATCGAAAAGTAACCGTTAAGCAATTAAAAGAAGATTATTTCAAAAAAATAGAATGTTTTGATAGTGTTGAA
ATTTCAGGAGTTGAAGATAGATTTAATGCTTCATTAGGTACCTACCATGATTTGCTAAAAATTATTAAAGATAAAGATT
TTTTGGATAATGAAGAAAATGAAGATATCTTAGAGGATATTGTTTTAACATTGACCTTATTTGAAGATAGGGAGATGAT
TGAGGAAAGACTTAAAACATATGCTCACCTCTTTGATGATAAGGTGATGAAACAGCTTAAACGTCGCCGTTATACTGGT
TGGGGACGTTTGTCTCGAAAATTGATTAATGGTATTAGGGATAAGCAATCTGGCAAAACAATATTAGATTTTTTGAAAT
CAGATGGTTTTGCCAATCGCAATTTTATGCAGCTGATCCATGATGATAGTTTGACATTTAAAGAAGACATTCAAAAAGC
ACAAGTGTCTGGACAAGGCGATAGTTTACATGAACATATTGCAAATTTAGCTGGTAGCCCTGCTATTAAAAAAGGTATT

FIG. 14 (cont.)

TTACAGACTGTAAAAGTTGTTGATGAATTGGTCAAAGTAATGGGGCGGCATAAGCCAGAAAATATCGTTATTGAAATG
GCACGTGAAAATCAGACAACTCAAAAGGGCCAGAAAAATTCGCGAGAGCGTATGAAACGAATCGAAGAAGGTATCAA
AGAATTAGGAAGTCAGATTCTTAAAGAGCATCCTGTTGAAAATACTCAATTGCAAAATGAAAAGCTCTATCTCTATTAT
CTCCAAAATGGAAGAGACATGTATGTGGACCAAGAATTAGATATTAATCGTTTAAGTGATTATGATGTCGATCACATTG
TTCCACAAAGTTTCCTTAAAGACGATTCAATAGACAATAAGGTCTTAACGCGTTCTGATAAAAATCGTGGTAAATCGGA
TAACGTTCCAAGTGAAGAAGTAGTCAAAAAGATGAAAAACTATTGGAGACAACTTCTAAACGCCAAGTTAATCACTCA
ACGTAAGTTTGATAATTTAACGAAAGCTGAACGTGGAGGTTTGAGTGAACTTGATAAAGCTGGTTTTATCAAACGCCAA
TTGGTTGAAACTCGCCAAATCACTAAGCATGTGGCACAAATTTTGGATAGTCGCATGAATACTAAATACGATGAAAATG
ATAAACTTATTCGAGAGGTTAAAGTGATTACCTTAAAATCTAAATTAGTTTCTGACTTCCGAAAAGATTTCCAATTCTAT
AAAGTACGTGAGATTAACAATTACCATCATGCCCATGATGCGTATCTAAATGCCGTCGTTGGAACTGCTTTGATTAAGA
AATATCCAAAACTTGAATCGGAGTTTGTCTATGGTGATTATAAAGTTTATGATGTTCGTAAAATGATTGCTAAGTCTGA
GCAAGAAATAGGCAAAGCAACCGCAAAATATTTCTTTTACTCTAATATCATGAACTTCTTCAAAACAGAAATTACACTT
GCAAATGGAGAGATTCGCAAACGCCCTCTAATCGAAACTAATGGGGAAACTGGAGAAATTGTCTGGGATAAAGGGCG
AGATTTTGCCACAGTGCGCAAAGTATTGTCCATGCCCCAAGTCAATATTGTCAAGAAAACAGAAGTACAGACAGGCGG
ATTCTCCAAGGAGTCAATTTTACCAAAAAGAAATTCGGACAAGCTTATTGCTCGTAAAAAAGACTGGGATCCAAAAAA
ATATGGTGGTTTTGATAGTCCAACGGTAGCTTATTCAGTCCTAGTGGTTGCTAAGGTGGAAAAAGGGAAATCGAAGAA
GTTAAAATCCGTTAAAGAGTTACTAGGGATCACAATTATGGAAAGAAGTTCCTTTGAAAAAAATCCGATTGACTTTTTA
GAAGCTAAAGGATATAAGGAAGTTAAAAAAGACTTAATCATTAAACTACCTAAATATAGTCTTTTTGAGTTAGAAAAC
GGTCGTAAACGGATGCTGGCTAGTGCCGGAGAATTACAAAAAGGAAATGAGCTGGCTCTGCCAAGCAAATATGTGAAT
TTTTTATATTTAGCTAGTCATTATGAAAAGTTGAAGGGTAGTCCAGAAGATAACGAACAAAAACAATTGTTTGTGGAGC
AGCATAAGCATTATTTAGATGAGATTATTGAGCAAATCAGTGAATTTTCTAAGCGTGTTATTTTAGCAGATGCCAATTT
AGATAAAGTTCTTAGTGCATATAACAAACATAGAGACAAACCAATACGTGAACAAGCAGAAAATATTATTCATTTATTT
ACGTTGACGAATCTTGGAGCTCCCGCTGCTTTTAAATATTTTGATACAACAATTGATCGTAAACGATATACGTCTACAA
AAGAAGTTTTAGATGCCACTCTTATCCATCAATCCATCACTGGTCTTTATGAAACACGCATTGATTTGAGTCAGCTAGG
AGGTGACTGA (SEQ ID NO:5)

MODULATING HUMAN Cas9-SPECIFIC HOST IMMUNE RESPONSE

CROSS-REFERENCE TO RELATED APPLICATIONS

This application is a divisional application of U.S. application Ser. No. 17/546,810, filed Dec. 9, 2021, which is a divisional application of U.S. application Ser. No. 16/632,782, filed Jan. 21, 2020, which issued as U.S. Pat. No. 11,208,640 on Dec. 28, 2021, which represents the national stage entry of PCT International Application No. PCT/US2018/029937, filed on Apr. 27, 2018, which claims the benefit of U.S. Provisional Application Nos. 62/535,516, filed Jul. 21, 2017, and 62/556,061, filed Sep. 8, 2017, each of which is incorporated herein by reference in its entirety.

REFERENCE TO AN ELECTRONIC SEQUENCE LISTING

The contents of the electronic sequence listing (112624.01462.xml; Size: 124,165 bytes; and Date of Creation: Jul. 19, 2024) is herein incorporated by reference in its entirety.

BACKGROUND

The CRISPR/Cas9 gene-editing tool is currently in clinical trials as the excitement about its therapeutic potential is exponentially growing. Being a bacterial protein, Cas9 is likely to trigger cellular and humoral immune reaction in humans, as has been recently demonstrated in naïve mice. The potential consequences of this immune response include neutralization of the gene product; destruction of the cells expressing it leading to loss of therapeutic activity or tissue destruction; memory effect that prevents re-administration; and violent innate inflammatory response.

Cas9-specific T cell activation and proliferation were confirmed in an expanded CD45+ cell population following in vivo expression of Cas9 delivered by an AAV vector or DNA electroporation in mice. These data highlight the need to characterize the immunogenicity of Cas9 in humans as this gene-editing technology is moving to the clinic. Accordingly, there remains a need for strategies for decreasing the immunogenicity of CRISPR/Cas9 system components and improving the safety of CRISPR-based gene therapies for human subjects.

SUMMARY

Provided herein are methods and compositions for decreasing an undesired T cell immune response in human subjects undergoing gene therapy using a CRISPR/Cas9 system.

In a first aspect, provided herein is a method of identifying and treating a subject at risk of having a Cas9 antigen-specific CD8+ T cell immune response. The method can comprise or consist essentially of (a) detecting one or more immunodominant Cas9 epitopes in a biological sample obtained from the subject, wherein the detection of the one or more immunodominant Cas9 epitopes identifies the subject as having pre-existing immunity to Cas9; and (b) treating the subject identified in (a) with CRISPR/Cas9-based gene therapy, wherein treating comprises introducing into a cell from the identified subject an engineered, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises a mutation selected from the group consisting of L241G, L616G, and L241G/L616G with reference to the position numbering of a *Streptococcus pyogenes* Cas9 protein (SEQ ID NO:1), whereby expression of the at least one gene product is altered and a disease associated with the gene product is treated. The introducing step can be performed ex vivo or in vivo.

In another aspect, provided herein is a method of reducing an undesired Cas9-specific CD8+ T cell immune response in a subject who will receive CRISPR/Cas9-based gene therapy. The method can comprise or consist essentially of the method introducing into a cell from a subject identified as having pre-existing immunity to Cas9 an engineered, programmable, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises a mutation selected from the group consisting of L241G, L616G, and L241G/L616G as numbered relative to SEQ ID NO:1, whereby expression of the at least one gene product is altered and whereby a Cas9-specific CD8+ T cell immune response is reduced relative to that produced by a cell comprising a naturally occurring Cas9 or an engineered, programmable, non-naturally occurring Type II CRISPR-Cas system wherein the Cas9 protein does not comprise the mutation. The introducing step can be performed ex vivo or in vivo.

In another aspect, provided herein is a variant Cas9 protein encoded by the amino acid sequence of SEQ ID NO:2, a variant Cas9 protein encoded by the amino acid sequence of SEQ ID NO:3, and a variant Cas9 protein encoded by the amino acid sequence of SEQ ID NO:4.

In a further aspect, provided herein is an isolated polynucleotide encoding a variant Cas9 polypeptide, a vector comprising such a polynucleotide, and a host cell comprising such a vector.

In another aspect, provided herein is a method of making a variant of a Cas9 polypeptide shown in SEQ ID NO:1. The method can comprise or consist essentially of using a polynucleotide mutagenesis procedure to generate a population of mutants of the Cas9 polynucleotide shown in SEQ ID NO:5, wherein the population of mutant Cas9 polynucleotides encodes Cas9 polypeptide variants having at least one amino acid substitution selected from the group consisting of L241G and L616G as numbered relative to SEQ ID NO:1; and expressing a population of Cas9 polypeptide variants encoded by the population of Cas9 polynucleotide mutants; so that a variant of a Cas9 polypeptide shown in SEQ ID NO:1 is made. The method can further comprise screening one or more members of the population of Cas9 polypeptide variants so as to identify a variant that exhibits a decreased immunogenicity as compared to the Cas9 polypeptide shown in SEQ ID NO:1 but retains cleavage and/or binding activity relative to the activity of a Cas9 polypeptide without the at least one amino acid substitution.

In a further aspect, provided herein is a variant Cas9 protein made by the method described above, wherein the variant Cas9 protein is encoded by an amino acid sequence selected from the group consisting of SEQ ID NO:2, SEQ ID NO:3, and SEQ ID NO:4.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein:

FIGS. 7A-7J demonstrate pCas9 immunodominant epitope-specific CD8+ T cell recognition is abolished after anchor residue mutation while the mutated SpCas9 protein retains its function and specificity. (A) Epitope β-specific CD8+ T cell response detected using β-specific pentamer in PBMCs stimulated with peptide β-pulsed antigen presenting cells. (B) The percentage of CD8+ β-pentamer+ T cells was reduced to 0.3% when APCs were pulsed with the mutated peptide β2. (C) Sequences of epitopes α and β before and after mutation of the anchor (2nd and/or 9th) residues. Sb, normalized binding score; Si, normalized immunogenicity score. (D) IFN-γ ELISpot assay in triplicate wells comparing T cell reactivity to wild type or mutated epitopes α and β. These results are representative of 12 donors and two independent replicates. (E) Schematic of the experiment assessing mutagenesis capacity of Cas9-β2. Cells were transfected with either WT-Cas9, Cas9-β2, or an empty plasmid as well as 20nt gRNA targeting EMX-1 locus. 72 hr after the transfection, percent cleavage was assessed by DNA extraction and illumine sequencing. (F) Percentage of indel formation in EMX-1 locus. Each individual dot represents an individual transfection. (G) Schematic of the experiment assessing gRNA binding, DNA targeting and transcriptional modulation with Cas9-β2. Cells were transfected with either WT-Cas9, Cas9-β2, or an empty plasmid as well as 14nt gRNA targeting TTN or MIAT in the presence of MS2-P65-HSF1 (transcriptional modulation). 72 hr after the transfection, mRNA was assessed by qRT-PCR. (H and I) Shown is the mRNA level relative to an untransfected control experiment. Each individual dot represents an individual transfection. (J) Mean expression levels of 24,078 protein coding and non-coding RNA genes for WT-Cas9 and Cas9-β2 (each in duplicate) are shown. For visualization purposes, the values were transformed to a log 2(CPM+1) scale. MIAT, the gRNA target gene, is highlighted in red, and R denotes Pearson correlation coefficient between two groups.

FIG. 12 is a table presenting Cas9 HLA-A*02:01 epitopes (SEQ ID NOs:24-61 for epitopes ranked 1-38, respectively) predicted using the prediction model described herein and ranked according to their $S_i$–$S_b$ score.

FIG. 13 is an amino acid sequence encoding CRISPR-associated endonuclease Cas9/Csn1 of *Streptococcus pyogenes* (UniProtKB Q99ZW2) (SEQ ID NO:1).

FIG. 14 is a nucleotide sequence encoding CRISPR-associated endonuclease Cas9 of *Streptococcus pyogenes* (NCBI Reference Sequence: NC_002737.2) (SEQ ID NO:5).

Figure 1:
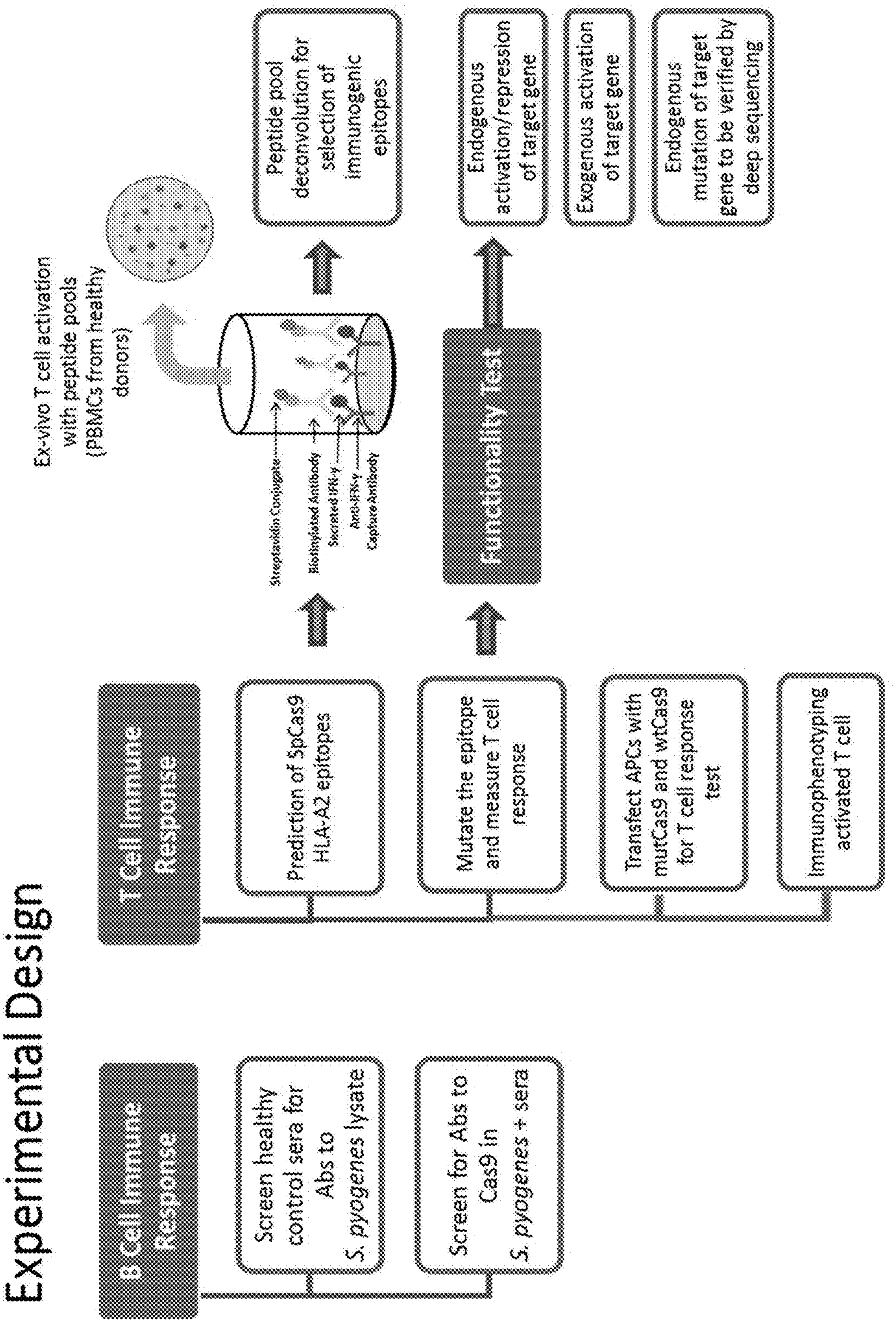
FIG. 1 is a schematic illustrating a workflow for selecting immunogenic epitopes.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

Although the following description refers to certain aspects or embodiments, such aspects or embodiments are illustrative and non-exhaustive in nature. Having reviewed the present disclosure, persons of ordinary skill in the art will readily recognize and appreciate that numerous other possible variations or alternative configurations or aspects are possible and were contemplated within the scope of the present disclosure.

Provided herein are compositions, methods, and systems based at least in part on the inventors' identification of immunodominant T cell epitopes of *Streptococcus pyogenes* Cas9 (SpCas9).

In a first aspect, provided herein is a method of making a genetically modified Cas protein and variant Cas proteins made by such methods. Modifications to a Cas9 protein sequence are made based on immunodominant T cell epitopes of Cas proteins, including wild-type and modified (variant) versions of Cas9. In some embodiments, a Cas9 protein has been genetically modified to remove immunogenically dominant epitopes (also known as "immunodominant epitopes") associated with suboptimal results in clinical gene therapy. As used herein, the term "immunodominant" refers to an epitope capable of stimulating an immune response over other potential epitopes contained within a protein or organism. Deletion or mutation of immunodominant epitopes can potentially decrease the risk of the potentially disruptive immune response in individuals before or during receiving CRISPR/Cas treatment. This method specifically modifies a Cas protein to reduce the risk of the potentially disruptive immune response in individuals (regardless of their HLA type) while preserving its function. In this manner, immunogenic epitopes will be silenced to generate a CRISPR/Cas tool that induces minimal host immune response. As used herein, the term "epitope," also known as an immunogenic epitope or antigenic determinant, refers to the set of amino acid residues that is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor, or Human Leukocyte Antigen (HLA) molecule.

Immunodominance is the observation that in spite of a large number of possible epitopes (antigen fragments) in an antigen, the immune system focuses its response on a limited number of epitopes and can be ordered as a reproducible hierarchy (Sercarz et al. 1993). Immunodominance holds true for immune responses to artificial antigens, human viruses including influenza and vaccinia, and intracellular bacteria (Chen W S 1994, Belze G T et al. 2000, Chen W 2000, Tscharke D C 2005). As used herein, the term "dominant antigen" or "dominant epitope" (also referred to herein as an "immunodominant epitope") refers to an antigen or epitope that evokes a strong tolerance or immune response, which may be characterized by the presence of T cells specific for that antigen or epitope in an amount greater than about 70% of the total number of responding T cells. As used herein, the term "subdominant antigen" or "subdominant epitope" refers to an antigen or epitope that evokes a weaker tolerance or immune response than that of a dominant antigen or epitope.

As used herein, the term "immune response" refers to a response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

In some cases, the method of making a mutant multifunctional Cas9 protein (e.g., having DNA binding activity and nuclease activity) or mutant nuclease-null Cas9 protein comprises identifying one or more immunodominant epitopes among full length amino acid sequences of wild-type and/or modified Cas9 proteins, identifying a nucleic acid sequence for the one or more immunodominant epitopes, generating a nucleic acid sequence for a target Cas9 protein which introduces one or more mutations to disrupt the one or more immunodominant epitopes, and generating a mutant Cas9 protein from the generated nucleic acid sequence.

In certain embodiments, the mutations alter one or more amino acid residues in the amino acid sequence of a target Cas protein. In some cases, the mutation replaces a leucine (L) residue at position 241 with a glycine (G), as numbered relative to the position numbering of a *Streptococcus pyogenes* Cas9 amino acid sequence (SEQ ID NO:1). A Cas9 protein variant comprising L241G is identified herein as Cas9-α2 (SEQ ID NO:2). In other cases, the mutation replaces a leucine (L) residue at position 616 with a glycine (G) as numbered relative to the position numbering of a *Streptococcus pyogenes* Cas9 protein. A Cas9 protein variant comprising a L616G mutation is identified herein as Cas9-β2 (SEQ ID NO:3). In some cases, mutations are generated at both positions, such that the Cas9 protein variant comprises amino acid substitutions at one or both amino acid positions L241 and L616, as numbered relative to the position numbering of a *Streptococcus pyogenes* Cas9 protein. A Cas9 protein variant comprising L241G and L616G mutations is identified herein as Cas9-α2-02 (SEQ ID NO:4). Preferably, the Cas9 variant protein retains its wild-type enzymatic activity (e.g., nuclease, nickase, DNA-binding activity). In some cases, the mutant/modified Cas9 protein is encoded by the amino acid sequence of SEQ ID NO:2. In other cases, the mutant/modified Cas9 protein is encoded by the amino acid sequence of SEQ ID NO:3 or SEQ ID NO:4. Preferably, the mutant Cas9 protein retains DNA binding and nuclease activity but is less likely to trigger an adverse immune response in a subject having pre-existing immunity to Cas9.

In some cases, the wild type Cas protein is *Streptococcus pyogenes* Cas9 (SpCas9). In other cases, the wild type Cas protein is a Cas9 ortholog from another bacterial species such as, for example, *Staphylococcus aureus* and *Streptococcus* thermophiles. SpCas9 is the most extensively studied Cas9 protein but other orthologs are being explored to overcome some of the limitations of SpCas9. These include the large size that leaves little space for packaging additional sequences.

Linear immunogenic epitopes of a Cas9 protein, a modified Cas9 protein, or any portion of the Cas protein to be applied in a CRISPR/Cas system are identified using, without limitation, publicly available algorithms (e.g., Immune Epitope Database and Analysis Resource (IEDB)). Predicted peptides are ranked according to their immunogenicity score and will be synthesized to be used to detect the T cell response.

As used herein, the term "CRISPR/Cas" (Clustered Regularly Interspaced Palindromic Repeats/CRISPR associated) refers to a targeted genome editing system that harnesses sequence-specific nuclease activity of a Cas protein. CRISPR systems belong to different classes, with different repeat patterns, sets of genes, and species ranges.

Immunodominant epitopes can be identified and silenced to generate a CRISPR/Cas tool that induces minimal host immune response. In some cases, identified epitopes are modified by mutation or deletion of the necessary amino acids to abolish MHC binding, or by mutation or deletion of the necessary amino acids to abolish TCR contact residues. In some cases, mutagenesis strategies employ the following steps: (a) designing Cas gene fragments containing the desired mutations; (b) designing PCR primers to amplify regions of a Cas gene that do not contain mutations; (c) performing a recombination-based cloning reaction (e.g., Golden Gate or variant thereof) or a BP reaction (i.e., using a BP clonase enzyme) in order to produce different Cas mutants (e.g., three different SpCas9 mutants; single and double mutations); and (d) performing LR reaction (i.e., using a LR clonase enzyme) to clone the mutated Cas gene in a plasmid containing a promoter and Poly A to be able to express the gene. For review of the recombination based cloning systems, see Festa et al., *Proteomics.* 2013; 13(9): 1381-1399.

To assess Cas9 functionality and off-target effects after modification, nuclease activity of genetically modified Cas9 variants is measured. Cells are transfected with Cas9 mutants and gRNA targeting endogenous or exogenous genes, and on-target CRISPR/Cas9 mutations in cultured cells caused by nuclease function of Cas9 are identified using deep sequencing and/or a surveyor nuclease assay. In other cases, Cas9 target recognition and binding function is achieved by transfecting cells with Modified Cas9s and gRNA targeting endogenous or exogenous genes and activation/repression mediators (e.g., SAM, VP64, p65AD, VPR, KRAB) and measuring the expression of genes. In some cases, off-target activity of WT and modified Cas9 proteins are assessed using next generation sequencing.

Due to natural exposure, pre-existing immunity directed against the vector and less commonly the transgene is a common challenge in gene therapy. Being a bacterial protein, SpCas9 is likely to trigger cellular and humoral immune reaction in humans, as was demonstrated in naïve mice. More alarmingly, the ubiquity of *S. pyogenes* with 700 million infections annually, suggests that pre-existing immunity to SpCas9 in healthy individuals is a reasonable concern. Accordingly, in another aspect, this disclosure provides a method for screening human patients to identify patients more likely to have an adverse immune response to gene therapy using a CRISPR/Cas9 system. In this manner, human patients can be classified as good or poor candidates to receive CRISPR/Cas9-based gene therapy based on the likelihood of the subject having an adverse reaction to one or more components of the CRISPR/Cas9 system. For example, candidate patients can be screened for pre-existing immunity to Cas9. In some cases, pre-existing Cas9 immunity is a predictive biomarker of toxicity or adverse response to CRISPR/Cas9-based gene therapy.

Upon identification of a human patient having pre-existing immunity to Cas9, a genetically modified Cas9 having reduced immunogenicity as described herein could be used in place of an unmodified Cas9 for that patient's CRISPR/Cas9-based gene therapy. In some cases, Cas9 immunogenicity in such a patient can also be limited or reduced by co-expressing molecules associated with immune evasion including, but not limited to, PD-L1, CTLA-4, IL-10, IDO-1, antisense HLA class I, and $\beta_2$M.

In order to identify immunogenic epitopes that can potentially be removed or mutated, peripheral blood mononuclear cells (PBMCs) are collected from individuals who have been infected with specific pathogens, individuals with known autoimmune disorders, healthy individuals, etc. and are exposed to (i) Cas9 protein or any specific fragments of it; (ii) a modified Cas9 protein or any specific fragment of a modified Cas9 protein; or (iii) antigen presenting cells (APCs) expressing Cas9, modified Cas9, a fragment of Cas9, a fragment of modified Cas9, or cells targeted with CRISPR/Cas9 system (in any form) expressing Cas9, modified Cas9, a fragment of Cas9, or a fragment of modified Cas9.

As used herein, the term "antigen presenting cells" or "APCs" refers to cells of the immune system used for presenting antigen to T cells. APCs include dendritic cells, monocytes, macrophages, marginal zone Kupffer cells, microglia, Langerhans cells, T cells, and B cells. Preferably, the APCs are an individual's own APCs (meaning, derived or obtained from the individual) that can be briefly cultured and transduced with genetic material (e.g., lentiviral clones) ex vivo. This is a preferred method because it would enable the clinical study of an individual's own T cell repertoire. In some cases, the APCs are an established cell line that acts as an APC and has a human leukocyte antigen (HLA) type that matches the T cells. With established cell lines, it may be possible to maintain a population of cells already programmed with a wide variety of antigens that can be used in repeated experiments. In other cases, the APCs are an established APC cell line that displays a highly common HLA type; an established APC cell line that is programmed to display an HLA type that matches the T cells; an established APC cell line that has been engineered to produce a detectable marker protein (e.g., eGFP, mCherry, luciferase, etc.) upon induction by an activated T cell, an established APC cell line that has been engineered to produce any other detectable signal when induced by an activated T cell; or APCs into which a reporter gene construct is introduced simultaneously with the cDNA. This reporter gene construct would be triggered to signal if the APC is induced to mature after T cell activation.

APCs comprising particular gene constructs can be obtained by cDNA delivery. Preferably, cDNA is introduced into a cell in a form that supports protein expression. The cDNA could be a gene encoding Cas9 from any organism, a library encoding fragments of Cas9 protein that include potentially immunogenic peptides (to map specific epitopes), a gene encoding a modified version of Cas9, or a sequence encoding fragments of Cas9 or Modified Cas9 to investigate which epitope(s) induces a T cell response. cDNA can be introduced into the cells using any appropriate method including, without limitation, lentivirus transduction, retrovirus transduction, other viral delivery systems, electroporation or nucleoporation, delivery of RNA, chemical transfection, or delivery of an exogenous protein or proteins traceable to the library.

To perform the screening method, a population of T cells (e.g., experimentally produced cells or cells from individuals who have been infected with specific pathogens, individuals with known autoimmune disorders, healthy individuals, etc.) is mixed with a portion of Cas9 protein as an antigen. Activated T cells will be measured as an indication of epitope recognition by T cells (effector T cells, cytotoxic T cells, helper T cells, memory T cells, natural killer T cells, or regulatory T cells). T cell activation can be measured using any appropriate method including, without limitation, methods for measuring T cell proliferation (e.g., limiting dilutions culture); cytokine secretion (e.g., ELISPOT, intracellular staining); cytokine capture (e.g. Miltenyi Biotec commercial IFN-7 secretion assay); tetramer (or any MHC-multimer) staining; spectratyping and biosensor assays to detect specific CDR3 of T cell populations of interest; and immunophenotyping of activated T cells (e.g., CD25, CD69, CD137, CD107).

In another aspect, provided herein is a method of identifying and treating a subject at risk of having a Cas9 antigen-specific CD8+ T cell immune response. In some cases, the method comprises (a) detecting one or more immunodominant Cas9 epitopes in a biological sample obtained from the subject, wherein the detection of the one or more immunodominant Cas9 epitopes identifies the subject as having pre-existing immunity to Cas9; (b) treating the subject identified in (a) with CRISPR/Cas9-based gene therapy, wherein treating comprises introducing into a cell from the identified subject an engineered, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises one or more mutations selected from the group consisting of L241G and L616G (including double mutant L241G/L616G) with reference to the position numbering of a *Streptococcus pyogenes* Cas9 protein (SEQ ID NO:1), whereby expression of the at least one gene product is altered and a disease associated with the gene product is treated. Exemplary immunodominant Cas9 epitopes are shown in Table 3. As used herein, the term "identifying" refers to any action or set of actions that allows a clinician to recognize a subject as one who may benefit from the methods and compositions provided herein. Preferably, the identified subject is one who is in need of a tolerogenic antigen-specific (e.g., Cas9-specific) immune response prior to or during CRISPR/Cas-based gene therapy as provided herein.

As used herein, the term "antigen-specific" refers to any immune response that results from the presence of the antigen, or portion thereof, or that generates molecules that specifically recognize or bind the antigen. For example, where the immune response is antigen-specific antibody production, antibodies are produced that specifically bind the antigen. As another example, where the immune response is antigen-specific CD8+ T cell proliferation and/or activity, the proliferation and/or activity can result from recognition of the antigen, or portion thereof, alone or in complex with MHC molecules. In some cases, the antigen-specific immune response is a Cas9-specific immune response.

For the methods provided herein, foreign nucleic acids (i.e., those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. As used herein, the term "undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health. Undesired immune responses include Cas9 antigen-specific CD8+ T cell proliferation and/or activity. Desired immune responses, therefore, include the inhibition in the stimulation or activation of CD8+ T cells, the inhibition of CD8+ T cell proliferation, the inhibition of the production of cytokines by CD8+ T cells, etc. Methods for testing these immune responses are provided herein or are otherwise known to those of ordinary skill in the art.

In another aspect, provided herein is a method of reducing an undesired Cas9-specific CD8+ T cell immune response in a subject who will receive CRISPR/Cas9-based gene therapy. In certain embodiments, the method comprises introducing into a cell from a subject identified as having pre-existing immunity to Cas9 an engineered, programmable, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises one or more amino acid substitutions selected from the group consisting of L241G, L616G, and L241G/L616G as numbered relative to SEQ ID NO:1, whereby expression of the at least one gene product is altered and whereby a Cas9-specific CD8+ T cell immune response is reduced relative to that produced by a cell comprising a naturally occurring Cas9 protein, a synthetic wild-type Cas9 protein, or an engineered non-naturally occurring Type II CRISPR/Cas system wherein the Cas9 protein does not comprise the mutation. The introducing step can be performed ex vivo or in vivo.

In a further aspect, provided herein is a method of generating a variant Cas9 protein, where the Cas9 variant is less immunogenic when expressed in a human cell yet retains its DNA binding/targeting capacity and its capacity for transcriptional activation or repression. For example, a variant Cas9 generated according to a method described herein retains its capacity to modulate transcription of endogenous genes and reporter genes (e.g., TTN, MIAT genes). In certain embodiments, a variant Cas9 protein made by a method provided herein is less immunogenic relative to a non-variant Cas9 protein when expressed in a human cell yet retains its DNA cleavage activity. In some cases, the method comprises using a polynucleotide mutagenesis procedure to generate a population of mutants of the Cas9 polynucleotide shown in SEQ ID NO:5, wherein the population of mutant Cas9 polynucleotides encodes Cas9 polypeptide variants having at least one amino acid substitution selected from the group consisting of L241G and L616G as numbered relative to SEQ ID NO:1; and expressing a population of Cas9 polypeptide variants encoded by the population of Cas9 polynucleotide mutants; so that a variant of a Cas9 polypeptide shown in SEQ ID NO:1 is made.

In some cases, the method further comprises screening members of a population of Cas9 polypeptide variants so as to identify a variant that exhibits a decreased immunogenicity when expressed in a human cell as compared to the Cas9 polypeptide shown in SEQ ID NO:1 but retains cleavage and/or binding activity relative to the activity of a Cas9 polypeptide without the at least one amino acid substitution.

Illustrative methods of mutagenesis protocols are shown, for example, in the following Examples. In addition, a wide variety of techniques for generating variant polynucleotides and polypeptides have been well known in the art for many years, for example site-directed mutagenesis (see, e.g. Carter et al., 1986, *Nucl. Acids Res.* 13:4331; Zoller et al., 1987, *Nucl. Acids Res.* 10:6487), In another aspect, provided herein is a variant Cas9 protein made by a method provided herein. Typically, the substitution variant exhibits one or more altered properties as compared to the Cas9 polypeptide shown in SEQ ID NO:1, for example, a decreased immunogenicity.

Embodiments of this disclosure also include polynucleotides encoding the Cas9 variants disclosed herein, for example an isolated polynucleotide having at least a 90%-100% sequence identity to a polynucleotide encoding a variant Cas9 polypeptide as disclosed herein. In some cases, a polynucleotide encoding a variant Cas9 polypeptide as disclosed herein is in a vector. In some cases, the vector is in a host cell (e.g., a bacterial cell, a human cell, or other eukaryotic cell).

A nucleic acid sequence encoding the desired variant Cas9 polypeptide once isolated or synthesized, can be cloned into any suitable expression vector using convenient restriction sites. Expression vectors usually include an origin of replication, a promoter, a translation initiation site, optionally a signal peptide, a polyadenylation site, and a transcription termination site. These vectors also usually contain an antibiotic marker gene for selection. Suitable expression vectors may be plasmids, cosmids, or viruses including retroviruses. The coding sequence for the polypeptide is placed under the control of an appropriate promoter, control elements and a transcriptional terminator so that the DNA sequence encoding the polypeptide is transcribed into RNA in the host cell transformed by the expression vector construct. The coding sequence may or may not contain a signal peptide or leader sequence for secretion of the polypeptide out of the host cell. Numerous expression vectors and systems are known, both for prokaryotes and eukaryotes, and the selection of an appropriate system is a matter of choice. Expression and purification of the polyprotein product of the invention can be easily performed by one skilled in the art. See, Sambrook et al., "Molecular cloning-A Laboratory Manual, second edition."

The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

So that the methods and compositions provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including alignment algorithms such as BLAST (available on the World Wide Web at ncbi.nlm.nih.gov/BLAST) and FASTA (available in the Genetics Computing Group (GCG) package).

As used herein, a "coding sequence" can be a sequence which "encodes" a particular gene, such as a Cas9 gene, for example. A coding sequence is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence will usually be located 3' to the coding sequence.

As used herein, the term "operably linked" refers to an arrangement of elements wherein the components so described are configured so as to perform their usual function. Thus, control sequences (e.g., promoter sequences, ribosome binding sites, polyadenylation signals, transcription termination sequences, upstream regulatory domains, enhancers, and the like) operably linked to a coding sequence are capable of effecting the expression of the coding sequence. The control sequences need not be contiguous with the coding sequence, so long as they function to direct the expression thereof.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

Examples

Presented in this example are experiments demonstrating that immunodominant Cas9 epitopes can be mutated to reduce immunogenicity in human cells without loss of Cas9 DNA binding or nuclease activity.

Materials & Methods

Detection of Cas9-Specific Serum Antibodies in Healthy Controls: Healthy control sera (n=183) used in this study, and previously described (Anderson et al., Oral oncology 51:662-667 (2015)), are a subset of a molecular epidemiology study of head and neck cancer at the MD Anderson Cancer Center, collected between January 2006 and September 2008. *S. pyogenes* lysate was prepared by sonication of bacterial pellets from overnight cultures of *S. pyogenes* ATCC 19615 in the presence of 1 pill of complete Protease Inhibitor (Sigma-Aldrich) after 3 cycles of freezing and thawing. Serum antibody detection was performed using ELISA. 96-well plates were coated with 20 μg/mL of recombinant *S. pyogenes* Cas9 nuclease (New England Biolabs, Ipswich, MA) or *S. pyogenes* lysate. Sera were diluted 1:50 in 10% *E. coli* lysate prepared in 5% milk-PBST (0.2% tween) (Wang et al., *Proteomics Clin Appl* 7:378-383 (2013)), incubated with shaking for 2 hours at room temperature, and added to the specified wells in duplicate. Horseradish peroxidase (HRP) anti-human IgG Abs (Jackson ImmunoResearch Laboratories, West Grove, PA) were added at 1:10,000, and detected using Supersignal ELISA Femto Chemiluminescent substrate (Thermo Fisher Scientific, Waltham, MA). Luminescence was detected as relative light units (RLU) on a Glomax 96 Microplate Luminometer (Promega, Madison, WI) at 425 nm. To establish cut-off values, a RLU ratio>(the mean+3 standard deviations) of 125 randomly chosen control samples was designated positive (FIG. 2, dotted and dashed lines for bacterial lysate and Cas9 protein, respectively).

Cas9 candidate T cell epitope prediction: Previously described prediction strategies were used to predict candidate Cas9 T cell epitopes. Briefly, we predicted MHC class I restricted 9-mer and 10-mer candidate epitopes derived from the Cas9 protein (Uniprot—Q99ZW2) for HLA A*02:01. The protein reference sequence was entered into 5 different prediction algorithms; 3 MHC-binding: IEDB-consensus binding (Moutaftsi et al., *Nature biotechnology* 24:817 (2006)), NetMHCpan binding (Hoof et al., *Immunogenetics* 61:1 (2009)), Syfpeithi (Rammensee et al., *Immunogenetics* 50:213-219 (1999)), and 2 antigen-processing algorithms: IEDBconsensus processing, ANN processing (Tenzer et al., *Cellular and Molecular Life Sciences* 62, 1025-1037 (2005)). The individual scores from each of the prediction algorithms were then normalized within the pool of predicted peptides after exclusion of poor binders as previously detailed (Chowell et al., *Proc Natl Acad Sci USA* 112:E1754-1762 (2015); Krishna & Anderson, *Vaccine Design: Methods and Protocols: Volume* 1: *Vaccines for Human Diseases,* 779-796 (2016)), and the average normalized binding scores were used to rerank the candidate peptides. The top 38 candidate peptides (Table 3) were selected for experimental testing. The IEDB consensus MHC-binding prediction algorithm (available at iedb.org on the World Wide Web) was applied to obtain a list of high binding Cas9 peptides, each of which was assigned a normalized binding score (Sb). The immunogenicity score (Si) was calculated for each peptide based on its amino acid hydrophobicity (ANN-Hydro) (Chowell, D. et al., *Proc Natl Acad Sci USA* 112:E1754-1762 (2015)).

Ex vivo stimulation and epitope mapping of Cas9 by ELISpot: All peripheral blood mononuclear cells (PBMCs) were obtained from healthy individuals with written informed consent under ASU's Institutional Review Board. PBMCs were isolated from fresh heparinized blood by Ficoll-Hypaque (GE Healthcare, UK) density gradient centrifugation and stimulated as previously described (Krishna & Anderson, *Vaccine Design: Methods and Protocols: Volume* 1: *Vaccines for Human Diseases,* 779-796 (2016)). Briefly, predicted Cas9 peptides with Sb<0.148 (N=38) were synthesized (>80% purity) by Proimmune, UK. Each peptide was reconstituted at 1 mg/mL in sterile PBS and pools were created by mixing 3-4 candidate peptides. Sterile multiscreen ELISpot plates (Merck Millipore, Billerica, MA, USA) were coated overnight with 5 g/well of anti-IFN-7 capture antibody (clone D1K, Mabtech, USA) diluted in sterile PBS. Frozen PBMCs were thawed rapidly and recombinant human IL-2 (20 U/mL, R&D Systems) was added. They were then stimulated in triplicates with 10 μg/mL Cas9 peptide pools (or individual peptides), premixed CEF pool as a positive control (ProImmune, UK), or DMSO as a negative control in the anti-IFN-7-coated ELISpot plates, (Merck Millipore, Billerica, MA, USA) and incubated in a 37° C., 5% $CO_2$ incubator for 48 hours. Plates were washed three times for 5 min each with ELISpot buffer (PBS+0.5% FBS) and incubated with 1 μg/mL anti-IFN-7 secondary detection antibody (clone 7-B6-1, Mabtech, USA) for 2 hrs at room temperature, washed and incubated with 1 μg/mL Streptavidin ALP conjugate for 1 hour at room temperature. The wells were washed again with ELISpot buffer and spots were developed by incubating for 8-10 min with detection buffer (33 μL NBT, 16.5 μL BCIP, in 100 mM Tris-HCl pH 9, 1 mM $MgCl_2$, 150 mM NaCl). Plates were left to dry for 2 days and spots were read using the AID ELISpot reader (Autoimmun Diagnostika GmbH, Germany). The average number of spot forming units for each triplicate was calculated for each test peptide or peptide pool and subtracted from the background signal.

Autologous APC generation from healthy individual PBMCs: Autologous CD40L-activated B cell APCs were generated from healthy donors by incubating whole PBMCs with irradiated (32 Gy) K562-cell line expressing human CD40L (KCD40L) at a ratio of 4:1 (800,000 PBMCs to 200,000 irradiated KCD40Ls) in each well. The cells were maintained in B cell media (BCM) consisting of IMDM (Gibco, USA), 10% heat-inactivated human serum (Gemini Bio Products, CA, USA), and Antibiotic-Antimycotic (Anti-Anti, Gibco, USA). BCM was supplemented with 10 ng/mL recombinant human IL-4 (R&D Systems, MN, USA), 2 μg/mL Cyclosporin A (Sigma-Aldrich, CA, USA), and insulin transferrin supplement (ITES, Lonza, MD, USA). APCs were re-stimulated with fresh irradiated KCD40Ls on days 5 and 10, after washing with PBS and expanding into a whole 24-well plate. After two weeks, APC purity was assessed by CD19+ CD86+ expressing cells using flow cytometry, and were used for T cell stimulation after >90% purity. APCs were either restimulated up to 4 weeks or cryopreserved for re-expansion as necessary.

T cell stimulation by autologous APCs: Antigen-specific T cells were generated by stimulating healthy donor B cell APCs by peptide pulsing of specific Cas9 epitopes. Peptide pulsing of APCs was done under BCM 5% human serum, with recombinant IL-4. Twenty-four hours later, on day 1, APCs were washed and incubated with thawed whole PBMCs at a ratio of 1:2 (200,000 APCs:400,000 PBMCs) in a 24-well plate in BCM supplemented with 20 U/mL recombinant human IL-2 (R&D Systems, MN, USA) and 5 ng/mL IL-7 (R&D Systems, MN, USA). On day 5, partial media exchange was performed by replacing half the well with fresh BCM and IL-2. On day 10, fresh APCs were peptide pulsed in a new 24-well plate. On day 11, expanded T cells were restimulated with peptide-pulsed APCs similar to day 1. T cells were used for T cell assays or immunophenotyped after day 18.

Flow cytometry staining for T cells: Cells were washed once in MACS buffer (containing PBS, 1% BSA, 0.5 mM EDTA), centrifuged at 550 g for 5 min and re-suspended in 200 μL MACS buffer. Cells were stained in 100 μL of staining buffer containing anti-CD137, conjugated with phycoerythrin (PE, clone 4B4-1; BD Biosciences, USA), anti-CD8-PC5 (clone B9.11; Beckman Coulter 1:100), anti-CD4 (clone SK3; BioLegend, 1:200), anti-CD14 (clone 63D3; BioLegend, 1:200), and anti-CD19 (clone HIB19; BioLegend, 1:200), all conjugated to Fluorescein isothiocyanate (FITC) for exclusion gates, for 30 min on ice. Samples were covered and incubated for 30 min on ice, washed twice in PBS, and resuspended in 1 mL PBS prior to analysis. Measurements were performed using an Attune Acoustic Focusing Cytometer. Lymphocytes were first identified by forward (FSC) and side scatter (SSC) gating. CD4/CD14/CD19/CD56-negative cells (bin gate) were selected, and activated Pentamer+ (or CD137+) T cells were identified within the CD8+ gate. Analysis was performed using Attune Cytometric Software V2.1.

Pentamer staining for T cell immunophenotyping: The following HLA-A*02:01 PE-conjugated Cas9 pentamers were obtained from ProImmune: F2A-D-CUS-A*02:01-ILE DIV ITL-Pentamer, F2A-D-CUJS-A*02:01-NLIALSLGL-Pentamer, 007-Influenza A MP 58-66-GILGFVFTL-Pentamer. T cells were washed twice in MACS buffer with 5% human serum and centrifuged at 550 g for 5 min each time. They were then re-suspended in 100 μL staining buffer (MACS buffer, with 5% human serum and 1 mM Dasatanib (ThermoFisher Scientific, MA, USA). Each of the pentamers was added to resuspended T cells, stimulated with the respective peptide or APCs at a concentration of 1:100. Samples were incubated at room temperature for 30 min in the dark, then washed twice in MACS buffer. Cells were stained in 100 μL MACS buffer with anti-CD8-PC5, anti-CD4-FITC, anti-CD14-FITC, and anti-CD19-FITC for exclusion gates, Samples were then washed twice with PBS and analyzed by flow cytometry. For flow cytometric analysis, all samples were acquired with Attune flow cytometer (ThermoFisher Scientific, MA, USA) and analyzed using the Attune software. Gates for expression of different markers and pentamers were determined based on flow minus one (FMO) samples for each color after doublet discrimination. Percentages from each of the gated populations were used for the analysis.

Vector Design and Construction:

Modified Cas9 plasmids—Human codon-optimized *Streptococcus pyogenes* Cas9 sequence was amplified from pSpCas9 (pX330; Addgene plasmid ID: 42230), using forward and reverse primers and inserted within gateway entry vectors using golden gate reaction. Desired mutations were designed within gBlocks (Integrated DNA Technologies). The gblocks and amplicons were then cloned into entry vectors using golden gate reaction. All the primers and gblocks sequences are listed in supplementary notes. Next, the Cas9 vectors and CAG promoter cassettes were cloned into an appropriate gateway destination vector via LR reaction (Invitrogen).

U6-sgRNA-MS2 plasmids—These plasmids were constructed by inserting either 14-bp or 20-bp spacers of gRNAs into sgRNA (MS2) cloning backbone (Addgene plasmid ID: 61424) at BbsI site. gRNA sequences are listed in Table 1.

TABLE 1

| Sequences of gRNAs | |
|---|---|
| MIAT-14bp gRNA | GAGGCTGAGCGCAC (SEQ ID NO: 9) |
| TTN-14bp gRNA | GGAAGTCTCCTTTG (SEQ ID NO: 10) |
| Reporter2-20bp gRNA | GTCCCCTCCACCCCACAGTG (SEQ ID NO: 11) |
| CR10-14bp-gRNA | GCATCAGGAACATGT (SEQ ID NO: 12) |
| EMX1-20bp gRNA | CACC GAGTCCGAGCAGAAGAAGAA (SEQ ID NO: 13) |

Cell culture for endogenous target mutation and activation: HEK293FT cell line was purchased from ATCC and maintained in Dulbecco's modified Eagle's medium (DMEM—Life Technologies) containing 10% fetal bovine serum (FBS—Life Technologies), 2 mM glutamine, 1.0 mM sodium pyruvate (Life Technologies) and 1% penicillinstreptomycin (Life Technologies) in incubators at 37° C. and 5% $CO_2$. Polyethylenimine (PEI) was used to transfect HEK293FT cells seeded into 24-well plates. Transfection complexes were prepared according to manufacturer's instructions.

Figure 11A:
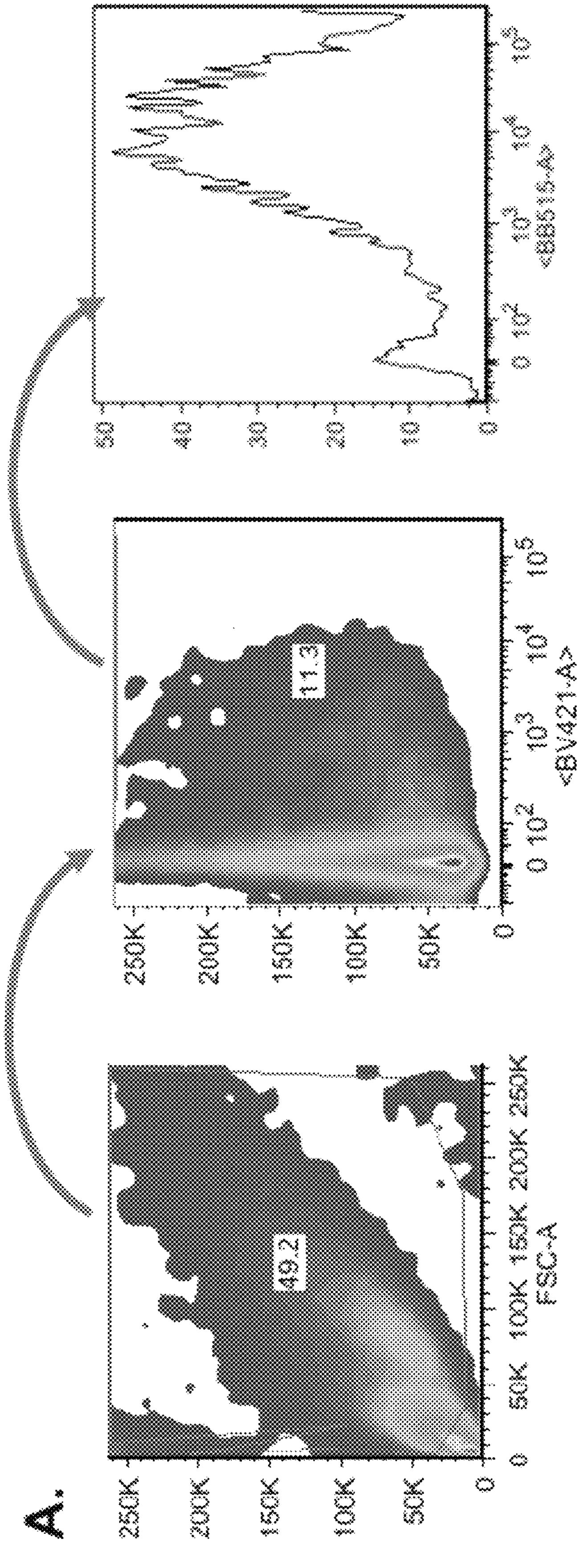
FIGS. 11A-11B. (A) Representative flow cytometry gating for analysis of Cas9 function on synthetic promoters. Cells are gated based on Forward (FSC) and Side Scatter (SSCs). Transfected population then was gated based on expression of EBFP (BV421-A) more than 2×10^2. The geometric mean of the output (EYFP) or iRFP was determined in this population. The BB515-A graph (far right) shows EYFP expression in cells expressing >$2\times10^2$ A.U of the transfection marker (BV421). (B) Flow cytometry gating for analysis of Cas9 pentamer+CD8+ T lymphocytes. Cells were gated based on FSC and SSC and negatively gated on CD4/CD14/CD19/CD56. The CD8−, CD8+, and Cas9 pentamer+ population are shown (bottom right).
Figure 11B:
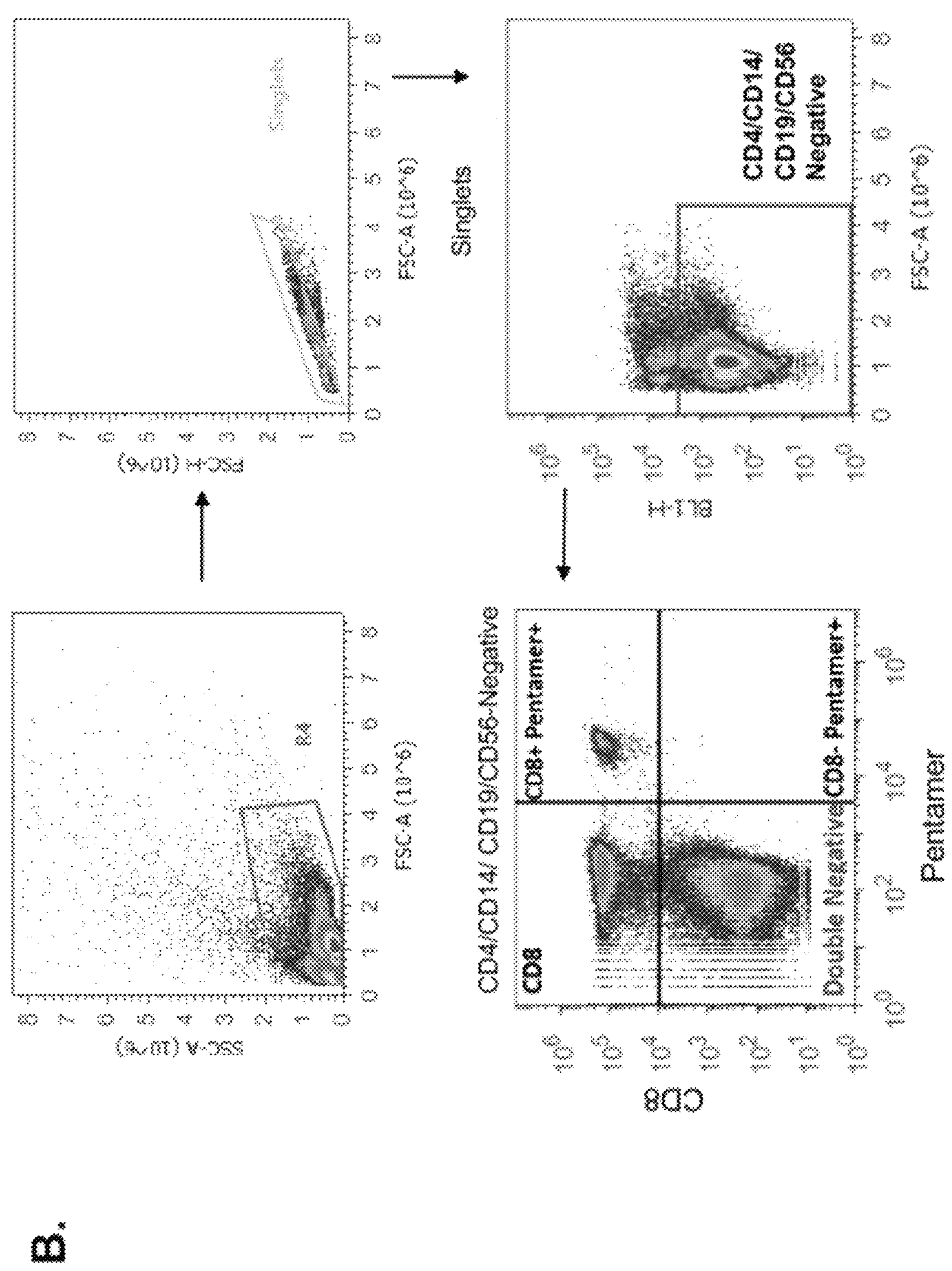

Flow cytometry for Quantifying Cas9 Function: HEK293FT cells were co-transfected with 10 ng gRNA, 200 ng Cas9 constructs, 100 ng reporter plasmid and 25 ng EBFP2 expressing plasmid as the transfection control. Flow cytometry data were collected 48 h after transfection. Cells were trypsinized and centrifuged at 500 g for 5 min at 4° C. The supernatant was then removed, and the cells were resuspended in Hank's Balanced Salt Solution without calcium or magnesium supplemented with 2.5% FBS. BD Celesta was used to obtain flow cytometry measurements in synthetic gene circuits with the following settings: EBFP, measured with a 405 nm laser and a 407/421 filter; EYFP, measured with a 488 nm laser and a 490/515 filter; iRFP, measured with a 640 nm laser and a 50/785 filter. At least 200,000 events were gathered from each sample. Flow cytometry data was analyzed using FlowJo software. Briefly, cells expressing more than $>2\times10^2$ A.U of EBFP (transfection marker) were gated after gating the cells based on FSC and SSC (to exclude debris) and the geometric mean of EYFP was calculated. A sample was excluded if there were less than 300 events in the gated population. A representative flow cytometry gating is depicted in FIG. 11B.

Quantitative RT-PCR Analysis: HEK293FT cells were co-transfected with 10 ng gRNA, 200 ng Cas9 constructs, 100 ng MS2-P65-HSF1 (Addgene plasmid ID: 61423) and 25 ng transfection control. Cells were lysed, and RNA was extracted using RNeasy Plus mini kit (Qiagen) 72 hours post transfection, followed by cDNA synthesis using the High-Capacity RNA-to-cDNA Kit (Thermo fisher). qRT-PCR was performed using SYBR Green PCR Master Mix (Thermo fisher) using a QuantStudio 3 by Applied Biosystems. All analyses were normalized to 18s rRNA (ΔCt) and fold-changes were calculated against un-transfected controls (2-ΔΔCt). Primer sequences for qPCR are listed in Table 2.

TABLE 2

| Sequences of primers | |
|---|---|
| Cas9 fragment 1-FW | ttttGGTCTCTAGGTCCACCATGGACTATAAGGACCACGA (SEQ ID NO: 14) |
| Cas9 fragment1-RV | tttggtctcaGAACAGCTGGTTGTAGGTCTGCA (SEQ ID NO: 15) |
| Cas9 fragment2-FW | ttttGGTCTCTACCAACCGGAAAGTGACCGTGAAG (SEQ ID NO: 16) |
| Cas9 fragment2-RV | ttttGGTCTCAAAGCTTACTTTTTCTTTTTTGCC (SEQ ID NO: 17) |
| qPCRMIAT-FW | TGGCTGGGGTTTGAACCTTT (SEQ ID NO: 18) |
| qPCR-MIAT RV | AGGAAGCTGTTCCAGACTGC (SEQ ID NO: 19) |
| qPCRTTN FW | TGTTGCCACTGGTGCTAAAG (SEQ ID NO: 20) |
| qPCR-TTN-RV | ACAGCAGTCTTCTCCGCTTC (SEQ ID NO: 21) |
| PCR-EMX1-FW | CCATCCCCTTCTGTGAATGT (SEQ ID NO: 22) |
| PCR-EMX1-RV | GGAGATTGGAGACACGGAGA (SEQ ID NO: 23) |

Endogenous Indel Analysis: HEK293FT cells were co-transfected with 200 ng of Cas9 plasmids, 10 ng of gRNA coding cassette and 25 ng transfection control. 72 hours later, transfected cells were dissociated and spun down at 200 g for 5 minutes at room temperature. Genomic DNA was extracted using 50 μl of QuickExtract DNA extraction solution (Epicentre) according to the manufacturer's instructions. Genomic DNA was amplified by PCR using primers flanking the targeted region. Illumina Tru-Seq library was created by ligating partial adaptors and a unique barcode to the DNA samples. Next, a small number of PCR cycles were performed to complete the partial adaptors. Equal amounts of each sample were then pooled and sequenced on Illumina Tru-Seq platform with 2×150 run parameters, which yielded approximately 80,000 reads per sample. Sequencing was performed using a 2×150 paired-end (PE) configuration by CCIB DNA Core Facility at Massachusetts General Hospital (Cambridge, MA, USA). The reads were aligned to the target gene reference in *Mus musculus* genome using Geneious software, 9-1-5, To detect the indels (insertions and deletions of nucleic acid sequence at the site of double-strand break), each mutation was evaluated carefully in order to exclude the ones that are caused by sequencing error or any off-target mutation. The variant frequencies (percentage to total) assigned to each read containing indels were summed up, i.e., indel percentage=total number of indel containing reads/total number of reads. The minimum number of analyzed reads per sample was 70,000.

RNA Sequencing for Quantifying Activator Specificity: HEK293FT cells were co-transfected with 10 ng gRNA for MIAT locus, 200 ng Cas9 constructs, 100 ng MS2-P65-HSF1 (Addgene plasmid ID: 61423) and 25 ng transfection control. Total RNA was extracted 72 hours post transfection using RNeasy Plus mini kit (Qiagen) and sent to UCLA TCGB core on dry ice. Ribosomal RNA depletion, and single read library preparation were performed at UCLA core followed by RNA sequencing using NextSeq500. Coverage was 14 million reads per sample. FASTQ files with single-ended 75 bp reads were then aligned to the human GRCh38 reference genome sequence (Ensembl release 90) with STAR 54, and uniquely-mapped read counts (an average of 14.8 million reads per sample) were obtained with Cufflink (Trapnell et al., *Nature Protocols* 7:562-578 (2012)). The read counts for each sample were then normalized for the library size to CPM (counts per million reads) with edgeR (Robinson et al., *Bioinformatics* 26:139-140 (2010)). Custom R scripts were then used to generate plots.

Results

Figure 2:
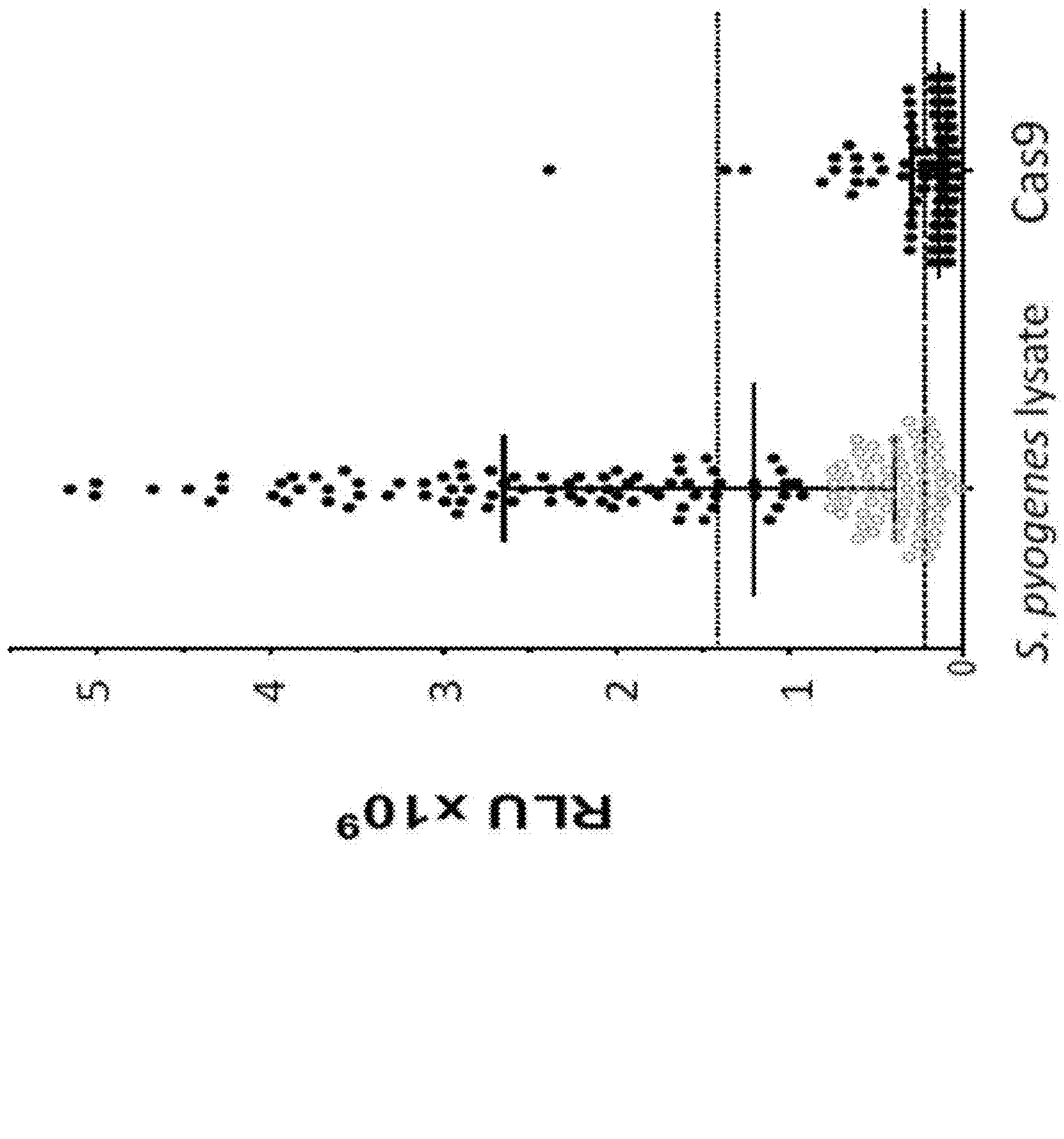
FIG. 2 demonstrates detection of specific serum antibodies (Abs) against *S. pyogenes* lysate in 49.0% (above the dotted line) of 143 healthy controls (left). The subset shown in black circles was screened for Abs against synthetic wild-type Cas9 protein (right), of which 36.6% (21.0% of total samples screened) were positive (above the dashed line). Lines represent median and interquartile range. The mean Relative Light Units (RLU) of positive sera was comparable to the mean RLU detected against the EBNA-1 protein for sera with known EBNA-1 seropositivity.

Detection of Cas9-Specific Serum Antibodies in Healthy Controls: The inventors first investigated whether healthy donors, in particular those with previous exposure to *Streptococcus pyogenes*, have detectable IgG antibodies (Abs) to *Streptococcus pyogenes* Cas9 (SpCas9). Of 143 healthy control sera screened, 49.0% had detectable Abs against *S. pyogenes* lysate as detected using ELISA (FIG. 2). This positive subset (closed circles) along with 12 of the sera negative for *S. pyogenes* lysate that had the highest RLU value were screened for Abs against synthetic wild-type Cas9. At least 21.0% (n=30) of healthy individuals in this study had Cas9-specific Abs (FIG. 2), confirming pre-existing immune response to Cas9.

Figure 3:
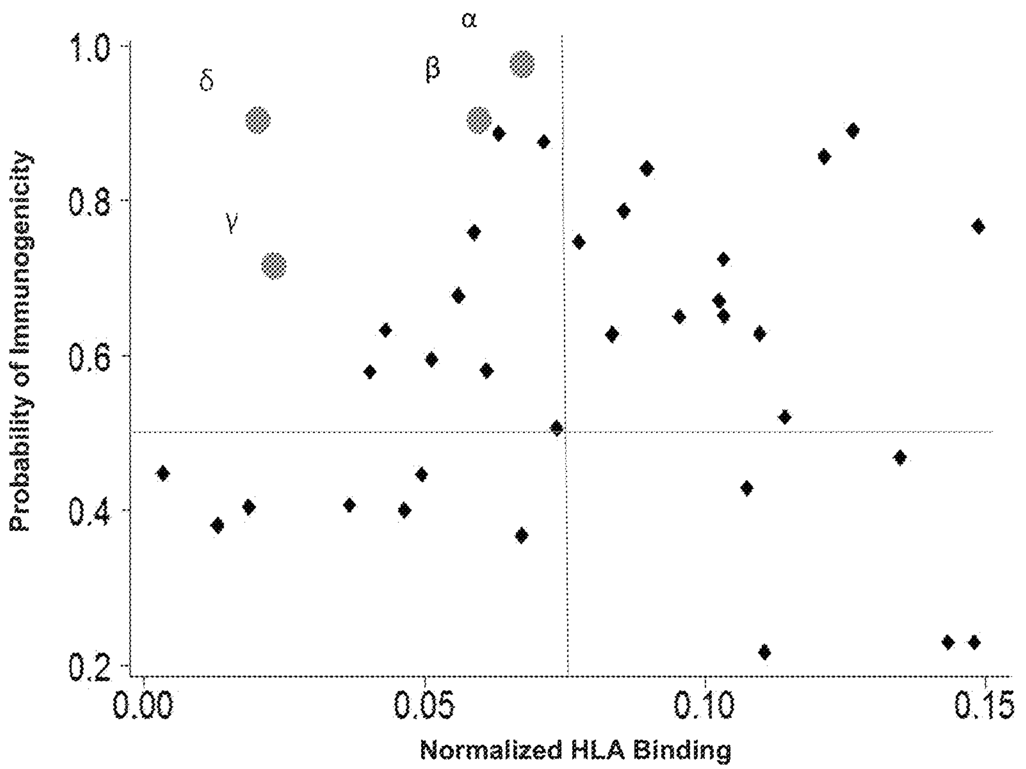
FIG. 3 demonstrates the detection of pre-existing immune response to SpCas9 in healthy donors and identification of two immunodominant T-cell epitopes. The top 5 predicted SpCas9 T cell epitopes and their predicted Sb and Si scores and ranking (based on the Sb.Si value). These top 5 peptides include the identified immunodominant (α and β; gray) and subdominant (γ and δ) epitopes that were shown to be immunogenic by IFN-γ ELISpot. The plot shows Sb and Si of predicted HLA-A*02:01 epitopes for the SpCas9 protein. Red dots represent the immunodominant (α and β) and subdominant (γ and δ) epitopes.

Next, HLA-A*02:01-restricted T cell epitopes derived from SpCas9 were predicted using a model based on both HLA binding and biochemical properties of immunogenicity (Table 3; the top 5 are shown in FIG. 3). Using the inventors' previously reported prediction model (Chowell, D., et al., *Proc Natl Acad Sci USA,* 2015. 112(14):E1754-62), based on a MHC class I binding probability and a peptide immunogenicity probability, Cas9 peptides with predicted high binding and high immunogenicity were prioritized. In brief, IEDB consensus MHC-binding prediction algorithm (available at iedb.org on the World Wide Web) was applied to obtain a list of high binding Cas9 peptides for HLA-A*02:01, each of which was assigned a normalized binding score ($S_b$). Next, an immunogenicity score ($S_i$) was calculated for each peptide based on its amino acid hydrophobicity. According to this prediction model, peptides with low $S_b$ (high binders) and high $S_i$ (more hydrophobic) are expected to be more immunogenic. The calculated normalized binding ($S_b$) and immunogenicity ($S_i$) scores for each peptide (FIG. 3) were plotted to predict the more immunogenic epitopes, which are expected to have both high HLA binding (low $S_b$) and more hydrophobicity (high $S_i$).

TABLE 3

Predicted Cas9 immunogenic T cell epitopes

| | | | SEQ | | Binding | | | Protein Processing | | | | |
|---|---|---|---|---|---|---|---|---|---|---|---|---|
| Rank | Position | Sequence | ID NO: | Code | IEDB | NetMHC | Syfpeithi | IEDB | ANN | $S_b$ | $S_i$ | $S_b \cdot S_i$ |
| **1** | **988-997** | **YLNAVVGTAL** | **24** | γ | **1.25** | **21.5** | **24** | **0.27** | **0.02** | **0.068** | **0.975** | **0.002** |
| 2 | 1281-1290 | ILADANLDKV | 25 | | 1.25 | 11.37 | 31 | −0.06 | −0.49 | 0.003 | 0.447 | 0.002 |
| **3** | **236-244** | **GLFGNLIAL** | **26** | δ | **0.6** | **10.12** | **29** | **1.15** | **1.04** | **0.020** | **0.900** | **0.002** |
| ***4*** | ***240-248*** | ***NLIALSLGL*** | ***27*** | α | ***1.7*** | ***61.18*** | ***25*** | ***0.15*** | ***0.22*** | ***0.061*** | ***0.903*** | ***0.006*** |
| ***5*** | ***615-623*** | ***ILEDIVLTL*** | ***28*** | β | ***1.5*** | ***53.29*** | ***29*** | ***0.28*** | ***0.56*** | ***0.023*** | ***0.710*** | ***0.007*** |
| 6 | 614-623 | DILEDIVLTL | 29 | | 4.6 | 3105.79 | 28 | −1.53 | −1.02 | 0.063 | 0.888 | 0.007 |
| 7 | 719-727 | SLHEHIANL | 30 | | 1.4 | 9.14 | 30 | 0.93 | 0.82 | 0.013 | 0.380 | 0.008 |
| 8 | 415-423 | HLGELHAIL | 31 | | 4.4 | 276.73 | 25 | −0.75 | −0.81 | 0.071 | 0.876 | 0.009 |
| 9 | 300-308 | ILLSDILRV | 32 | | 0.3 | 6.51 | 29 | 0.67 | 0.7 | 0.019 | 0.404 | 0.011 |
| 10 | 1086-1095 | VLSMPQVNIV | 33 | | 3.65 | 178.87 | 26 | −1.05 | −1.43 | 0.059 | 0.758 | 0.014 |
| 11 | 719-728 | SLHEHIANLA | 34 | | 4.7 | 60.17 | 19 | −0.98 | −1.74 | 0.126 | 0.890 | 0.014 |
| 12 | 1194-1203 | LIIKLPKYSL | 35 | | 8.5 | 966.31 | 25 | −0.97 | −1.04 | 0.090 | 0.841 | 0.014 |
| 13 | 1346-1355 | TLIHQSITGL | 36 | | 1.95 | 57.8 | 27 | 0.12 | −0.06 | 0.043 | 0.632 | 0.016 |
| 14 | 1197-1207 | KLPKYSLFEL | 37 | | 1.2 | 10.93 | 27 | 0.9 | 0.5 | 0.040 | 0.579 | 0.017 |
| 15 | 1041-1050 | NIMNFFKTEI | 38 | | 2.65 | 314.8 | 19 | −1.03 | −0.9 | 0.121 | 0.857 | 0.017 |
| 16 | 512-520 | SLLYEYFTV | 39 | | 0.4 | 4.56 | 25 | 0.67 | 0.55 | 0.056 | 0.678 | 0.018 |
| 17 | 1309-1318 | IIHLFTLTNL | 40 | | 4.25 | 1083.6 | 24 | −1.04 | −0.78 | 0.085 | 0.787 | 0.018 |
| 18 | 661-670 | RLSRKLINGI | 41 | | 3.5 | 278.03 | 24 | −0.82 | −1.05 | 0.078 | 0.746 | 0.020 |
| 19 | 1227-1236 | ALPSKYVNFL | 42 | | 4.3 | 111.14 | 27 | 0.05 | −0.26 | 0.051 | 0.594 | 0.021 |
| 20 | 996-1004 | ALIKKYPKL | 43 | | 2.6 | 154.09 | 28 | −0.27 | 0 | 0.037 | 0.407 | 0.022 |
| 21 | 221-229 | RLENLIAQL | 44 | | 4.2 | 242.87 | 26 | −0.46 | −0.46 | 0.061 | 0.581 | 0.026 |
| 22 | 1237-1245 | YLASHYEKL | 45 | | 1.2 | 10.3 | 26 | 0.9 | 0.84 | 0.050 | 0.446 | 0.027 |
| 23 | 1265-1273 | YLDEIIEQI | 46 | | 0.3 | 4.8 | 26 | 0.62 | 0.6 | 0.046 | 0.399 | 0.028 |
| 24 | 1042-1050 | IMNFFKTEI | 47 | | 3.2 | 131.4 | 21 | −0.69 | −0.87 | 0.103 | 0.724 | 0.028 |
| 25 | 815-824 | YLQNGRDMYV | 48 | | 0.25 | 13.01 | 22 | −0.18 | −0.07 | 0.083 | 0.627 | 0.031 |
| 26 | 1212-1220 | RMLASAGEL | 49 | | 3.2 | 333.2 | 22 | −0.64 | −0.51 | 0.095 | 0.650 | 0.033 |
| 27 | 1020-1029 | KMIAKSEQEI | 50 | | 3.1 | 64.01 | 21 | −0.36 | −0.9 | 0.103 | 0.671 | 0.034 |
| 28 | 793-801 | SQILKEHPV | 51 | | 2.8 | 191.23 | 16 | −1.4 | −1.36 | 0.149 | 0.766 | 0.035 |
| 29 | 742-750 | KVVDELVKV | 52 | | 2.8 | 44.75 | 24 | −0.06 | −0.26 | 0.074 | 0.505 | 0.036 |
| 30 | 1181-1190 | FLEAKGYKEV | 53 | | 3.25 | 105.27 | 21 | −1.08 | −1.42 | 0.103 | 0.651 | 0.036 |
| 31 | 160-169 | HMIKFRGHFL | 54 | | 4.75 | 324.13 | 21 | −0.59 | −0.73 | 0.110 | 0.628 | 0.041 |
| 32 | 551-559 | LLFKTNRKV | 55 | | 3 | 381.3 | 25 | −1.52 | −1.25 | 0.067 | 0.368 | 0.043 |
| 33 | 141-149 | KLVDSTDKA | 56 | | 3.4 | 274.05 | 20 | −1.48 | −1.17 | 0.114 | 0.520 | 0.055 |
| 34 | 472-481 | TITPWNFEEV | 57 | | 4.45 | 124.55 | 21 | −0.84 | −1.21 | 0.107 | 0.429 | 0.061 |
| 35 | 194-203 | QLFEENPINA | 58 | | 1.65 | 67.94 | 17 | −0.71 | −0.79 | 0.135 | 0.469 | 0.072 |

TABLE 3-continued

Predicted Cas9 immunogenic T cell epitopes

| Rank | Position | Sequence | SEQ ID NO: | Code | Binding IEDB | Binding NetMHC | Binding Syfpeithi | Protein Processing IEDB | Protein Processing ANN | $S_b$ | $S_i$ | $S_b \cdot S_i$ |
|---|---|---|---|---|---|---|---|---|---|---|---|---|
| 36 | 518-527 | FTVYNELTKV | 59 | | 2.55 | 169.93 | 20 | −1.12 | −1.15 | 0.111 | 0.216 | 0.087 |
| 37 | 473-481 | ITPWNFEEV | 60 | | 6.4 | 351.14 | 18 | −1.25 | −1.65 | 0.143 | 0.229 | 0.110 |
| 38 | 970-978 | FQFYKVREI | 61 | | 2.7 | 135.61 | 16 | −0.66 | −0.39 | 0.148 | 0.229 | 0.114 |

The table shows Cas9 HLA-A*02:01 epitopes predicted using an integrative prediction model and ranked according to their $S_b \cdot S_i$ score (the lower the more immunogenic). The immunodominant epitopes (α and β) and subdominant epitopes (γ and δ) as confirmed by ELISpot are noted in lines 1 and 3 (bold) and 4-5 (bold and italics) of the above table, respectively. $S_b$, binding score; $S_i$, immunogenicity score.

Figure 4:
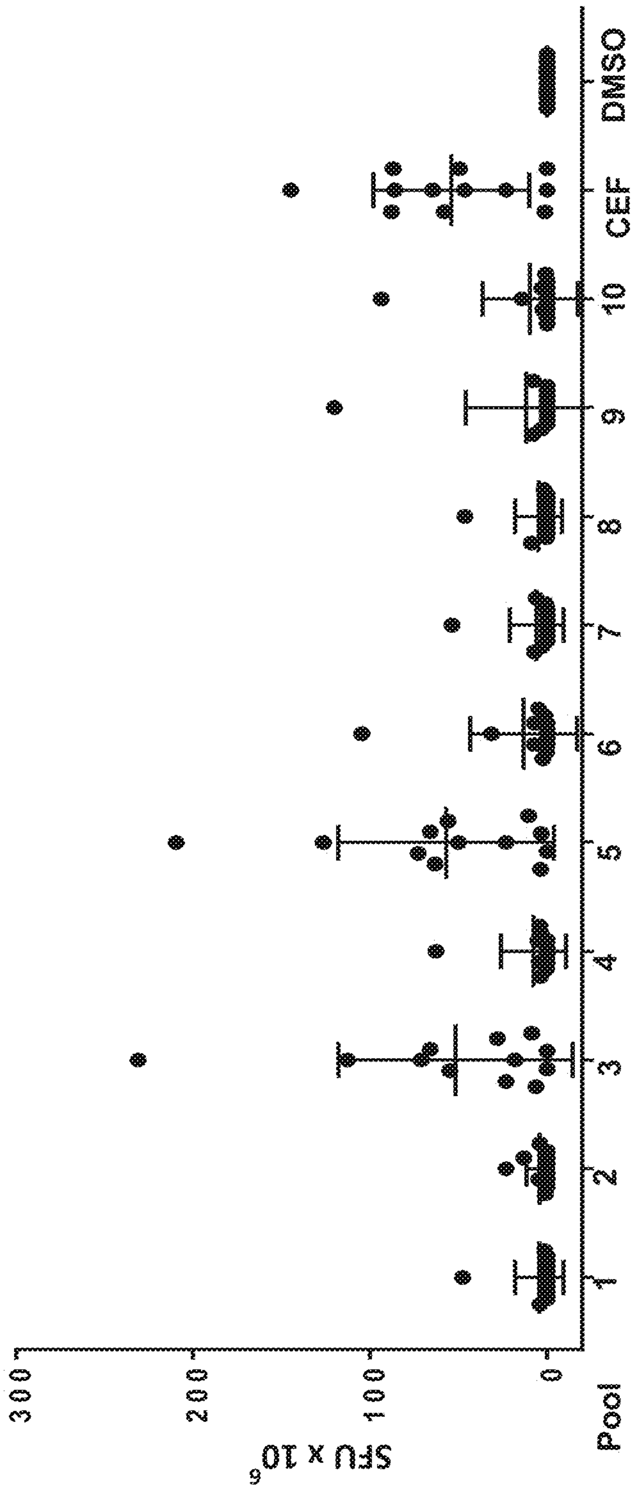
FIG. 4 presents scatter dot plots (median with interquartile range) of IFN-γ ELISpot measurements of T cell reactivity of 12 healthy donors to 38 predicted epitopes grouped in 10 pools, CEF (positive control), and DMSO (negative control). Dots represent the means of triplicate wells for each sample and 2 independent replicates.
Figure 5:
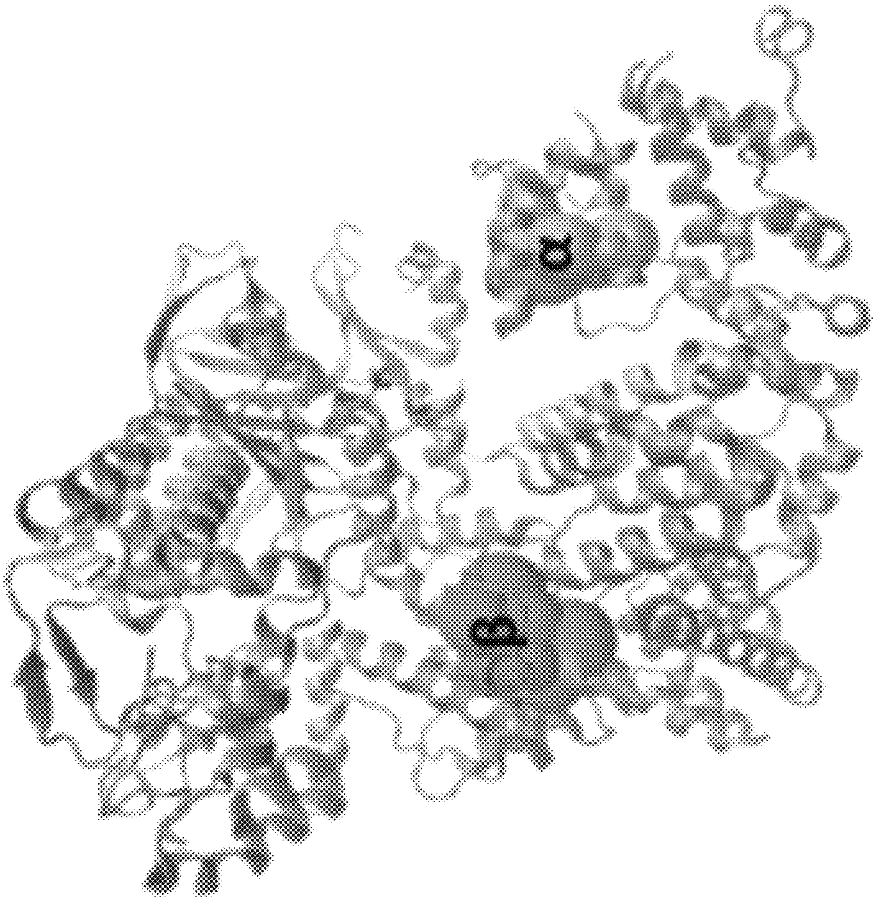
FIG. 5 is three-dimensional (3D) representation of the structure of SpCas9 protein, showing the location of the identified immunodominant epitopes α (previously identified as epitope 85) and β (previously identified as epitope 94).
Figure 6:
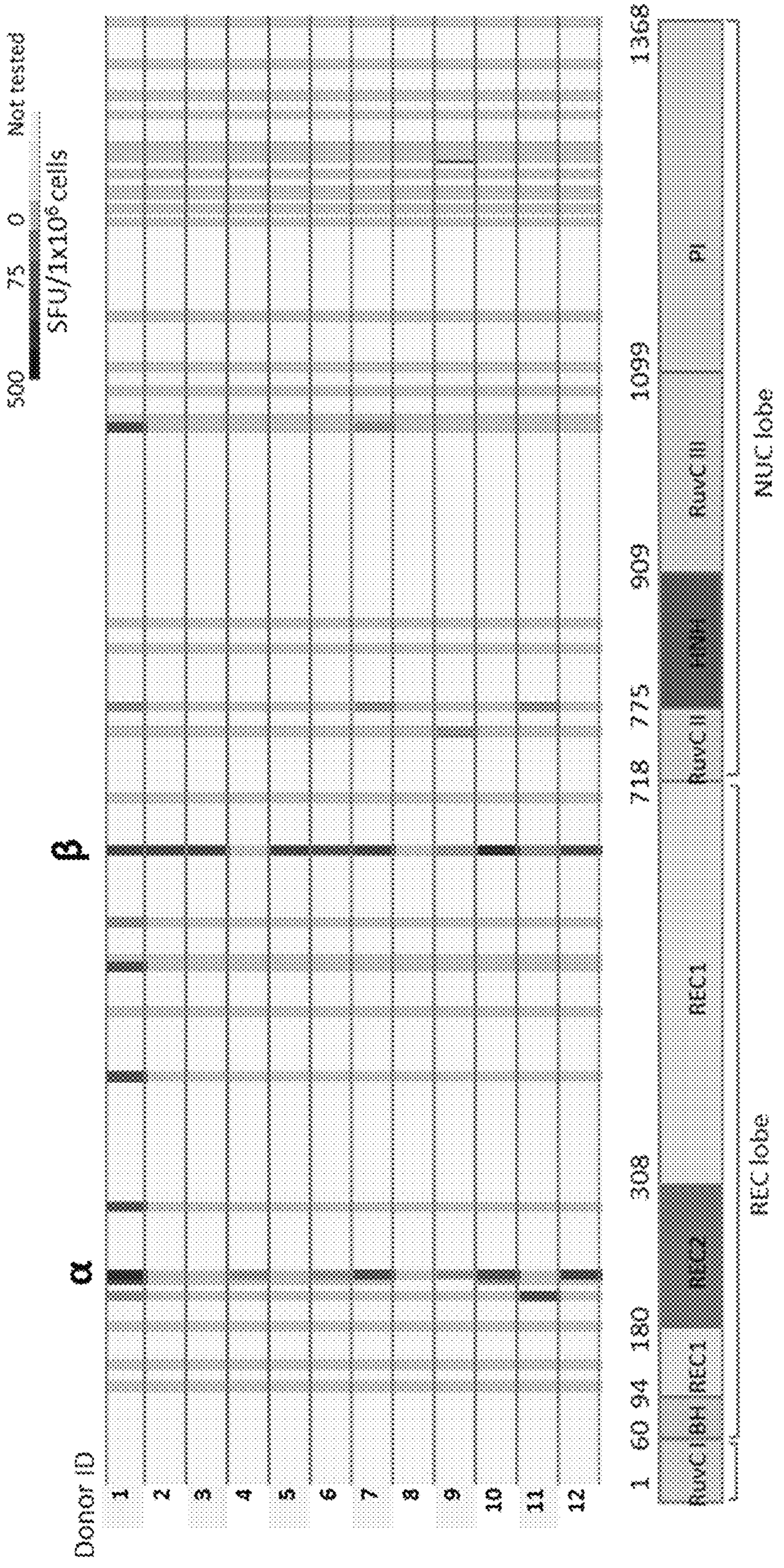
FIG. 6 shows IFN-γ ELISpot reactivity of healthy donor T cells (n=12) to epitopes across the different domains of the Cas9 protein. Epitopes α and β were the most reactive. Results represent the means of triplicate wells for each sample and 2 independent replicates.

Identification of two Cas9 immunodominant T cell epitopes: To determine whether healthy donor peripheral blood mononuclear cells (PBMCs) had measurable T cell reactivity against predicted Cas9 MHC class I epitopes, the top 38 peptides (Table 1) were synthetized and grouped into 10 pools (each containing 3-4 peptides) for screening memory T cell response in healthy individuals using ELISpot. Peptide-specific T cell immunity was measured using IFN-γ secretion ELISpot assays with PBMCs derived from 12 healthy individuals, and immunoreactive epitopes were identified within pools 3 or 5 in 83.0% of the donors tested (FIG. 4). The seven individual peptides from pools 3 and 5 were evaluated by IFN-γ ELISpot and the dominant immunogenic epitopes were SpCas9_293-301 and SpCas9_668-676, designated peptides α and β, from pools 3 and 5, respectively. The position of peptides α and β within the protein structure is shown in FIG. 5. The individual peptides within pools that were positive for any donor were evaluated for this donor by IFN-γ ELISpot. The immunoreactivity and position of the 38 predicted peptides (a few of which are overlapping) within the Cas9 protein are shown in FIG. 6.

Peptides α and β are shown as red dots on the epitope prediction plot and their sequences and predicted ranking are shown in FIG. 3 and Table 3. As predicted, these peptides had low Sb and high Si values. Both the immunodominant (α and β) and subdominant (γ and δ) T cell epitopes identified by IFN-γ ELISpot were within the top 5 epitopes predicted by our previously described immunogenicity model. Sequence similarity of peptides α (previously identified by inventors as immunodominant epitope 85) and β (previously identified by inventors as immunodominant epitope 94) to amino acid sequences in known proteins was investigated using Protein BLAST and the IEDB epitope database. A peptide was considered 'similar' to α or β if at least 7 of 9 (78%) amino acid residues (that are not the second or ninth) were matching. None of these two peptides resembled known epitopes in the IEDB database, but similarity to other Cas9 orthologs and other bacterial proteins was detected (Tables 4 and 5). Epitope β has sequence similarity to a peptide derived from the *Neisseria meningitidis* peptide chain release factor 2 protein (ILEDIVLTL (SEQ ID NO:28) versus ILEGIVLTL (SEQ ID NO:72)).

TABLE 4

Sequence homology of epitope α to amino acid sequences from known proteins

| | Sequence | Epitope SEQ ID NO: | Similarity (%) | Protein | Sequence ID | Source |
|---|---|---|---|---|---|---|
| 1 | NLIALSLGL | 27 | 9/9 (100%) | type II CRISPR RNA-guided endonuclease Cas9 | WP 014612333.1 | *Streptococcus dysgalactiae* |
| 2 | NLIALSLGL | 27 | 9/9 (100%) | type II CRISPR RNA-guided endonuclease Cas9 | WP 054279288.1 | *Streptococcus phocae* |
| 3 | NLIALSLGL | 27 | 9/9 (100%) | type II CRISPR RNA-guided endonuclease Cas9 | WP 067062573.1 | *Streptococcus pantholopis* |
| 4 | NLIALSLGL | 27 | 9/9 (100%) | type II CRISPR RNA-guided endonuclease Cas9 | WP 048800889.1 | *Streptococcus constellatus* |
| 5 | NLIALSLGL | 27 | 9/9 (100%) | type II CRISPR RNA-guided endonuclease Cas9 | WP 002304487.1 | *Streptococcus mutans* |
| 6 | NLIALSLGL | 27 | 9/9 (100%) | type II CRISPR RNA-guided endonuclease Cas9 | WP 049516684.1 | *Streptococcus anginosus* |
| 7 | NLIALSLGL | 27 | 9/9 (100%) | type II CRISPR RNA-guided endonuclease Cas9 | WP 003079701.1 | *Streptococcus macacae* |
| 8 | NLIALSLGL | 27 | 9/9 (100%) | type II CRISPR RNA-guided endonuclease Cas9 | GAD40915.1 | *Streptococcus intermedius* SK54 |

TABLE 4-continued

Sequence homology of epitope α to amino acid sequences from known proteins

| | Sequence | Epitope SEQ ID NO: | Similarity (%) | Protein | Sequence ID | Source |
|---|---|---|---|---|---|---|
| 9 | NLIAFSLGL | 62 | 8/9 (89%) | Full = RNA polymerase-associated protein RapA; AltName: Full = ATP-dependent helicase HepA | Q6LV34.1 | *Photobacterium profundum* SS9 |
| 10 | NLISLSLGL | 63 | 8/9 (89%) | type II CRISPR RNA-guided endonuclease Cas9 | WP 096633625.1 | *Streptococcus parauberis* |
| 11 | NLIALALGL | 64 | 8/9 (89%) | type II CRISPR RNA-guided endonuclease Cas9 | WP 075103982.1 | *Streptococcus cuniculi* |
| 12 | NLIALALGL | 64 | 8/9 (89%) | type II CRISPR RNA-guided endonuclease Cas9 | WP 058692367.1 | *Streptococcus gallolyticus* |
| 13 | NLIALALGL | 64 | 8/9 (89%) | type II CRISPR RNA-guided endonuclease Cas9 | WP 061100419.1 | *Streptococcus pasteurianus* |
| 14 | NLIALALGL | 64 | 8/9 (89%) | type II CRISPR RNA-guided endonuclease Cas9 | WP 018363470.1 | *Streptococcus caballi* |
| 15 | NLIALALGL | 64 | 8/9 (89%) | type II CRISPR RNA-guided endonuclease Cas9 | WP 099412266.1 | *Streptococcus macedonicus* |
| 16 | NLIALALGL | 64 | 8/9 (89%) | type II CRISPR RNA-guided endonuclease Cas9 | WP 014334983.1 | *Streptococcus infantarius* |
| 17 | DLIALYLGL | 65 | 7/9 (78%) | Full = NADH-quinone oxidoreductase subunit N; AltName: Full = NADH dehydrogenase I subunit N; AltName: Full = NDH-1 subunit N | A8I421.1 | *Azorhizabium caulinodans* ORS 571 |
| 18 | NLLALALGL | 66 | 7/9 (78%) | type II CRISPR RNA-guided endonuclease Cas9 | WP 007896501.1 | *Streptococcus pseudoporcinus* |
| 19 | NLIGLALGL | 67 | 7/9 (78%) | type II CRISPR RNA-guided endonuclease Cas9 | WP 061587801.1 | *Streptococcus oralis* |
| 20 | NLVALALGL | 68 | 7/9 (78%) | type II CRISPR RNA-guided endonuclease Cas9 | WP 074862269.1 | *Streptococcus equinus* |
| 21 | NLVALVLGL | 69 | 7/9 (78%) | type II CRISPR RNA-guided endonuclease Cas9 | WP 020917064.1 | *Streptococcus lutetiensis* |
| 22 | SLIAFSLGL | 70 | 7/9 (78%) | ectoine/hydroxyectoine ABC transporter permease subunit EhuD | WP 086160327.1 | *Streptomyces* sp. SCSIO 03032 |
| 23 | YLIALALGL | 71 | 7/9 (78%) | ectoine/hydroxyectoine ABC transporter permease subunit EhuD | WP 026413155.1 | *Actinomadura oligospora* |

TABLE 5

Sequence homology of epitope β to amino acid sequences from known proteins

| | Sequence | Epitope SEQ ID NO: | Similarity (%) | Protein | Sequence ID | Source |
|---|---|---|---|---|---|---|
| 1 | ILEDIVLTL | 28 | 9/9 (100%) | type II CRISPR RNA-guided endonuclease Cas9 | WP 084916602.1 | *Streptococcus dysgalactiae* |
| 2 | ILEDIVLTL | 28 | 9/9 (100%) | type II CRISPR RNA-guided endonuclease Cas9 | WP 074484960.1 | *Streptococcus henryi* |

TABLE 5-continued

Sequence homology of epitope β to amino acid sequences from known proteins

| | Sequence | Epitope SEQ ID NO: | Similarity (%) | Protein | Sequence ID | Source |
|---|---|---|---|---|---|---|
| 3 | ILEDIVLTL | 28 | 9/9 (100%) | type II CRISPR RNA-guided endonuclease Cas9 | WP 003088697.1 | *Streptococcus ratti* |
| 4 | ILEDIVLTL | 28 | 9/9 (100%) | type II CRISPR RNA-guided endonuclease Cas9 | WP 044681799.1 | *Streptococcus suis* |
| 5 | ILEDIVLTL | 28 | 9/9 (100%) | type II CRISPR RNA-guided endonuclease Cas9 | WP 024786433.1 | *Streptococcus mutans* |
| 6 | ILEDIVLTL | 28 | 9/9 (100%) | type II CRISPR RNA-guided endonuclease Cas9 | WP 057491067.1 | *Streptococcus orisasini* |
| 7 | ILEDIVLTL | 28 | 9/9 (100%) | type II CRISPR RNA-guided endonuclease Cas9 | WP 082312238.1 | *Streptococcus intermedius* |
| 8 | ILE**G**IVLTL | 72 | 8/9 (89%) | peptide chain release factor 2 | NP 275123.1 | *Neisseria meningitidis* MC58 |
| 9 | ILEDIV**Q**TL | 73 | 8/9 (89%) | type II CRISPR RNA-guided endonuclease Cas9 | EAO61901.1 | *Streptococcus agalactiae* |
| 10 | ILEDIV**Q**TL | 73 | 8/9 (89%) | type II CRISPR RNA-guided endonuclease Cas9 | WP 070454905.1 | *Streptococcus* sp. HMSC063D10 |
| 11 | **V**LEDIVLTL | 74 | 8/9 (89%) | type II CRISPR RNA-guided endonuclease Cas9 | WP 075346866.1 | *Streptococcus* sp. '*covioe*' |
| 12 | **V**LEDIVL**S**L | 75 | 7/9 (78%) | type II CRISPR RNA-guided endonuclease Cas9 | WP 093650272.1 | *Streptococcus yarani* |
| 13 | ILE**N**IV**H**TL | 76 | 7/9 (78%) | type II CRISPR RNA-guided endonuclease Cas9 | KYF37509.1 | *Streptococcus mitis* |
| 14 | ILE**N**IV**H**TL | 76 | 7/9 (78%) | type II CRISPR RNA-guided endonuclease Cas9 | WP 084972088.1 | *Streptococcus oralis* |
| 15 | ILE**N**IV**H**TL | 76 | 7/9 (78%) | type II CRISPR RNA-guided endonuclease Cas9 | WP 045635197.1 | *Streptococcus gordonii* |

Figures 7A, 7B:
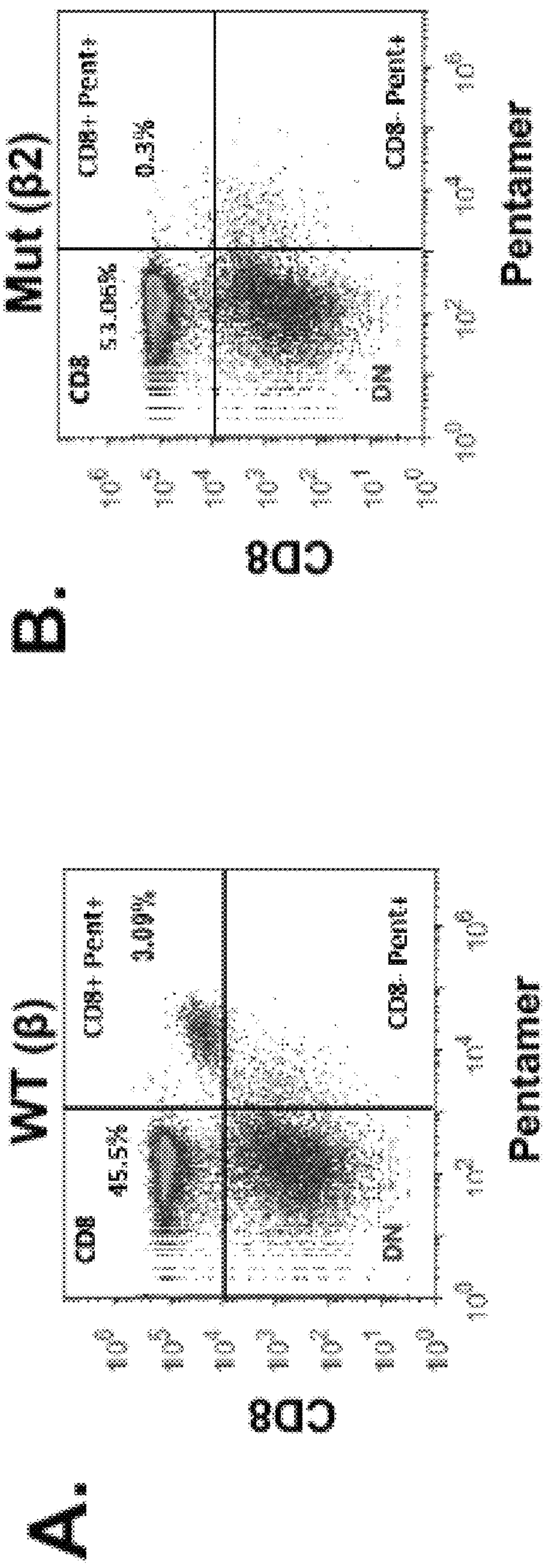

Next, the inventors focused on the immunodominant epitope β. Antigen-specific T cells were expanded for 18 days in vitro by coculturing healthy donor PBMCs with peptide β-pulsed autologous antigen presenting cells (APCs). Cas9-specific CD8+ T cell responses were assessed by flow cytometry. CD8+ T cells specific for the HLA-A*0201/β pentamer were detected after stimulation (3.09%; FIG. 7A).

Figure 7D:
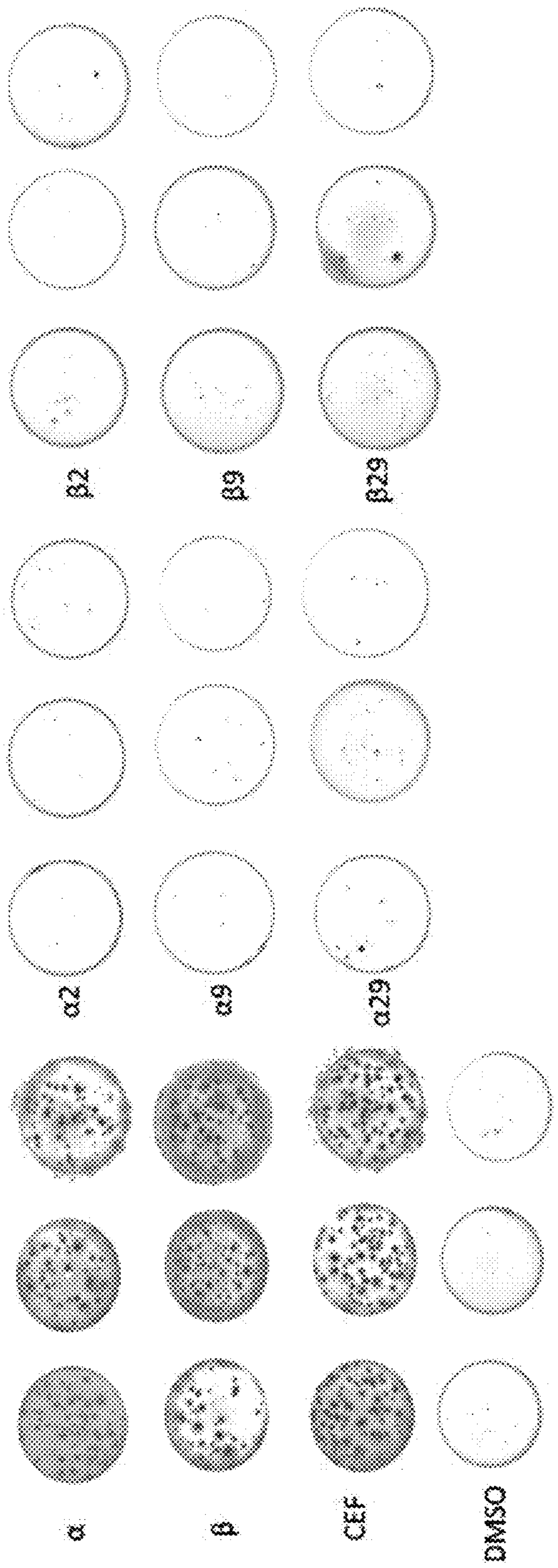
Figures 8A, 8B:
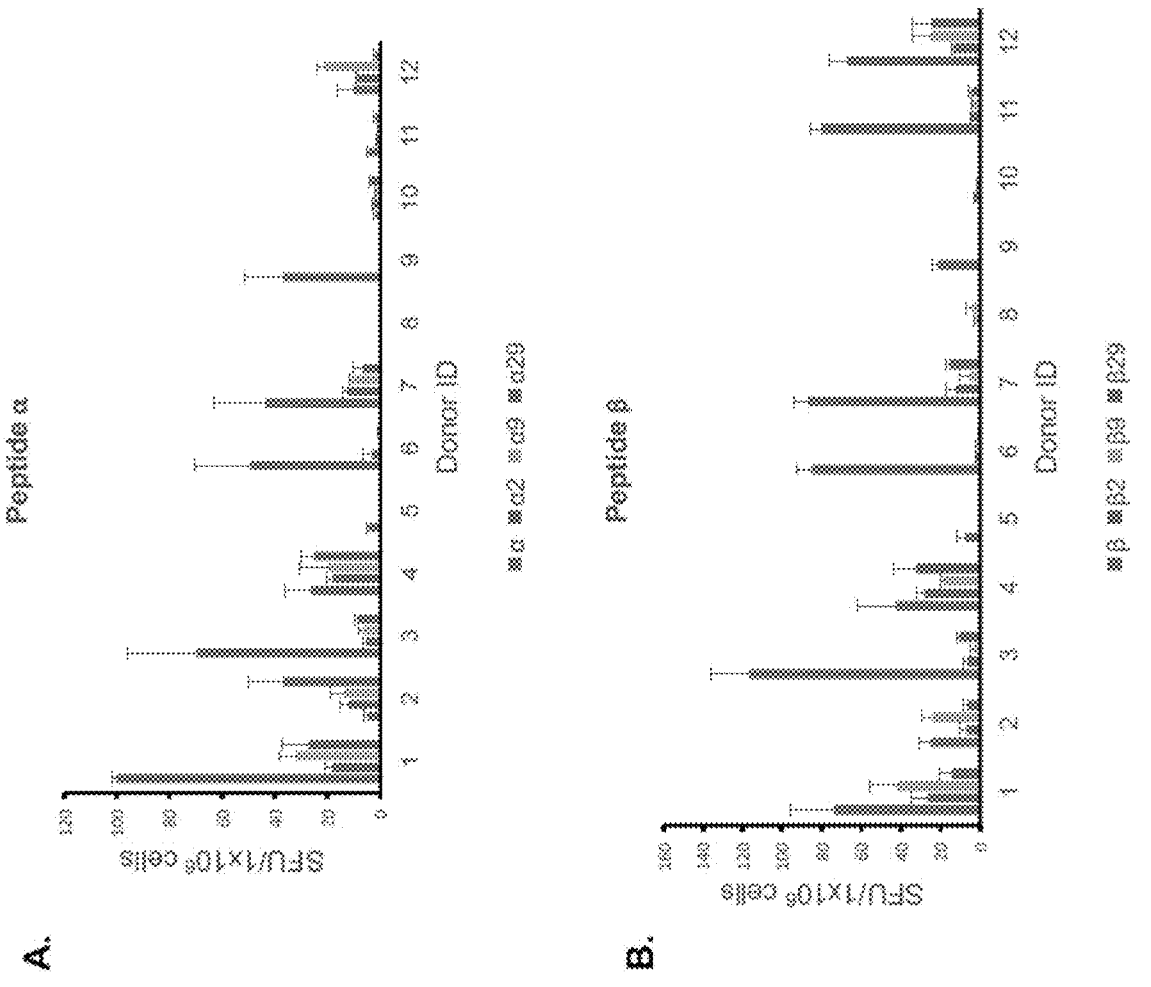
FIGS. 8A-8B demonstrate reduced T cell response to epitopes α and β after mutation of the anchor residues. (A and B) IFN-7 ELISpot for 12 healthy donor PBMCs stimulated with wild type or mutated peptide α (A) or β (B). The average reduction was 8 fold from α to α29 and 25 fold from β to β29 ($p<0.047$). Data represent mean of triplicates and two independent replicates+/−SEM. Two-tailed p value is calculated for paired t tests. A representative ELISPOT image is represented in the FIG. 7D.

It was hypothesized that mutation of the MHC-binding anchor residues of the identified immunogenic epitopes would abolish specific T cell recognition (FIG. 7A). The epitope anchor residues (2nd and 9th) are not only necessary for peptide binding to the MHC groove, but are also crucial for recognition by the T cell receptor 36. The percentage of CD8+ β pentamer+ T cells decreased to 0.3% when APCs were pulsed with the mutated peptide (02; FIG. 7B) compared with 3.09% with the wild type peptide (β; FIG. 7A). The reactivity of healthy donor T cells to modified peptides α or β with mutations in residues 2, 9, or both (sequences are shown in FIG. 7C) was measured using IFN-7 ELISpot assay. The epitope-specific T cell reactivity was markedly reduced with the mutant peptides (FIG. 7D, FIG. 8). The average reduction was 8 fold from α to α29 and 25 fold from β to β29 (n=12; p<0.047; FIG. 8).

Figures 7E, 7F, 7G, 7H, 7I, 7J:
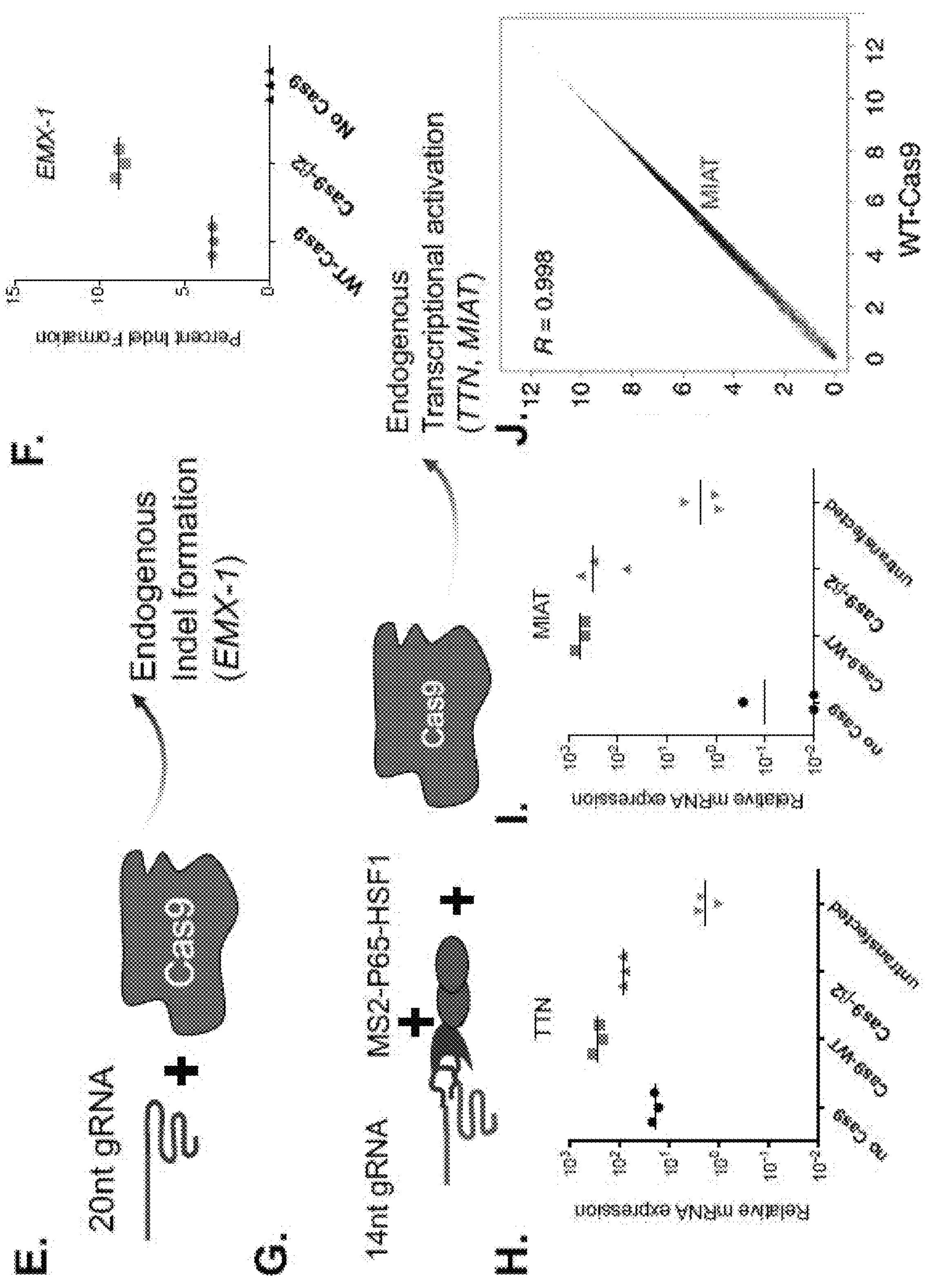
Figures 9A, 9B:
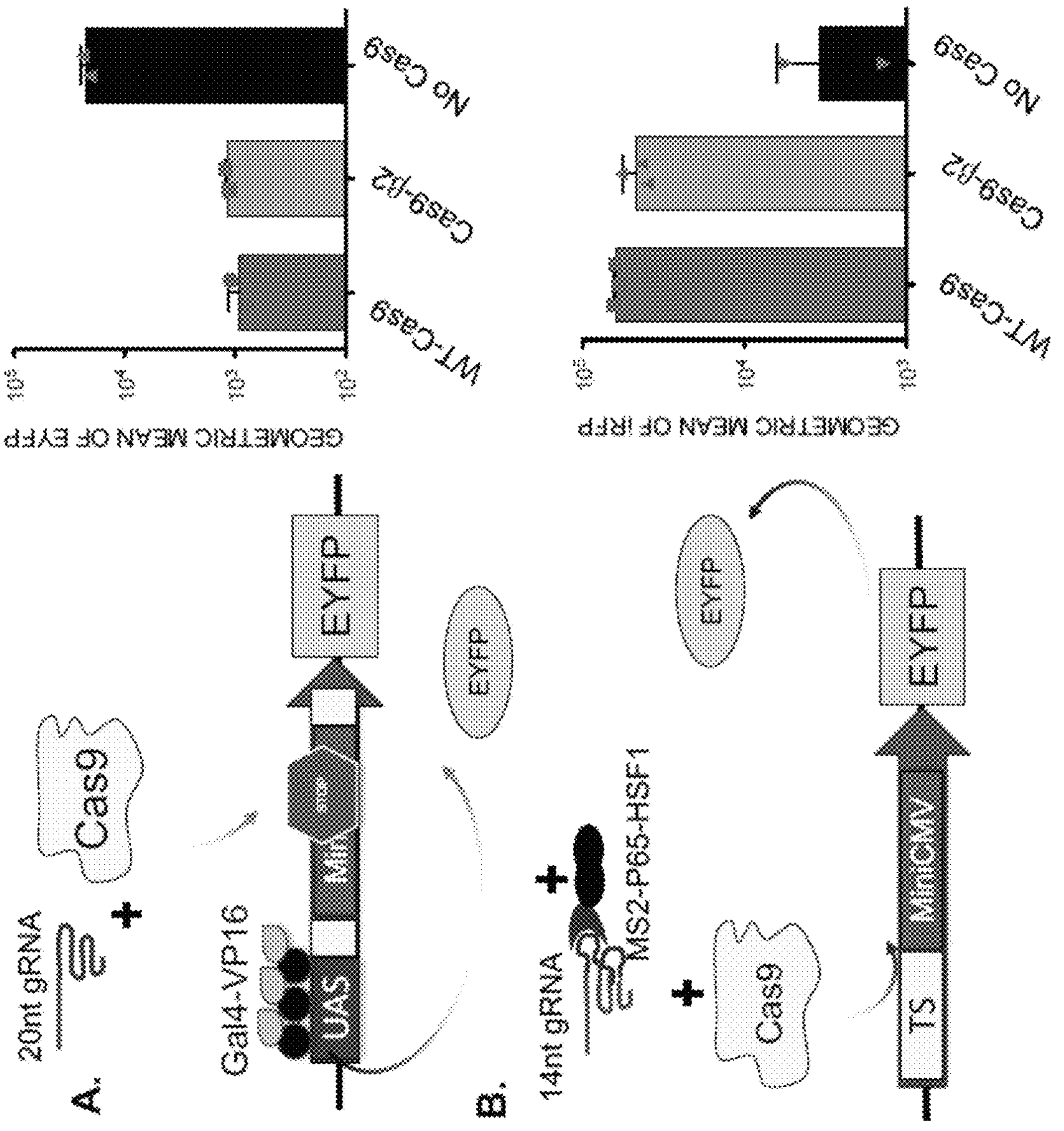
FIGS. 9A-9B. (A)(left) Schematic of the experiment assessing Cas9-β2 cleavage capacity at a synthetic promoter. Cells were transfected with either WT-Cas9, Cas9-β2, or an empty plasmid as well as 20nt gRNA targeting a synthetic CRISPR promoter that harbors two gRNA target sites flanking a mini-CMV promoter. The targeting and cleavage at the promoter should disrupt the promoter and decrease EYFP expression. (A)(right) Bar graphs show mean+/−SD of geometric mean of EYFP expression 48 hours after the transfection in cells expressing $>2\times10^2$ A.U of a transfection marker measured by flow cytometry (n=2 individual transfections represented by individual dots). (B)(left) Schematic of the experiment assessing Cas9-β2 transcriptional activation capacity at a synthetic promoter. Cells were transfected with either WTCas9, Cas9-β2 or an empty plasmid as well as aptamer binding transcriptional activation domains, and 14nt gRNA targeting a synthetic CRISPR promoter that harbors multiple target sites upstream of a mini-CMV promoter. The targeting at the promoter should enable iRFP expression. (B)(right) Bar graph shows mean+/−SD of geometric mean of iRFP expression 48 hours after the transfection in cells expressing $>2\times10^2$ A.U of a transfection marker measured by flow cytometry (n=3 individual transfections represented by individual dots. n=2 for No Cas9 group).

A modified Cas9 construct was produced by mutating the second residue of peptide β (L616G; Cas9-β2) and tested the function of this new Cas9 variant in comparison with wild type Cas9 (WT-Cas9) in the context of DNA cleavage and transcriptional modulation. To examine the nuclease activity of Cas9-β2 and compare with WT-Cas9, Cas9-β2 or WT-Cas9 were targeted to an endogenous locus (EMX-1) and measured percent indel formation (FIGS. 7E, 7F). Our data demonstrate that Cas9-β2 retains nuclease capacity in the locus we studied as well as on a synthetic promoter (FIG. 7F, FIG. 9A). Next, it was determined whether Cas9-β2 can successfully recognize and bind its target DNA leading to transcriptional modulation. First, it was tested in the context of enhanced transgene expression from a synthetic CRISPR responsive promoter in HEK293 cells using 14nt gRNAs and aptamer mediated recruitment of transcriptional modulators similar to what we had shown before (FIG. 9B). Having shown successful transgene activation, it was investigated whether this variant retains such capacity within the chromosomal contexts of endogenous genes. Cells were transfected with plasmids encoding Cas9-β2 or WT-Cas9 and 14nt gRNAs against two different endogenous genes (TTN and MIAT). qRT-PCR analysis showed that this variant successfully led to target gene expression (FIGS. 7G-7I). To further characterize Cas9-β2 specificity, genome-wide RNA sequencing was performed after targeting Cas9-β2 or WT-Cas9 to the MIAT locus for transcriptional activation. The results demonstrated no significant increase in undesired off-target activity by Cas9-β2 as compared to WT-Cas9 (FIG. 7J).

Figures 10A, 10B, 10C, 10D, 10E, 10F:
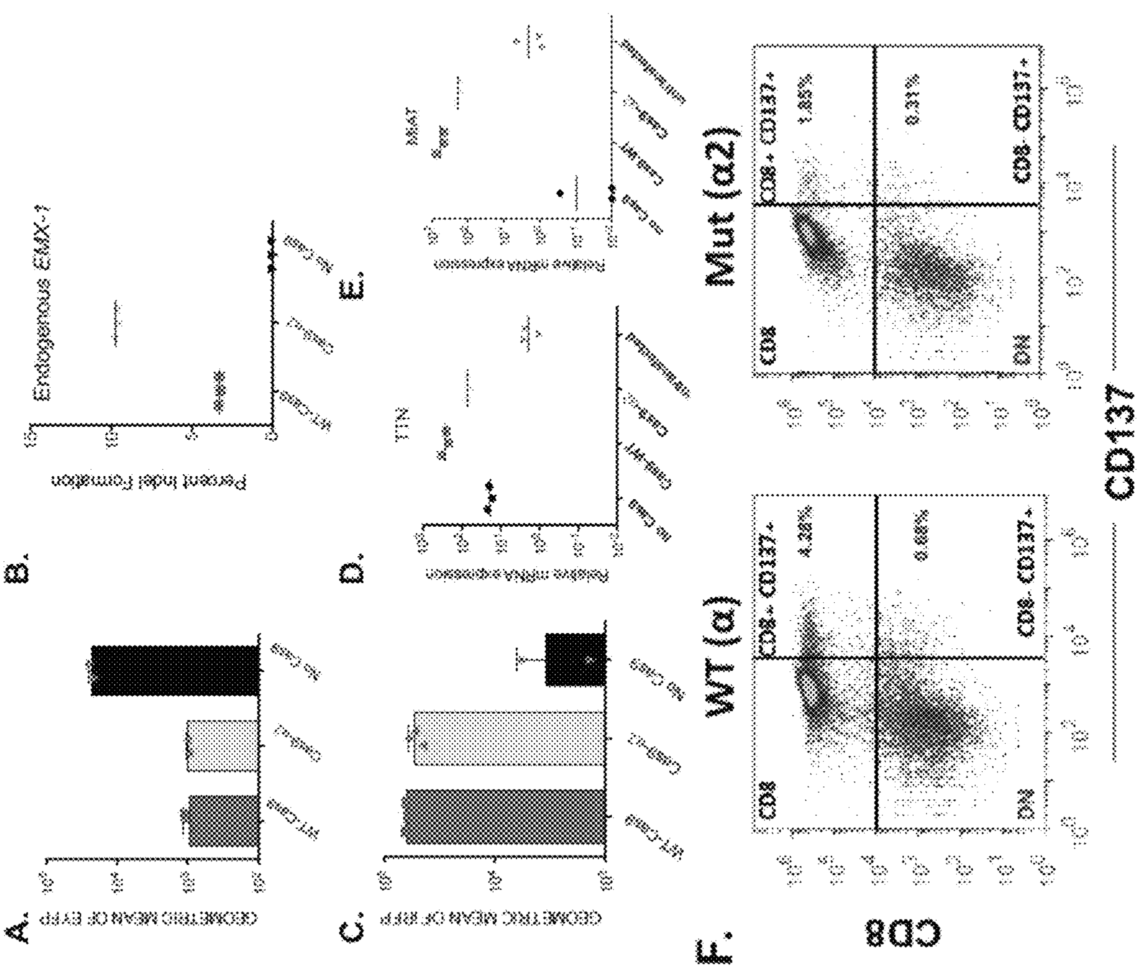
FIGS. 10A-10F. (A) Analysis of mutagenesis capacity of Cas9-α2 as compared to WT Cas9 in a synthetic promoter. Bar graph shows mean+/−SD of geometric mean of EYFP expression 48 hr after transfection in cells expressing $>2\times10^2$ A.U of a transfection marker measured by flow cytometry (n=2 individual transfections, represented by individual dots). (B) Mutagenesis in endogenous EMX-1 locus. Percentage of indel formation in EMX-1 locus. Dots represent three individual transfections. (C) Transcriptional modulation by Cas9-α2 at a synthetic promoter. Bar graph is mean+/−SD of geometric mean of iRFP expression 48 hr after the transfection in cells expressing $>2\times10^2$ A.U of a transfection marker measured by flow cytometry (n=3 individual transfections, n=2 for no Cas9 group represented by dots). (D, E) Shown is mRNA level relative to an untransfected control experiment. Each individual dot represent individual transfections. WT-Cas9 data and no Cas9 data for panels A and C are also presented in FIGS. 9A-9B. For B, D, and E, WT-Cas9 data and no Cas9 data are also presented in FIGS. 7A-7J. (F) Activated CD8+CD137+ T cells detected in PBMCs stimulated with peptide α was reduced in PBMCs stimulated with peptide α2.

To show the extensibility of our approach, another Cas9 variant was generated by mutating the second residue of peptide α (L241G; Cas9-α2). Cas9-α2 also demonstrated DNA cleavage and transcriptional modulation functionality comparable with WT-Cas9 (FIGS. 10A-10E). When T cells were stimulated with APCs spiked with peptide α2, the percentage of CD8+ CD137+ T cells (a marker of T cell activation) was decreased by 2.3 fold as compared to WT peptide α stimulation (FIG. 10F).

The detection of pre-existing B cell and T cell immunity to the most widely used nuclease ortholog of the CRISPR/Cas9 tool in a significant proportion of healthy humans confirms previous studies in mice and sheds light on the need for more studies of the immunological risks of this system. The CD8+ T cell immunity we observed is likely memory responses, as they are observed without ex vivo stimulation. Following 18 days of T cell stimulation by peptides α or β, expansion of naive T cells is not precluded. This suggests that the expression of Cas9 in naive individuals may trigger a T cell response that could prevent subsequent administration. This could be avoided by switching to Cas9 orthologs from other bacterial species, but attention needs to be given to individual and distinct immune repertoires. This can be difficult given the epitope conservation across Cas9 proteins from multiple *Streptococcus* species and resemblance to sequences from other bacterial proteins such as the common pathogen *N. meningitidis* that asymptomatically colonizes the nasopharynx in 10% of the population. Therefore, selective deimmunization (also known as immunosilencing) of Cas9 can represent an attractive alternative. Selective deimmunization can be an effective alternative for CRISPR applications in patients where systemic immunosuppression proves to be difficult, such as in patients with chronic infectious diseases. This strategy can be important particularly when longer expression of Cas9 will be desired for epigenetic therapy.

Conventional methods of deimmunizing non-human therapeutic proteins rely on trial-and-error mutagenesis, machine learning, and often includes deletion of whole regions of the protein. Here, as a general principle, it was determined that alteration of one of the anchor residues of an immunodominant epitope abolished specific T cell recognition. However, HLA allotype diversity and the existence of numerous epitopes in the large Cas9 protein complicate the process of complete deimmunization. The overall impact of removal of select immunodominant epitopes remains to be seen; similar approaches for other proteins have resulted in reduction and enhancement of the immunogenicity of subdominant epitopes. Non-specific immune suppressive approaches may complement these strategies for complete deimmunization. One attractive strategy is the co-expression of Cas9 with gRNAs targeting immune modulatory molecules such as programmed death-ligand 1 (PD-L1) or Indoleamine 2,3-Dioxygenase 1 (IDO1) to further boost immunosilencing. It is believed that deimmunized Cas9 will be useful for therapeutic CRISPR applications as a better understanding of the immunological consequences of this system develops.

The mutated Cas9 protein sequences are as follows, with peptides 85 (α) (SEQ ID NO:27) and 94 (β) (SEQ ID NO:28) in bold, underlined text:

Cas9-α2:

(SEQ ID NO: 2)

MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDLN

PDNSDVDKLFIQLVQTYNQLFEENPINASGVDAKAILSARLSKSRRLENLIAQLPGEKK

NGLFGNGIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVE

DRFNASLGTYHDLLKIIKDKDFLDNEENEDILEDIVLTLTLFEDREMIEERLKTYAHLF

DDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLK

-continued

SVKELLGITIMERSSFEKNPIDFLEAKGYKEVKKDLIIKLPKYSLFELENGRKRMLASA

GELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGD

Cas9-β2

(SEQ ID NO: 3)

MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDLN

PDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVE

DRFNASLGTYHDLLKIIKDKDFLDNEENEDIGEDIVLTLTLFEDREMIEERLKTYAHLF

DDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLK

SVKELLGITIMERSSFEKNPIDFLEAKGYKEVKKDLIIKLPKYSLFELENGRKRMLASA

GELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGD

Cas9-α2-β2

(SEQ ID NO: 4)

MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDLN

PDNSDVDKLFIQLVQTYNQLFEENPINASGVDAKAILSARLSKSRRLENLIAQLPGEKK

NGLFGNGIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVE

DRFNASLGTYHDLLKIIKDKDFLDNEENEDIGEDIVLTLTLFEDREMIEERLKTYAHLF

-continued

DDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLK

SVKELLGITIMERSSFEKNPIDFLEAKGYKEVKKDLIIKLPKYSLFELENGRKRMLASA

GELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGD

Cas9-β2:

(SEQ ID NO: 6)

ATGGACTATAAGGACCACGACGGAGACTACAAGGATCATGATATTGATTACAAAGACGATGACGA

TAAGATGGCCCCAAAGAAGAAGCGGAAGGTCGGTATCCACGGAGTCCCAGCAGCCGACAAGAAG

TACAGCATCGGCCTGGACATCGGCACCAACTCTGTGGGCTGGGCCGTGATCACCGACGAGTACAA

GGTGCCCAGCAAGAAATTCAAGGTGCTGGGCAACACCGACCGGCACAGCATCAAGAAGAACCTG

ATCGGAGCCCTGCTGTTCGACAGCGGCGAAACAGCCGAGGCCACCCGGCTGAAGAGAACCGCCA

GAAGAAGATACACCAGACGGAAGAACCGGATCTGCTATCTGCAAGAGATCTTCAGCAACGAGAT

GGCCAAGGTGGACGACAGCTTCTTCCACAGACTGGAAGAGTCCTTCCTGGTGGAAGAGGATAAGA

AGCACGAGCGGCACCCCATCTTCGGCAACATCGTGGACGAGGTGGCCTACCACGAGAAGTACCCC

ACCATCTACCACCTGAGAAAGAAACTGGTGGACAGCACCGACAAGGCCGACCTGCGGCTGATCTA

TCTGGCCCTGGCCCACATGATCAAGTTCCGGGGCCACTTCCTGATCGAGGGCGACCTGAACCCCG

ACAACAGCGACGTGGACAAGCTGTTCATCCAGCTGGTGCAGACCTACAACCAGCTGTTCGAGGAA

AACCCCATCAACGCCAGCGGCGTGGACGCCAAGGCCATCCTGTCTGCCAGACTGAGCAAGAGCAG

ACGGCTGGAAAATCTGATCGCCCAGCTGCCCGGCGAGAAGAAGAATGGCCTGTTCGGAAACCTTA

TTGCCCTGAGCCTGGGCCTGACCCCCAACTTCAAGAGCAACTTCGACCTGGCCGAGGATGCCAAA

CTGCAGCTGAGCAAGGACACCTACGACGACGACCTGGACAACCTGCTGGCCCAGATCGGCGACCA

GTACGCCGACCTGTTTCTGGCCGCCAAGAACCTGTCCGACGCCATCCTGCTGAGCGACATCCTGAG

AGTGAACACCGAGATCACCAAGGCCCCCCTGAGCGCCTCTATGATCAAGAGATACGACGAGCACC

ACCAGGACCTGACCCTGCTGAAAGCTCTCGTGCGGCAGCAGCTGCCTGAGAAGTACAAAGAGATT

TTCTTCGACCAGAGCAAGAACGGCTACGCCGGCTACATTGACGGCGGAGCCAGCCAGGAAGAGTT

CTACAAGTTCATCAAGCCCATCCTGGAAAAGATGGACGGCACCGAGGAACTGCTCGTGAAGCTGA

ACAGAGAGGACCTGCTGCGGAAGCAGCGGACCTTCGACAACGGCAGCATCCCCCACCAGATCCAC

CTGGGAGAGCTGCACGCCATTCTGCGGCGGCAGGAAGATTTTTACCCATTCCTGAAGGACAACCG

GGAAAAGATCGAGAAGATCCTGACCTTCCGCATCCCCTACTACGTGGGCCCTCTGGCCAGGGGAA

ACAGCAGATTCGCCTGGATGACCAGAAAGAGCGAGGAAACCATCACCCCCTGGAACTTCGAGGA

AGTGGTGGACAAGGGCGCTTCCGCCCAGAGCTTCATCGAGCGGATGACCAACTTCGATAAGAACC

TGCCCAACGAGAAGGTGCTGCCCAAGCACAGCCTGCTGTACGAGTACTTCACCGTGTATAACGAG

-continued

CTGACCAAAGTGAAATACGTGACCGAGGGAATGAGAAAGCCCGCCTTCCTGAGCGGCGAGCAGA

AAAAGGCCATCGTGGACCTGCTGTTCAAGACCAACCGGAAAGTGACCGTGAAGCAGCTGAAAGA

GGACTACTTCAAGAAAATCGAGTGCTTCGACTCCGTGGAAATCTCCGGCGTGGAAGATCGGTTCA

ACGCCTCCCTGGGCACATACCACGATCTGCTGAAAATTATCAAGGACAAGGACTTCCTGGACAAT

GAGGAAAACGAGGACATTGGTGAAGATATCGTGCTGACCCTGACACTGTTTGAGGACAGAGAGAT

GATCGAGGAACGGCTGAAAACCTATGCCCACCTGTTCGACGACAAAGTGATGAAGCAGCTGAAGC

GGCGGAGATACACCGGCTGGGGCAGGCTGAGCCGGAAGCTGATCAACGGCATCCGGGACAAGCA

GTCCGGCAAGACAATCCTGGATTTCCTGAAGTCCGACGGCTTCGCCAACAGAAACTTCATGCAGC

TGATCCACGACGACAGCCTGACCTTTAAAGAGGACATCCAGAAAGCCCAGGTGTCCGGCCAGGGC

GATAGCCTGCACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAGAACATCGTG

ATCGAAATGGCCAGAGAGAACCAGACCACCCAGAAGGGACAGAAGAACAGCCGCGAGAGAATG

AAGCGGATCGAAGAGGGCATCAAAGAGCTGGGCAGCCAGATCCTGAAAGAACACCCCGTGGAAA

ACACCCAGCTGCAGAACGAGAAGCTGTACCTGTACTACCTGCAGAATGGGCGGGATATGTACGTG

GACCAGGAACTGGACATCAACCGGCTGTCCGACTACGATGTGGACCATATCGTGCCTCAGAGCTT

TCTGAAGGACGACTCCATCGACAACAAGGTGCTGACCAGAAGCGACAAGAACCGGGGCAAGAGC

GACAACGTGCCCTCCGAAGAGGTCGTGAAGAAGATGAAGAACTACTGGCGGCAGCTGCTGAACG

CCAAGCTGATTACCCAGAGAAAGTTCGACAATCTGACCAAGGCCGAGAGAGGCGGCCTGAGCGA

ACTGGATAAGGCCGGCTTCATCAAGAGACAGCTGGTGGAAACCCGGCAGATCACAAAGCACGTG

GCACAGATCCTGGACTCCCGGATGAACACTAAGTACGACGAGAATGACAAGCTGATCCGGGAAGT

GAAAGTGATCACCCTGAAGTCCAAGCTGGTGTCCGATTTCCGGAAGGATTTCCAGTTTTACAAAGT

GCGCGAGATCAACAACTACCACCACGCCCACGACGCCTACCTGAACGCCGTCGTGGGAACCGCCC

TGATCAAAAAGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTTCTTCTACAG

CAACATCATGAACTTTTTCAAGACCGAGATTACCCTGGCCAACGGCGAGATCCGGAAGCGGCCTC

TGATCGAGACAAACGGCGAAACCGGGGAGATCGTGTGGGATAAGGGCCGGGATTTTGCCACCGTG

CGGAAAGTGCTGAGCATGCCCCAAGTGAATATCGTGAAAAAGACCGAGGTGCAGACAGGCGGCT

TCAGCAAAGAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGTGGTGGCCA

AAGTGGAAAAGGGCAAGTCCAAGAAACTGAAGAGTGTGAAAGAGCTGCTGGGGATCACCATCAT

GGAAAGAAGCAGCTTCGAGAAGAATCCCATCGACTTTCTGGAAGCCAAGGGCTACAAAGAAGTG

AAAAAGGACCTGATCATCAAGCTGCCTAAGTACTCCCTGTTCGAGCTGGAAAACGGCCGGAAGAG

AATGCTGGCCTCTGCCGGCGAACTGCAGAAGGGAAACGAACTGGCCCTGCCCTCCAAATATGTGA

ACTTCCTGTACCTGGCCAGCCACTATGAGAAGCTGAAGGGCTCCCCCGAGGATAATGAGCAGAAA

CAGCTGTTTGTGGAACAGCACAAGCACTACCTGGACGAGATCATCGAGCAGATCAGCGAGTTCTC

CAAGAGAGTGATCCTGGCCGACGCTAATCTGGACAAAGTGCTGTCCGCCTACAACAAGCACCGGG

ATAAGCCCATCAGAGAGCAGGCCGAGAATATCATCCACCTGTTTACCCTGACCAATCTGGGAGCC

CCTGCCGCCTTCAAGTACTTTGACACCACCATCGACCGGAAGAGGTACACCAGCACCAAAGAGGT

GCTGGACGCCACCCTGATCCACCAGAGCATCACCGGCCTGTACGAGACACGGATCGACCTGTCTC

AGCTGGGAGGCGACAAAAGGCCGGCGGCCACGAAAAAGGCCGGCCAGGCAAAAAAGAAAAAGT

AA

-continued

Cas9-α2:

(SEQ ID NO: 7)

ATGGACTATAAGGACCACGACGGAGACTACAAGGATCATGATATTGATTACAAAGACGATGACGA

TAAGATGGCCCCAAAGAAGAAGCGGAAGGTCGGTATCCACGGAGTCCCAGCAGCCGACAAGAAG

TACAGCATCGGCCTGGACATCGGCACCAACTCTGTGGGCTGGGCCGTGATCACCGACGAGTACAA

GGTGCCCAGCAAGAAATTCAAGGTGCTGGGCAACACCGACCGGCACAGCATCAAGAAGAACCTG

ATCGGAGCCCTGCTGTTCGACAGCGGCGAAACAGCCGAGGCCACCCGGCTGAAGAGAACCGCCA

GAAGAAGATACACCAGACGGAAGAACCGGATCTGCTATCTGCAAGAGATCTTCAGCAACGAGAT

GGCCAAGGTGGACGACAGCTTCTTCCACAGACTGGAAGAGTCCTTCCTGGTGGAAGAGGATAAGA

AGCACGAGCGGCACCCCATCTTCGGCAACATCGTGGACGAGGTGGCCTACCACGAGAAGTACCCC

ACCATCTACCACCTGAGAAAGAAACTGGTGGACAGCACCGACAAGGCCGACCTGCGGCTGATCTA

TCTGGCCCTGGCCCACATGATCAAGTTCCGGGGCCACTTCCTGATCGAGGGCGACCTGAACCCCG

ACAACAGCGACGTGGACAAGCTGTTCATCCAGCTGGTGCAGACCTACAACCAGCTGTTCGAGGAA

AACCCCATCAACGCCAGCGGCGTGGACGCCAAGGCCATCCTGTCTGCCAGACTGAGCAAGAGCAG

ACGGCTGGAAAATCTGATCGCCCAGCTGCCCGGCGAGAAGAAGAATGGCCTGTTCGGAAACGGTA

TTGCCCTGAGCCTGGGCCTGACCCCCAACTTCAAGAGCAACTTCGACCTGGCCGAGGATGCCAAA

CTGCAGCTGAGCAAGGACACCTACGACGACGACCTGGACAACCTGCTGGCCCAGATCGGCGACCA

GTACGCCGACCTGTTTCTGGCCGCCAAGAACCTGTCCGACGCCATCCTGCTGAGCGACATCCTGAG

AGTGAACACCGAGATCACCAAGGCCCCCCTGAGCGCCTCTATGATCAAGAGATACGACGAGCACC

ACCAGGACCTGACCCTGCTGAAAGCTCTCGTGCGGCAGCAGCTGCCTGAGAAGTACAAAGAGATT

TTCTTCGACCAGAGCAAGAACGGCTACGCCGGCTACATTGACGGCGGAGCCAGCCAGGAAGAGTT

CTACAAGTTCATCAAGCCCATCCTGGAAAAGATGGACGGCACCGAGGAACTGCTCGTGAAGCTGA

ACAGAGAGGACCTGCTGCGGAAGCAGCGGACCTTCGACAACGGCAGCATCCCCCACCAGATCCAC

CTGGGAGAGCTGCACGCCATTCTGCGGCGGCAGGAAGATTTTTACCCATTCCTGAAGGACAACCG

GGAAAAGATCGAGAAGATCCTGACCTTCCGCATCCCCTACTACGTGGGCCCTCTGGCCAGGGGAA

ACAGCAGATTCGCCTGGATGACCAGAAAGAGCGAGGAAACCATCACCCCCTGGAACTTCGAGGA

AGTGGTGGACAAGGGCGCTTCCGCCCAGAGCTTCATCGAGCGGATGACCAACTTCGATAAGAACC

TGCCCAACGAGAAGGTGCTGCCCAAGCACAGCCTGCTGTACGAGTACTTCACCGTGTATAACGAG

CTGACCAAAGTGAAATACGTGACCGAGGGAATGAGAAAGCCCGCCTTCCTGAGCGGCGAGCAGA

AAAAGGCCATCGTGGACCTGCTGTTCAAGACCAACCGGAAAGTGACCGTGAAGCAGCTGAAAGA

GGACTACTTCAAGAAAATCGAGTGCTTCGACTCCGTGGAAATCTCCGGCGTGGAAGATCGGTTCA

ACGCCTCCCTGGGCACATACCACGATCTGCTGAAAATTATCAAGGACAAGGACTTCCTGGACAAT

GAGGAAAACGAGGACATTCTTGAAGATATCGTGCTGACCCTGACACTGTTTGAGGACAGAGAGAT

GATCGAGGAACGGCTGAAAACCTATGCCCACCTGTTCGACGACAAAGTGATGAAGCAGCTGAAGC

GGCGGAGATACACCGGCTGGGGCAGGCTGAGCCGGAAGCTGATCAACGGCATCCGGGACAAGCA

GTCCGGCAAGACAATCCTGGATTTCCTGAAGTCCGACGGCTTCGCCAACAGAAACTTCATGCAGC

TGATCCACGACGACAGCCTGACCTTTAAAGAGGACATCCAGAAAGCCCAGGTGTCCGGCCAGGGC

GATAGCCTGCACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAGAACATCGTG

ATCGAAATGGCCAGAGAGAACCAGACCACCCAGAAGGGACAGAAGAACAGCCGCGAGAGAATG

AAGCGGATCGAAGAGGGCATCAAAGAGCTGGGCAGCCAGATCCTGAAAGAACACCCCGTGGAAA

-continued

ACACCCAGCTGCAGAACGAGAAGCTGTACCTGTACTACCTGCAGAATGGGCGGGATATGTACGTG

GACCAGGAACTGGACATCAACCGGCTGTCCGACTACGATGTGGACCATATCGTGCCTCAGAGCTT

TCTGAAGGACGACTCCATCGACAACAAGGTGCTGACCAGAAGCGACAAGAACCGGGGCAAGAGC

GACAACGTGCCCTCCGAAGAGGTCGTGAAGAAGATGAAGAACTACTGGCGGCAGCTGCTGAACG

CCAAGCTGATTACCCAGAGAAAGTTCGACAATCTGACCAAGGCCGAGAGAGGCGGCCTGAGCGA

ACTGGATAAGGCCGGCTTCATCAAGAGACAGCTGGTGGAAACCCGGCAGATCACAAAGCACGTG

GCACAGATCCTGGACTCCCGGATGAACACTAAGTACGACGAGAATGACAAGCTGATCCGGGAAGT

GAAAGTGATCACCCTGAAGTCCAAGCTGGTGTCCGATTTCCGGAAGGATTTCCAGTTTTACAAAGT

GCGCGAGATCAACAACTACCACCACGCCCACGACGCCTACCTGAACGCCGTCGTGGGAACCGCCC

TGATCAAAAAGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTTCTTCTACAG

CAACATCATGAACTTTTTCAAGACCGAGATTACCCTGGCCAACGGCGAGATCCGGAAGCGGCCTC

TGATCGAGACAAACGGCGAAACCGGGGAGATCGTGTGGGATAAGGGCCGGGATTTTGCCACCGTG

CGGAAAGTGCTGAGCATGCCCCAAGTGAATATCGTGAAAAAGACCGAGGTGCAGACAGGCGGCT

TCAGCAAAGAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGTGGTGGCCA

AAGTGGAAAAGGGCAAGTCCAAGAAACTGAAGAGTGTGAAAGAGCTGCTGGGGATCACCATCAT

GGAAAGAAGCAGCTTCGAGAAGAATCCCATCGACTTTCTGGAAGCCAAGGGCTACAAAGAAGTG

AAAAAGGACCTGATCATCAAGCTGCCTAAGTACTCCCTGTTCGAGCTGGAAAACGGCCGGAAGAG

AATGCTGGCCTCTGCCGGCGAACTGCAGAAGGGAAACGAACTGGCCCTGCCCTCCAAATATGTGA

ACTTCCTGTACCTGGCCAGCCACTATGAGAAGCTGAAGGGCTCCCCCGAGGATAATGAGCAGAAA

CAGCTGTTTGTGGAACAGCACAAGCACTACCTGGACGAGATCATCGAGCAGATCAGCGAGTTCTC

CAAGAGAGTGATCCTGGCCGACGCTAATCTGGACAAAGTGCTGTCCGCCTACAACAAGCACCGGG

ATAAGCCCATCAGAGAGCAGGCCGAGAATATCATCCACCTGTTTACCCTGACCAATCTGGGAGCC

CCTGCCGCCTTCAAGTACTTTGACACCACCATCGACCGGAAGAGGTACACCAGCACCAAAGAGGT

GCTGGACGCCACCCTGATCCACCAGAGCATCACCGGCCTGTACGAGACACGGATCGACCTGTCTC

AGCTGGGAGGCGACAAAAGGCCGGCGGCCACGAAAAAGGCCGGCCAGGCAAAAAAGAAAAAGT

AAG

Cas9-α2-β2

(SEQ ID NO: 8)

ATGGACTATAAGGACCACGACGGAGACTACAAGGATCATGATATTGATTACAAAGACGATGACGA

TAAGATGGCCCCAAAGAAGAAGCGGAAGGTCGGTATCCACGGAGTCCCAGCAGCCGACAAGAAG

TACAGCATCGGCCTGGACATCGGCACCAACTCTGTGGGCTGGGCCGTGATCACCGACGAGTACAA

GGTGCCCAGCAAGAAATTCAAGGTGCTGGGCAACACCGACCGGCACAGCATCAAGAAGAACCTG

ATCGGAGCCCTGCTGTTCGACAGCGGCGAAACAGCCGAGGCCACCCGGCTGAAGAGAACCGCCA

GAAGAAGATACACCAGACGGAAGAACCGGATCTGCTATCTGCAAGAGATCTTCAGCAACGAGAT

GGCCAAGGTGGACGACAGCTTCTTCCACAGACTGGAAGAGTCCTTCCTGGTGGAAGAGGATAAGA

AGCACGAGCGGCACCCCATCTTCGGCAACATCGTGGACGAGGTGGCCTACCACGAGAAGTACCCC

ACCATCTACCACCTGAGAAAGAAACTGGTGGACAGCACCGACAAGGCCGACCTGCGGCTGATCTA

TCTGGCCCTGGCCCACATGATCAAGTTCCGGGGCCACTTCCTGATCGAGGGCGACCTGAACCCCG

ACAACAGCGACGTGGACAAGCTGTTCATCCAGCTGGTGCAGACCTACAACCAGCTGTTCGAGGAA

AACCCCATCAACGCCAGCGGCGTGGACGCCAAGGCCATCCTGTCTGCCAGACTGAGCAAGAGCAG

-continued

ACGGCTGGAAAATCTGATCGCCCAGCTGCCCGGCGAGAAGAAGAATGGCCTGTTCGGAAACGGTA

TTGCCCTGAGCCTGGGCCTGACCCCCAACTTCAAGAGCAACTTCGACCTGGCCGAGGATGCCAAA

CTGCAGCTGAGCAAGGACACCTACGACGACGACCTGGACAACCTGCTGGCCCAGATCGGCGACCA

GTACGCCGACCTGTTTCTGGCCGCCAAGAACCTGTCCGACGCCATCCTGCTGAGCGACATCCTGAG

AGTGAACACCGAGATCACCAAGGCCCCCCTGAGCGCCTCTATGATCAAGAGATACGACGAGCACC

ACCAGGACCTGACCCTGCTGAAAGCTCTCGTGCGGCAGCAGCTGCCTGAGAAGTACAAAGAGATT

TTCTTCGACCAGAGCAAGAACGGCTACGCCGGCTACATTGACGGCGGAGCCAGCCAGGAAGAGTT

CTACAAGTTCATCAAGCCCATCCTGGAAAAGATGGACGGCACCGAGGAACTGCTCGTGAAGCTGA

ACAGAGAGGACCTGCTGCGGAAGCAGCGGACCTTCGACAACGGCAGCATCCCCCACCAGATCCAC

CTGGGAGAGCTGCACGCCATTCTGCGGCGGCAGGAAGATTTTTACCCATTCCTGAAGGACAACCG

GGAAAAGATCGAGAAGATCCTGACCTTCCGCATCCCCTACTACGTGGGCCCTCTGGCCAGGGGAA

ACAGCAGATTCGCCTGGATGACCAGAAAGAGCGAGGAAACCATCACCCCCTGGAACTTCGAGGA

AGTGGTGGACAAGGGCGCTTCCGCCCAGAGCTTCATCGAGCGGATGACCAACTTCGATAAGAACC

TGCCCAACGAGAAGGTGCTGCCCAAGCACAGCCTGCTGTACGAGTACTTCACCGTGTATAACGAG

CTGACCAAAGTGAAATACGTGACCGAGGGAATGAGAAAGCCCGCCTTCCTGAGCGGCGAGCAGA

AAAAGGCCATCGTGGACCTGCTGTTCAAGACCAACCGGAAAGTGACCGTGAAGCAGCTGAAAGA

GGACTACTTCAAGAAAATCGAGTGCTTCGACTCCGTGGAAATCTCCGGCGTGGAAGATCGGTTCA

ACGCCTCCCTGGGCACATACCACGATCTGCTGAAAATTATCAAGGACAAGGACTTCCTGGACAAT

GAGGAAAACGAGGACATTGGTGAAGATATCGTGCTGACCCTGACACTGTTTGAGGACAGAGAGAT

GATCGAGGAACGGCTGAAAACCTATGCCCACCTGTTCGACGACAAAGTGATGAAGCAGCTGAAGC

GGCGGAGATACACCGGCTGGGGCAGGCTGAGCCGGAAGCTGATCAACGGCATCCGGGACAAGCA

GTCCGGCAAGACAATCCTGGATTTCCTGAAGTCCGACGGCTTCGCCAACAGAAACTTCATGCAGC

TGATCCACGACGACAGCCTGACCTTTAAAGAGGACATCCAGAAAGCCCAGGTGTCCGGCCAGGGC

GATAGCCTGCACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAGAACATCGTG

ATCGAAATGGCCAGAGAGAACCAGACCACCCAGAAGGGACAGAAGAACAGCCGCGAGAGAATG

AAGCGGATCGAAGAGGGCATCAAAGAGCTGGGCAGCCAGATCCTGAAAGAACACCCCGTGGAAA

ACACCCAGCTGCAGAACGAGAAGCTGTACCTGTACTACCTGCAGAATGGGCGGGATATGTACGTG

GACCAGGAACTGGACATCAACCGGCTGTCCGACTACGATGTGGACCATATCGTGCCTCAGAGCTT

TCTGAAGGACGACTCCATCGACAACAAGGTGCTGACCAGAAGCGACAAGAACCGGGGCAAGAGC

GACAACGTGCCCTCCGAAGAGGTCGTGAAGAAGATGAAGAACTACTGGCGGCAGCTGCTGAACG

CCAAGCTGATTACCCAGAGAAAGTTCGACAATCTGACCAAGGCCGAGAGAGGCGGCCTGAGCGA

ACTGGATAAGGCCGGCTTCATCAAGAGACAGCTGGTGGAAACCCGGCAGATCACAAAGCACGTG

GCACAGATCCTGGACTCCCGGATGAACACTAAGTACGACGAGAATGACAAGCTGATCCGGGAAGT

GAAAGTGATCACCCTGAAGTCCAAGCTGGTGTCCGATTTCCGGAAGGATTTCCAGTTTTACAAAGT

GCGCGAGATCAACAACTACCACCACGCCCACGACGCCTACCTGAACGCCGTCGTGGGAACCGCCC

TGATCAAAAAGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTTCTTCTACAG

CAACATCATGAACTTTTTCAAGACCGAGATTACCCTGGCCAACGGCGAGATCCGGAAGCGGCCTC

TGATCGAGACAAACGGCGAAACCGGGGAGATCGTGTGGGATAAGGGCCGGGATTTTGCCACCGTG

-continued

```
CGGAAAGTGCTGAGCATGCCCCAAGTGAATATCGTGAAAAAGACCGAGGTGCAGACAGGCGGCT

TCAGCAAAGAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGTGGTGGCCA

AAGTGGAAAAGGGCAAGTCCAAGAAACTGAAGAGTGTGAAAGAGCTGCTGGGGATCACCATCAT

GGAAAGAAGCAGCTTCGAGAAGAATCCCATCGACTTTCTGGAAGCCAAGGGCTACAAAGAAGTG

AAAAAGGACCTGATCATCAAGCTGCCTAAGTACTCCCTGTTCGAGCTGGAAAACGGCCGGAAGAG

AATGCTGGCCTCTGCCGGCGAACTGCAGAAGGGAAACGAACTGGCCCTGCCCTCCAAATATGTGA

ACTTCCTGTACCTGGCCAGCCACTATGAGAAGCTGAAGGGCTCCCCCGAGGATAATGAGCAGAAA

CAGCTGTTTGTGGAACAGCACAAGCACTACCTGGACGAGATCATCGAGCAGATCAGCGAGTTCTC

CAAGAGAGTGATCCTGGCCGACGCTAATCTGGACAAAGTGCTGTCCGCCTACAACAAGCACCGGG

ATAAGCCCATCAGAGAGCAGGCCGAGAATATCATCCACCTGTTTACCCTGACCAATCTGGGAGCC

CCTGCCGCCTTCAAGTACTTTGACACCACCATCGACCGGAAGAGGTACACCAGCACCAAAGAGGT

GCTGGACGCCACCCTGATCCACCAGAGCATCACCGGCCTGTACGAGACACGGATCGACCTGTCTC

AGCTGGGAGGCGACAAAAGGCCGGCGGCCACGAAAAAGGCCGGCCAGGCAAAAAAGAAAAAGT
```

SEQUENCE LISTING

```
Sequence total quantity: 82
SEQ ID NO: 1            moltype = AA  length = 1368
FEATURE                 Location/Qualifiers
source                  1..1368
                        mol_type = protein
                        organism = Streptococcus pyogenes
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD            1368

SEQ ID NO: 2            moltype = AA  length = 1368
FEATURE                 Location/Qualifiers
REGION                  1..1368
                        note = Mutated Cas9 protein sequence
source                  1..1368
                        mol_type = protein
                        organism = synthetic construct
SEQUENCE: 2
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
GIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
```

```
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 3            moltype = AA  length = 1368
FEATURE                 Location/Qualifiers
REGION                  1..1368
                        note = Mutated Cas9 protein sequence
source                  1..1368
                        mol_type = protein
                        organism = synthetic construct
SEQUENCE: 3
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDIGEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 4            moltype = AA  length = 1368
FEATURE                 Location/Qualifiers
REGION                  1..1368
                        note = Mutated Cas9 protein sequence
source                  1..1368
                        mol_type = protein
                        organism = synthetic construct
SEQUENCE: 4
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
GIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDIGEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368
```

```
SEQ ID NO: 5           moltype = DNA  length = 4107
FEATURE                Location/Qualifiers
source                 1..4107
                       mol_type = genomic DNA
                       organism = Streptococcus pyogenes
SEQUENCE: 5
atggataaga aatactcaat aggcttagat atcggcacaa atagcgtcgg atgggcggtg  60
atcactgatg aatataaggt tccgtctaaa aagttcaagg ttctgggaaa tacagaccgc  120
cacagtatca aaaaaaatct tataggggct cttttatttg acagtggaga gacagcggaa  180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt cttttttggt ggaagaagac aagaagcatg aacgtcatcc tatttttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca tttttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga  1020
caacaacttc cagaaaagta taaagaaatc ttttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga gaagacaaga agacttttat ccatttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggtacct accatgattt gctaaaaatt  1800
attaaagata aagatttttt ggataatgaa gaaaatgaag atatcttaga ggatattgtt  1860
ttaacattga ccttatttga agatagggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgg cacgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctggttttat caaacgccaa  2760
ttggttgaaa ctcgccaaat cactaagcat gtggcacaaa ttttggatag tcgcatgaat  2820
actaaatacg atgaaaatga taaacttatt cgagaggtta aagtgattac cttaaaatct  2880
aaattagttt ctgacttccg aaaagatttc caattctata aagtacgtga gattaacaat  2940
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
atgattgcta agtctgagca agaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aattatggaa agaagttcct ttgaaaaaaa tccgattgac  3540
tttttagaag ctaaaggata taaggaagtt aaaaaagact taatcattaa actacctaaa  3600
tatagtcttt ttgagttaga aaacggtcgt aaacggatgc tggctagtgc cggagaatta  3660
caaaaaggaa atgagctggc tctgccaagc aaatatgtga atttttata tttagctagt  3720
cattatgaaa agttgaaggg tagtccagaa gataacgaac aaaaacaatt gtttgtggag  3780
cagcataagc attatttaga tgagattatt gagcaaatca gtgaattttc taagcgtgtt  3840
attttagcag atgccaattt agataaagtt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg gtctttatga aacacgcatt  4080
gatttgagtc agctaggagg tgactga                                        4107

SEQ ID NO: 6           moltype = DNA  length = 4272
FEATURE                Location/Qualifiers
```

```
misc_feature          1..4272
                      note = Cas9-Beta2
source                1..4272
                      mol_type = other DNA
                      organism = synthetic construct
SEQUENCE: 6
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtg  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctt  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat ccccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttggtgaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                      4272
```

```
SEQ ID NO: 7           moltype = DNA  length = 4273
FEATURE                Location/Qualifiers
misc_feature           1..4273
                       note = Cas9-alpha2
source                 1..4273
                       mol_type = other DNA
                       organism = synthetic construct
SEQUENCE: 7
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtg  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacggt  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttcttgaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
```

```
aagaaaaagt aag                                                    4273

SEQ ID NO: 8            moltype = DNA  length = 4270
FEATURE                 Location/Qualifiers
misc_feature            1..4270
                        note = Cas9-alpha2-beta2
source                  1..4270
                        mol_type = other DNA
                        organism = synthetic construct
SEQUENCE: 8
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtg  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacggt  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg cccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttggtgaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
```

```
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt                                                          4270

SEQ ID NO: 9            moltype = DNA  length = 14
FEATURE                 Location/Qualifiers
misc_feature            1..14
                        note = MIAT-14bp gRNA
source                  1..14
                        mol_type = other DNA
                        organism = synthetic construct
SEQUENCE: 9
gaggctgagc gcac                                                     14

SEQ ID NO: 10           moltype = DNA  length = 14
FEATURE                 Location/Qualifiers
misc_feature            1..14
                        note = TTN-14bp gRNA
source                  1..14
                        mol_type = other DNA
                        organism = synthetic construct
SEQUENCE: 10
ggaagtctcc tttg                                                     14

SEQ ID NO: 11           moltype = DNA  length = 20
FEATURE                 Location/Qualifiers
misc_feature            1..20
                        note = Reporter2-20bp gRNA
source                  1..20
                        mol_type = other DNA
                        organism = synthetic construct
SEQUENCE: 11
gtcccctcca ccccacagtg                                               20

SEQ ID NO: 12           moltype = DNA  length = 15
FEATURE                 Location/Qualifiers
misc_feature            1..15
                        note = CR10-14bp-gRNA
source                  1..15
                        mol_type = other DNA
                        organism = synthetic construct
SEQUENCE: 12
gcatcaggaa catgt                                                    15

SEQ ID NO: 13           moltype = DNA  length = 24
FEATURE                 Location/Qualifiers
misc_feature            1..24
                        note = EMX1- 20bp gRNA
source                  1..24
                        mol_type = other DNA
                        organism = synthetic construct
SEQUENCE: 13
caccgagtcc gagcagaaga agaa                                          24

SEQ ID NO: 14           moltype = DNA  length = 40
FEATURE                 Location/Qualifiers
misc_feature            1..40
                        note = Cas9 fragment1-FW
source                  1..40
                        mol_type = other DNA
                        organism = synthetic construct
SEQUENCE: 14
ttttggtctc taggtccacc atggactata aggaccacga                         40

SEQ ID NO: 15           moltype = DNA  length = 33
FEATURE                 Location/Qualifiers
misc_feature            1..33
                        note = Cas9 fragment1-RV
source                  1..33
                        mol_type = other DNA
                        organism = synthetic construct
SEQUENCE: 15
tttggtctca gaacagctgg ttgtaggtct gca                                33

SEQ ID NO: 16           moltype = DNA  length = 35
FEATURE                 Location/Qualifiers
misc_feature            1..35
                        note = Cas9 fragment2-FW
source                  1..35
```

```
                          mol_type = other DNA
                          organism = synthetic construct
SEQUENCE: 16
ttttggtctc taccaaccgg aaagtgaccg tgaag                            35

SEQ ID NO: 17             moltype = DNA  length = 34
FEATURE                   Location/Qualifiers
misc_feature              1..34
                          note = Cas9 fragment2-RV
source                    1..34
                          mol_type = other DNA
                          organism = synthetic construct
SEQUENCE: 17
ttttggtctc aaagcttact ttttcttttt tgcc                             34

SEQ ID NO: 18             moltype = DNA  length = 20
FEATURE                   Location/Qualifiers
misc_feature              1..20
                          note = qPCRMIAT-FW
source                    1..20
                          mol_type = other DNA
                          organism = synthetic construct
SEQUENCE: 18
tggctggggt ttgaaccttt                                             20

SEQ ID NO: 19             moltype = DNA  length = 20
FEATURE                   Location/Qualifiers
misc_feature              1..20
                          note = qPCR-MIAT RV
source                    1..20
                          mol_type = other DNA
                          organism = synthetic construct
SEQUENCE: 19
aggaagctgt tccagactgc                                             20

SEQ ID NO: 20             moltype = DNA  length = 20
FEATURE                   Location/Qualifiers
misc_feature              1..20
                          note = qPCRTTN FW
source                    1..20
                          mol_type = other DNA
                          organism = synthetic construct
SEQUENCE: 20
tgttgccact ggtgctaaag                                             20

SEQ ID NO: 21             moltype = DNA  length = 20
FEATURE                   Location/Qualifiers
misc_feature              1..20
                          note = qPCR-TTN-RV
source                    1..20
                          mol_type = other DNA
                          organism = synthetic construct
SEQUENCE: 21
acagcagtct tctccgcttc                                             20

SEQ ID NO: 22             moltype = DNA  length = 20
FEATURE                   Location/Qualifiers
misc_feature              1..20
                          note = PCR-EMX1-FW
source                    1..20
                          mol_type = other DNA
                          organism = synthetic construct
SEQUENCE: 22
ccatcccctt ctgtgaatgt                                             20

SEQ ID NO: 23             moltype = DNA  length = 20
FEATURE                   Location/Qualifiers
misc_feature              1..20
                          note = PCR-EMX1-RV
source                    1..20
                          mol_type = other DNA
                          organism = synthetic construct
SEQUENCE: 23
ggagattgga gacacggaga                                             20

SEQ ID NO: 24             moltype = AA  length = 10
FEATURE                   Location/Qualifiers
REGION                    1..10
                          note = synthetic
```

```
source                1..10
                      mol_type = protein
                      organism = synthetic construct
SEQUENCE: 24
YLNAVVGTAL                                                    10

SEQ ID NO: 25         moltype = AA  length = 10
FEATURE               Location/Qualifiers
REGION                1..10
                      note = synthetic
source                1..10
                      mol_type = protein
                      organism = synthetic construct
SEQUENCE: 25
ILADANLDKV                                                    10

SEQ ID NO: 26         moltype = AA  length = 9
FEATURE               Location/Qualifiers
REGION                1..9
                      note = synthetic
source                1..9
                      mol_type = protein
                      organism = synthetic construct
SEQUENCE: 26
GLFGNLIAL                                                     9

SEQ ID NO: 27         moltype = AA  length = 9
FEATURE               Location/Qualifiers
REGION                1..9
                      note = synthetic
source                1..9
                      mol_type = protein
                      organism = synthetic construct
SEQUENCE: 27
NLIALSLGL                                                     9

SEQ ID NO: 28         moltype = AA  length = 9
FEATURE               Location/Qualifiers
REGION                1..9
                      note = synthetic
source                1..9
                      mol_type = protein
                      organism = synthetic construct
SEQUENCE: 28
ILEDIVLTL                                                     9

SEQ ID NO: 29         moltype = AA  length = 10
FEATURE               Location/Qualifiers
REGION                1..10
                      note = synthetic
source                1..10
                      mol_type = protein
                      organism = synthetic construct
SEQUENCE: 29
DILEDIVLTL                                                    10

SEQ ID NO: 30         moltype = AA  length = 9
FEATURE               Location/Qualifiers
REGION                1..9
                      note = synthetic
source                1..9
                      mol_type = protein
                      organism = synthetic construct
SEQUENCE: 30
SLHEHIANL                                                     9

SEQ ID NO: 31         moltype = AA  length = 9
FEATURE               Location/Qualifiers
REGION                1..9
                      note = synthetic
source                1..9
                      mol_type = protein
                      organism = synthetic construct
SEQUENCE: 31
HLGELHAIL                                                     9

SEQ ID NO: 32         moltype = AA  length = 9
FEATURE               Location/Qualifiers
REGION                1..9
```

```
                        note = synthetic
source                  1..9
                        mol_type = protein
                        organism = synthetic construct
SEQUENCE: 32
ILLSDILRV                                                        9

SEQ ID NO: 33           moltype = AA  length = 10
FEATURE                 Location/Qualifiers
REGION                  1..10
                        note = synthetic
source                  1..10
                        mol_type = protein
                        organism = synthetic construct
SEQUENCE: 33
VLSMPQVNIV                                                       10

SEQ ID NO: 34           moltype = AA  length = 10
FEATURE                 Location/Qualifiers
REGION                  1..10
                        note = synthetic
source                  1..10
                        mol_type = protein
                        organism = synthetic construct
SEQUENCE: 34
SLHEHIANLA                                                       10

SEQ ID NO: 35           moltype = AA  length = 10
FEATURE                 Location/Qualifiers
REGION                  1..10
                        note = synthetic
source                  1..10
                        mol_type = protein
                        organism = synthetic construct
SEQUENCE: 35
LIIKLPKYSL                                                       10

SEQ ID NO: 36           moltype = AA  length = 10
FEATURE                 Location/Qualifiers
REGION                  1..10
                        note = synthetic
source                  1..10
                        mol_type = protein
                        organism = synthetic construct
SEQUENCE: 36
TLIHQSITGL                                                       10

SEQ ID NO: 37           moltype = AA  length = 10
FEATURE                 Location/Qualifiers
REGION                  1..10
                        note = synthetic
source                  1..10
                        mol_type = protein
                        organism = synthetic construct
SEQUENCE: 37
KLPKYSLFEL                                                       10

SEQ ID NO: 38           moltype = AA  length = 10
FEATURE                 Location/Qualifiers
REGION                  1..10
                        note = synthetic
source                  1..10
                        mol_type = protein
                        organism = synthetic construct
SEQUENCE: 38
NIMNFFKTEI                                                       10

SEQ ID NO: 39           moltype = AA  length = 9
FEATURE                 Location/Qualifiers
REGION                  1..9
                        note = synthetic
source                  1..9
                        mol_type = protein
                        organism = synthetic construct
SEQUENCE: 39
SLLYEYFTV                                                        9

SEQ ID NO: 40           moltype = AA  length = 10
FEATURE                 Location/Qualifiers
```

```
REGION                1..10
                      note = synthetic
source                1..10
                      mol_type = protein
                      organism = synthetic construct
SEQUENCE: 40
IIHLFTLTNL                                                  10

SEQ ID NO: 41         moltype = AA  length = 10
FEATURE               Location/Qualifiers
REGION                1..10
                      note = synthetic
source                1..10
                      mol_type = protein
                      organism = synthetic construct
SEQUENCE: 41
RLSRKLINGI                                                  10

SEQ ID NO: 42         moltype = AA  length = 10
FEATURE               Location/Qualifiers
REGION                1..10
                      note = synthetic
source                1..10
                      mol_type = protein
                      organism = synthetic construct
SEQUENCE: 42
ALPSKYVNFL                                                  10

SEQ ID NO: 43         moltype = AA  length = 9
FEATURE               Location/Qualifiers
REGION                1..9
                      note = synthetic
source                1..9
                      mol_type = protein
                      organism = synthetic construct
SEQUENCE: 43
ALIKKYPKL                                                   9

SEQ ID NO: 44         moltype = AA  length = 9
FEATURE               Location/Qualifiers
REGION                1..9
                      note = synthetic
source                1..9
                      mol_type = protein
                      organism = synthetic construct
SEQUENCE: 44
RLENLIAQL                                                   9

SEQ ID NO: 45         moltype = AA  length = 9
FEATURE               Location/Qualifiers
REGION                1..9
                      note = synthetic
source                1..9
                      mol_type = protein
                      organism = synthetic construct
SEQUENCE: 45
YLASHYEKL                                                   9

SEQ ID NO: 46         moltype = AA  length = 9
FEATURE               Location/Qualifiers
REGION                1..9
                      note = synthetic
source                1..9
                      mol_type = protein
                      organism = synthetic construct
SEQUENCE: 46
YLDEIIEQI                                                   9

SEQ ID NO: 47         moltype = AA  length = 9
FEATURE               Location/Qualifiers
REGION                1..9
                      note = synthetic
source                1..9
                      mol_type = protein
                      organism = synthetic construct
SEQUENCE: 47
IMNFFKTEI                                                   9

SEQ ID NO: 48         moltype = AA  length = 10
```

```
FEATURE                Location/Qualifiers
REGION                 1..10
                       note = synthetic
source                 1..10
                       mol_type = protein
                       organism = synthetic construct
SEQUENCE: 48
YLQNGRDMYV                                                    10

SEQ ID NO: 49          moltype = AA  length = 9
FEATURE                Location/Qualifiers
REGION                 1..9
                       note = synthetic
source                 1..9
                       mol_type = protein
                       organism = synthetic construct
SEQUENCE: 49
RMLASAGEL                                                     9

SEQ ID NO: 50          moltype = AA  length = 10
FEATURE                Location/Qualifiers
REGION                 1..10
                       note = synthetic
source                 1..10
                       mol_type = protein
                       organism = synthetic construct
SEQUENCE: 50
KMIAKSEQEI                                                    10

SEQ ID NO: 51          moltype = AA  length = 9
FEATURE                Location/Qualifiers
REGION                 1..9
                       note = synthetic
source                 1..9
                       mol_type = protein
                       organism = synthetic construct
SEQUENCE: 51
SQILKEHPV                                                     9

SEQ ID NO: 52          moltype = AA  length = 9
FEATURE                Location/Qualifiers
REGION                 1..9
                       note = synthetic
source                 1..9
                       mol_type = protein
                       organism = synthetic construct
SEQUENCE: 52
KVVDELVKV                                                     9

SEQ ID NO: 53          moltype = AA  length = 10
FEATURE                Location/Qualifiers
REGION                 1..10
                       note = synthetic
source                 1..10
                       mol_type = protein
                       organism = synthetic construct
SEQUENCE: 53
FLEAKGYKEV                                                    10

SEQ ID NO: 54          moltype = AA  length = 10
FEATURE                Location/Qualifiers
REGION                 1..10
                       note = synthetic
source                 1..10
                       mol_type = protein
                       organism = synthetic construct
SEQUENCE: 54
HMIKFRGHFL                                                    10

SEQ ID NO: 55          moltype = AA  length = 9
FEATURE                Location/Qualifiers
REGION                 1..9
                       note = synthetic
source                 1..9
                       mol_type = protein
                       organism = synthetic construct
SEQUENCE: 55
LLFKTNRKV                                                     9
```

-continued

```
SEQ ID NO: 56           moltype = AA  length = 9
FEATURE                 Location/Qualifiers
REGION                  1..9
                        note = synthetic
source                  1..9
                        mol_type = protein
                        organism = synthetic construct
SEQUENCE: 56
KLVDSTDKA                                                                9

SEQ ID NO: 57           moltype = AA  length = 10
FEATURE                 Location/Qualifiers
REGION                  1..10
                        note = synthetic
source                  1..10
                        mol_type = protein
                        organism = synthetic construct
SEQUENCE: 57
TITPWNFEEV                                                               10

SEQ ID NO: 58           moltype = AA  length = 10
FEATURE                 Location/Qualifiers
REGION                  1..10
                        note = synthetic
source                  1..10
                        mol_type = protein
                        organism = synthetic construct
SEQUENCE: 58
QLFEENPINA                                                               10

SEQ ID NO: 59           moltype = AA  length = 10
FEATURE                 Location/Qualifiers
REGION                  1..10
                        note = synthetic
source                  1..10
                        mol_type = protein
                        organism = synthetic construct
SEQUENCE: 59
FTVYNELTKV                                                               10

SEQ ID NO: 60           moltype = AA  length = 9
FEATURE                 Location/Qualifiers
REGION                  1..9
                        note = synthetic
source                  1..9
                        mol_type = protein
                        organism = synthetic construct
SEQUENCE: 60
ITPWNFEEV                                                                9

SEQ ID NO: 61           moltype = AA  length = 9
FEATURE                 Location/Qualifiers
REGION                  1..9
                        note = synthetic
source                  1..9
                        mol_type = protein
                        organism = synthetic construct
SEQUENCE: 61
FQFYKVREI                                                                9

SEQ ID NO: 62           moltype = AA  length = 9
FEATURE                 Location/Qualifiers
REGION                  1..9
                        note = synthetic
source                  1..9
                        mol_type = protein
                        organism = synthetic construct
SEQUENCE: 62
NLIAFSLGL                                                                9

SEQ ID NO: 63           moltype = AA  length = 9
FEATURE                 Location/Qualifiers
REGION                  1..9
                        note = synthetic
source                  1..9
                        mol_type = protein
                        organism = synthetic construct
SEQUENCE: 63
NLISLSLGL                                                                9
```

```
SEQ ID NO: 64           moltype = AA  length = 9
FEATURE                 Location/Qualifiers
REGION                  1..9
                        note = synthetic
source                  1..9
                        mol_type = protein
                        organism = synthetic construct
SEQUENCE: 64
NLIALALGL                                                         9

SEQ ID NO: 65           moltype = AA  length = 9
FEATURE                 Location/Qualifiers
REGION                  1..9
                        note = synthetic
source                  1..9
                        mol_type = protein
                        organism = synthetic construct
SEQUENCE: 65
DLIALYLGL                                                         9

SEQ ID NO: 66           moltype = AA  length = 9
FEATURE                 Location/Qualifiers
REGION                  1..9
                        note = synthetic
source                  1..9
                        mol_type = protein
                        organism = synthetic construct
SEQUENCE: 66
NLLALALGL                                                         9

SEQ ID NO: 67           moltype = AA  length = 9
FEATURE                 Location/Qualifiers
REGION                  1..9
                        note = synthetic
source                  1..9
                        mol_type = protein
                        organism = synthetic construct
SEQUENCE: 67
NLIGLALGL                                                         9

SEQ ID NO: 68           moltype = AA  length = 9
FEATURE                 Location/Qualifiers
REGION                  1..9
                        note = synthetic
source                  1..9
                        mol_type = protein
                        organism = synthetic construct
SEQUENCE: 68
NLVALALGL                                                         9

SEQ ID NO: 69           moltype = AA  length = 9
FEATURE                 Location/Qualifiers
REGION                  1..9
                        note = synthetic
source                  1..9
                        mol_type = protein
                        organism = synthetic construct
SEQUENCE: 69
NLVALVLGL                                                         9

SEQ ID NO: 70           moltype = AA  length = 9
FEATURE                 Location/Qualifiers
REGION                  1..9
                        note = synthetic
source                  1..9
                        mol_type = protein
                        organism = synthetic construct
SEQUENCE: 70
SLIAFSLGL                                                         9

SEQ ID NO: 71           moltype = AA  length = 9
FEATURE                 Location/Qualifiers
REGION                  1..9
                        note = synthetic
source                  1..9
                        mol_type = protein
                        organism = synthetic construct
SEQUENCE: 71
```

```
YLIALALGL                                                         9

SEQ ID NO: 72          moltype = AA  length = 9
FEATURE                Location/Qualifiers
REGION                 1..9
                       note = synthetic
source                 1..9
                       mol_type = protein
                       organism = synthetic construct
SEQUENCE: 72
ILEGIVLTL                                                         9

SEQ ID NO: 73          moltype = AA  length = 9
FEATURE                Location/Qualifiers
REGION                 1..9
                       note = synthetic
source                 1..9
                       mol_type = protein
                       organism = synthetic construct
SEQUENCE: 73
ILEDIVQTL                                                         9

SEQ ID NO: 74          moltype = AA  length = 9
FEATURE                Location/Qualifiers
REGION                 1..9
                       note = synthetic
source                 1..9
                       mol_type = protein
                       organism = synthetic construct
SEQUENCE: 74
VLEDIVLTL                                                         9

SEQ ID NO: 75          moltype = AA  length = 9
FEATURE                Location/Qualifiers
REGION                 1..9
                       note = synthetic
source                 1..9
                       mol_type = protein
                       organism = synthetic construct
SEQUENCE: 75
VLEDIVLSL                                                         9

SEQ ID NO: 76          moltype = AA  length = 9
FEATURE                Location/Qualifiers
REGION                 1..9
                       note = synthetic
source                 1..9
                       mol_type = protein
                       organism = synthetic construct
SEQUENCE: 76
ILENIVHTL                                                         9

SEQ ID NO: 77          moltype = AA  length = 9
FEATURE                Location/Qualifiers
REGION                 1..9
                       note = synthetic
source                 1..9
                       mol_type = protein
                       organism = synthetic construct
SEQUENCE: 77
NGIALSLGL                                                         9

SEQ ID NO: 78          moltype = AA  length = 9
FEATURE                Location/Qualifiers
REGION                 1..9
                       note = synthetic
source                 1..9
                       mol_type = protein
                       organism = synthetic construct
SEQUENCE: 78
NLIALSLGG                                                         9

SEQ ID NO: 79          moltype = AA  length = 9
FEATURE                Location/Qualifiers
REGION                 1..9
                       note = synthetic
source                 1..9
                       mol_type = protein
                       organism = synthetic construct
```

-continued

```
SEQUENCE: 79
NGIALSLGG                                                      9

SEQ ID NO: 80          moltype = AA  length = 9
FEATURE                Location/Qualifiers
REGION                 1..9
                       note = synthetic
source                 1..9
                       mol_type = protein
                       organism = synthetic construct
SEQUENCE: 80
IGEDIVLTL                                                      9

SEQ ID NO: 81          moltype = AA  length = 9
FEATURE                Location/Qualifiers
REGION                 1..9
                       note = synthetic
source                 1..9
                       mol_type = protein
                       organism = synthetic construct
SEQUENCE: 81
ILEDIVLTG                                                      9

SEQ ID NO: 82          moltype = AA  length = 9
FEATURE                Location/Qualifiers
REGION                 1..9
                       note = synthetic
source                 1..9
                       mol_type = protein
                       organism = synthetic construct
SEQUENCE: 82
IGEDIVLTG                                                      9
```

We claim:

1. An isolated polynucleotide encoding a variant Cas9 polypeptide having the amino acid sequence of SEQ ID NO: 2, SEQ ID NO: 3, or SEQ ID NO: 4.

2. A vector comprising the polynucleotide of claim 1.

3. A host cell comprising the vector of claim 2.

* * * * *